United States Patent
Cotter et al.

(10) Patent No.: US 10,485,909 B2
(45) Date of Patent: Nov. 26, 2019

(54) APICAL CONNECTORS AND INSTRUMENTS FOR USE IN A HEART WALL

(71) Applicant: Thoratec Corporation, Pleasanton, CA (US)

(72) Inventors: Christopher James Cotter, Newburyport, MA (US); Cori Grace Pierce, Melrose, MA (US); Daniel Harjes, Acton, MA (US); Jorge H. Jimenez, Atlanta, GA (US); Julien Duhamel, Billerica, MA (US); Kaitlyn Nicole Spink, Tewksbury, MA (US); Peter J. Gazzara, III, Medford, MA (US); Kathryn Frederick, Pleasanton, CA (US)

(73) Assignee: Thoratec Corporation, Pleasanton, CA (US)

( * ) Notice: Subject to any disclaimer, the term of this patent is extended or adjusted under 35 U.S.C. 154(b) by 42 days.

(21) Appl. No.: 14/928,196

(22) Filed: Oct. 30, 2015

(65) Prior Publication Data
US 2016/0121033 A1     May 5, 2016

Related U.S. Application Data

(60) Provisional application No. 62/167,508, filed on May 28, 2015, provisional application No. 62/073,581, filed on Oct. 31, 2014.

(51) Int. Cl.
*A61B 17/34* (2006.01)
*A61M 1/10* (2006.01)
(Continued)

(52) U.S. Cl.
CPC ....... *A61M 1/1008* (2014.02); *A61B 17/3423* (2013.01); *A61M 1/122* (2014.02);
(Continued)

(58) Field of Classification Search
CPC .................................................. A61M 1/1008
See application file for complete search history.

(56) References Cited

U.S. PATENT DOCUMENTS 3,512,519 A     5/1970    Hall
3,540,451 A    11/1970    Zeman
(Continued)

FOREIGN PATENT DOCUMENTS

CA     2526920     2/2009
CN     1842354    10/2006
(Continued)

OTHER PUBLICATIONS

Supplementary European Search Report and Search Opinion for EP Application No. 15855857.7 dated Jun. 7, 2018 (12 pages).

*Primary Examiner* — Jacqueline Woznicki
(74) *Attorney, Agent, or Firm* — Eversheds Sutherland (US) LLP

(57) ABSTRACT

The present disclosure provides an apical connector for use in a heart wall. The apical connector may include a port defining an aperture therethrough, an anchoring device extending distally from the port and configured for advancing at least partially through the heart wall, and a cannula configured for advancing through the aperture of the port and at least partially through the heart wall. The cannula may include a locking tab configured to engage the port and lock the cannula with respect to the port.

20 Claims, 22 Drawing Sheets

(51) Int. Cl.
*A61M 1/12* (2006.01)
*A61B 17/00* (2006.01)
*A61B 17/32* (2006.01)

(52) U.S. Cl.
CPC .............. *A61B 2017/00252* (2013.01); *A61B 2017/320024* (2013.01); *A61B 2017/3425* (2013.01); *A61B 2017/3488* (2013.01)

(56) References Cited

U.S. PATENT DOCUMENTS

| | | | |
|---|---|---|---|
| 3,856,021 A | 12/1974 | McIntosh | |
| 4,204,541 A | 5/1980 | Kapitanov | |
| 4,366,819 A | 1/1983 | Kaster | |
| 4,769,031 A | 9/1988 | McGough et al. | |
| 4,904,264 A | 2/1990 | Scheunemann | |
| 4,955,856 A | 9/1990 | Phillips | |
| 5,098,369 A | 3/1992 | Heilman et al. | |
| 5,129,913 A | 7/1992 | Ruppert | |
| 5,139,517 A | 8/1992 | Corral | |
| 5,158,563 A | 10/1992 | Cosman | |
| 5,222,980 A | 6/1993 | Gealow | |
| 5,256,160 A | 10/1993 | Clement | |
| 5,291,179 A | 3/1994 | Ooe et al. | |
| 5,387,193 A | 2/1995 | Miracki | |
| 5,447,533 A | 9/1995 | Vachon et al. | |
| 5,456,714 A | 10/1995 | Owen | |
| 5,540,648 A | 7/1996 | Yoon | |
| 5,562,729 A * | 10/1996 | Purdy | A61F 2/2412 623/2.19 |
| 5,577,993 A | 11/1996 | Zhu et al. | |
| 5,582,616 A | 12/1996 | Bolduc et al. | |
| 5,695,504 A | 12/1997 | Gifford et al. | |
| 5,728,116 A | 3/1998 | Rosenman | |
| 5,755,697 A | 5/1998 | Jones et al. | |
| 5,782,844 A | 7/1998 | Yoon et al. | |
| 5,797,933 A | 8/1998 | Snow et al. | |
| 5,810,836 A | 9/1998 | Hussein et al. | |
| 5,810,851 A * | 9/1998 | Yoon | A61B 17/06 606/139 |
| 5,814,005 A | 9/1998 | Barra et al. | |
| 5,824,070 A | 10/1998 | Jarvik | |
| 5,824,071 A | 10/1998 | Nelson et al. | |
| 5,827,316 A | 10/1998 | Young et al. | |
| 5,833,698 A | 11/1998 | Hinchliffe et al. | |
| 5,843,088 A | 12/1998 | Barra et al. | |
| 5,865,791 A | 2/1999 | Whyane et al. | |
| 5,893,369 A | 4/1999 | LeMole | |
| 5,910,153 A | 6/1999 | Mayenberger | |
| 5,924,424 A | 7/1999 | Stevens et al. | |
| 5,944,730 A | 8/1999 | Nobles et al. | |
| 5,976,174 A | 11/1999 | Ruiz | |
| 5,984,956 A | 11/1999 | Tweden et al. | |
| 5,989,278 A | 11/1999 | Mueller | |
| 6,001,056 A | 12/1999 | Jassawalla et al. | |
| 6,007,576 A | 12/1999 | McClellan | |
| 6,022,324 A | 2/2000 | Skinner | |
| 6,022,367 A | 2/2000 | Sherts | |
| 6,024,755 A | 2/2000 | Addis | |
| 6,039,748 A | 3/2000 | Savage et al. | |
| 6,066,085 A | 5/2000 | Heilman et al. | |
| 6,079,414 A | 6/2000 | Roth | |
| 6,080,173 A | 6/2000 | Williamson, IV et al. | |
| 6,080,176 A | 6/2000 | Young | |
| 6,113,611 A | 9/2000 | Allen et al. | |
| 6,146,325 A | 11/2000 | Lewis et al. | |
| 6,241,743 B1 | 6/2001 | Levin et al. | |
| 6,254,564 B1 | 7/2001 | Wilk et al. | |
| 6,267,732 B1 | 7/2001 | Heneveld et al. | |
| 6,273,862 B1 | 8/2001 | Privitera et al. | |
| 6,290,639 B1 | 9/2001 | Mussivand et al. | |
| 6,290,728 B1 | 9/2001 | Phelps et al. | |
| 6,346,071 B1 | 2/2002 | Mussivand | |
| 6,390,976 B1 | 5/2002 | Spence et al. | |
| 6,401,720 B1 | 6/2002 | Stevens et al. | |
| 6,409,739 B1 | 6/2002 | Nobles et al. | |
| 6,443,957 B1 | 9/2002 | Addis | |
| 6,458,140 B2 | 10/2002 | Akin et al. | |
| 6,537,300 B2 | 3/2003 | Girton | |
| 6,551,319 B2 | 4/2003 | Lieberman | |
| 6,551,322 B1 * | 4/2003 | Lieberman | A61B 17/7007 606/246 |
| 6,551,332 B1 | 4/2003 | Nguyen et al. | |
| 6,589,277 B1 | 7/2003 | Fabiani et al. | |
| 6,607,541 B1 | 8/2003 | Gardiner et al. | |
| 6,638,237 B1 | 10/2003 | Guiles et al. | |
| 6,651,670 B2 | 11/2003 | Rapacki et al. | |
| 6,663,633 B1 | 12/2003 | Pierson, III | |
| 6,669,708 B1 | 12/2003 | Nissenbaum et al. | |
| 6,673,043 B1 | 1/2004 | Landesberg | |
| 6,676,678 B2 | 1/2004 | Gifford, III et al. | |
| 6,689,147 B1 | 2/2004 | Koster, Jr. | |
| 6,695,859 B1 | 2/2004 | Golden et al. | |
| 6,699,256 B1 | 3/2004 | Logan et al. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,740,101 B2 | 5/2004 | Houser et al. | |
| 6,776,787 B2 | 8/2004 | Phung et al. | |
| 6,802,806 B2 * | 10/2004 | McCarthy | A61M 1/10 600/16 |
| 6,808,498 B2 | 10/2004 | Laroya et al. | |
| 6,824,071 B1 | 11/2004 | McMichael | |
| 6,827,683 B2 | 12/2004 | Otawara | |
| 6,863,677 B2 | 3/2005 | Breznock | |
| 6,869,437 B1 | 3/2005 | Hausen et al. | |
| 6,942,672 B2 | 9/2005 | Heilman et al. | |
| 6,978,176 B2 | 12/2005 | Lattouf | |
| 6,984,241 B2 | 1/2006 | Lubbers et al. | |
| 6,994,666 B2 | 2/2006 | Shannon et al. | |
| 7,018,384 B2 | 3/2006 | Skakoon | |
| 7,033,372 B1 | 4/2006 | Cahalan | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,083,631 B2 | 8/2006 | Houser et al. | |
| 7,163,525 B2 | 1/2007 | Franer | |
| 7,182,771 B1 | 2/2007 | Houser et al. | |
| 7,214,234 B2 | 5/2007 | Rapacki et al. | |
| 7,232,421 B1 | 6/2007 | Gambale et al. | |
| 7,258,694 B1 | 8/2007 | Choi et al. | |
| 7,309,343 B2 | 12/2007 | Vargas et al. | |
| 7,331,956 B2 | 2/2008 | Hovda et al. | |
| 7,404,792 B2 | 7/2008 | Spence et al. | |
| 7,510,561 B2 | 3/2009 | Beane et al. | |
| 7,637,919 B2 | 12/2009 | Ishikawa et al. | |
| 7,717,844 B2 | 5/2010 | Cohn | |
| 7,744,527 B2 | 6/2010 | Cohn | |
| 7,766,811 B2 | 8/2010 | Haverich | |
| 7,799,041 B2 | 9/2010 | Beane et al. | |
| 7,842,068 B2 | 11/2010 | Ginn | |
| 7,846,123 B2 | 12/2010 | Vassiliades et al. | |
| 7,846,179 B2 | 12/2010 | Belef et al. | |
| 7,931,581 B2 | 4/2011 | Cohn | |
| 7,942,805 B2 | 5/2011 | Shambaugh, Jr. | |
| 7,993,392 B2 | 8/2011 | Righini et al. | |
| 8,226,670 B2 | 7/2012 | Beane et al. | |
| 8,430,836 B2 | 4/2013 | Vassiliades et al. | |
| 8,556,930 B2 | 10/2013 | Ellingwood | |
| 8,579,790 B2 | 11/2013 | Jeffery et al. | |
| 8,764,795 B2 | 7/2014 | Whitman et al. | |
| 8,840,538 B2 | 9/2014 | Jeffery et al. | |
| 8,858,489 B2 | 10/2014 | Vassiliades et al. | |
| 2001/0051809 A1 | 12/2001 | Houser et al. | |
| 2002/0019623 A1 | 2/2002 | Altman et al. | |
| 2002/0019643 A1 | 2/2002 | Gifford et al. | |
| 2002/0032462 A1 | 3/2002 | Houser et al. | |
| 2002/0038127 A1 | 3/2002 | Blatter et al. | |
| 2002/0045846 A1 | 4/2002 | Kaplon et al. | |
| 2002/0055737 A1 * | 5/2002 | Lieberman | A61B 17/701 606/247 |
| 2002/0055738 A1 * | 5/2002 | Lieberman | A61B 17/70 623/17.11 |

(56) References Cited

U.S. PATENT DOCUMENTS

| | | | |
|---|---|---|---|
| 2002/0055739 A1* | 5/2002 | Lieberman | A61B 17/70 606/263 |
| 2002/0055740 A1* | 5/2002 | Lieberman | A61B 17/70 606/263 |
| 2002/0055742 A1* | 5/2002 | Lieberman | A61B 17/70 606/301 |
| 2002/0058958 A1 | 5/2002 | Walen | |
| 2002/0095210 A1* | 7/2002 | Finnegan | A61F 2/064 623/3.26 |
| 2002/0099394 A1 | 7/2002 | Houser et al. | |
| 2002/0116018 A1 | 8/2002 | Stevens et al. | |
| 2002/0177865 A1 | 11/2002 | McIntosh | |
| 2002/0183786 A1 | 12/2002 | Girton | |
| 2002/0193806 A1 | 12/2002 | Moenning et al. | |
| 2003/0014064 A1 | 1/2003 | Blatter | |
| 2003/0023255 A1 | 1/2003 | Miles et al. | |
| 2003/0032979 A1 | 2/2003 | Mortier et al. | |
| 2003/0040765 A1 | 2/2003 | Breznock | |
| 2003/0045834 A1 | 3/2003 | Wing et al. | |
| 2003/0078592 A1 | 4/2003 | Heilman et al. | |
| 2003/0130668 A1 | 7/2003 | Nieman et al. | |
| 2003/0181843 A1 | 9/2003 | Bibber et al. | |
| 2003/0181913 A1* | 9/2003 | Lieberman | A61B 17/1604 606/325 |
| 2004/0002624 A1* | 1/2004 | Yu | A61M 1/10 600/16 |
| 2004/0050393 A1 | 3/2004 | Golden et al. | |
| 2004/0068299 A1 | 4/2004 | Laske et al. | |
| 2004/0073216 A1* | 4/2004 | Lieberman | A61B 17/1604 606/279 |
| 2004/0077989 A1 | 4/2004 | Goode et al. | |
| 2004/0092858 A1 | 5/2004 | Wilson et al. | |
| 2004/0097973 A1 | 5/2004 | Loshakove et al. | |
| 2004/0098011 A1 | 5/2004 | Vargas et al. | |
| 2004/0133155 A1 | 7/2004 | Varner et al. | |
| 2004/0153112 A1 | 8/2004 | Nissenbaum et al. | |
| 2004/0162608 A1 | 8/2004 | Haverich | |
| 2004/0167547 A1 | 8/2004 | Beane et al. | |
| 2004/0167551 A1 | 8/2004 | Gifford, III et al. | |
| 2004/0171905 A1 | 9/2004 | Yu et al. | |
| 2004/0186490 A1 | 9/2004 | Houser et al. | |
| 2004/0225306 A1 | 11/2004 | Blatter et al. | |
| 2004/0236170 A1 | 11/2004 | Kim | |
| 2005/0033107 A1 | 2/2005 | Tsubouchi | |
| 2005/0043781 A1 | 2/2005 | Foley | |
| 2005/0075656 A1 | 4/2005 | Beaupre | |
| 2005/0101982 A1 | 5/2005 | Ravenscroft et al. | |
| 2005/0101983 A1 | 5/2005 | Loshakove et al. | |
| 2005/0131451 A1 | 6/2005 | Kleshinski et al. | |
| 2005/0137609 A1 | 6/2005 | Guiraudon | |
| 2005/0149093 A1 | 7/2005 | Pokorney | |
| 2005/0154411 A1 | 7/2005 | Breznock et al. | |
| 2005/0171479 A1 | 8/2005 | Hruska et al. | |
| 2005/0187568 A1 | 8/2005 | Klenk et al. | |
| 2005/0192604 A1 | 9/2005 | Carson et al. | |
| 2005/0209502 A1 | 9/2005 | Schmid et al. | |
| 2005/0222582 A1* | 10/2005 | Wenchell | A61B 17/3423 606/108 |
| 2005/0251187 A1 | 11/2005 | Beane et al. | |
| 2005/0256368 A1 | 11/2005 | Klenk et al. | |
| 2005/0267495 A1 | 12/2005 | Ginn et al. | |
| 2006/0020326 A9 | 1/2006 | Bolduc et al. | |
| 2006/0036313 A1 | 2/2006 | Vassiliades et al. | |
| 2006/0074484 A1 | 4/2006 | Huber | |
| 2006/0089707 A1 | 4/2006 | Vassiliades et al. | |
| 2006/0099716 A1 | 5/2006 | Tipler et al. | |
| 2006/0142634 A1 | 6/2006 | Anstadt et al. | |
| 2006/0161193 A1 | 7/2006 | Beane et al. | |
| 2006/0167333 A1 | 7/2006 | Moore et al. | |
| 2006/0241659 A1 | 10/2006 | Tulleken et al. | |
| 2006/0259050 A1 | 11/2006 | DeWinter | |
| 2007/0055357 A1 | 3/2007 | Pokorney et al. | |
| 2007/0066943 A1 | 3/2007 | Prasad et al. | |
| 2007/0088375 A1 | 4/2007 | Beane et al. | |
| 2007/0100363 A1 | 5/2007 | Dollar et al. | |
| 2007/0106315 A1 | 5/2007 | Gregoric et al. | |
| 2007/0106328 A1 | 5/2007 | Wardle et al. | |
| 2007/0112361 A1 | 5/2007 | Schonholz et al. | |
| 2007/0167968 A1 | 7/2007 | Pandey | |
| 2007/0167969 A1 | 7/2007 | Pandey | |
| 2007/0173879 A1 | 7/2007 | Pandey | |
| 2007/0197856 A1 | 8/2007 | Gellman et al. | |
| 2007/0208214 A1 | 9/2007 | Hjelle et al. | |
| 2007/0265643 A1 | 11/2007 | Beane et al. | |
| 2008/0004640 A1 | 1/2008 | Ellingwood | |
| 2008/0009668 A1 | 1/2008 | Cohn | |
| 2008/0009887 A1 | 1/2008 | Cohn | |
| 2008/0009891 A1 | 1/2008 | Cohn | |
| 2008/0039883 A1 | 2/2008 | Nohilly | |
| 2008/0058846 A1 | 3/2008 | Vosough | |
| 2008/0076959 A1 | 3/2008 | Farnan et al. | |
| 2008/0161826 A1 | 7/2008 | Guiraudon | |
| 2008/0177301 A1 | 7/2008 | Svensson | |
| 2008/0255597 A1 | 10/2008 | Pravong et al. | |
| 2009/0012552 A1 | 1/2009 | Pandey et al. | |
| 2009/0082778 A1 | 3/2009 | Beane et al. | |
| 2009/0112062 A1 | 4/2009 | Bakos | |
| 2009/0182282 A1 | 7/2009 | Okihisa et al. | |
| 2009/0203957 A1 | 8/2009 | LaRose et al. | |
| 2009/0204206 A1 | 8/2009 | Parquet et al. | |
| 2009/0240264 A1 | 9/2009 | Tuval et al. | |
| 2010/0004739 A1 | 1/2010 | Vesely | |
| 2010/0010500 A1 | 1/2010 | Beane et al. | |
| 2010/0010616 A1 | 1/2010 | Drews et al. | |
| 2010/0049225 A1 | 2/2010 | To et al. | |
| 2010/0087907 A1 | 4/2010 | Lattouf | |
| 2010/0160847 A1 | 6/2010 | Braido et al. | |
| 2010/0161040 A1 | 6/2010 | Braido et al. | |
| 2010/0168778 A1 | 7/2010 | Braido | |
| 2010/0262080 A1 | 10/2010 | Shelton, IV et al. | |
| 2011/0092761 A1 | 4/2011 | Almog et al. | |
| 2011/0106116 A1 | 5/2011 | Ducharme et al. | |
| 2011/0118766 A1 | 5/2011 | Reichenbach et al. | |
| 2011/0118770 A1 | 5/2011 | Pokorney et al. | |
| 2011/0118833 A1 | 5/2011 | Reichenbach et al. | |
| 2011/0144680 A1 | 6/2011 | Nguyen et al. | |
| 2011/0160850 A1 | 6/2011 | Bourque | |
| 2011/0190811 A1 | 8/2011 | Shanley | |
| 2011/0196190 A1 | 8/2011 | Farnan et al. | |
| 2011/0224785 A1* | 9/2011 | Hacohen | A61B 17/0401 623/2.18 |
| 2011/0251450 A1 | 10/2011 | Pagani et al. | |
| 2012/0059212 A1 | 3/2012 | LaRose et al. | |
| 2012/0059457 A1 | 3/2012 | Leinsing et al. | |
| 2012/0089181 A1 | 4/2012 | Shanley et al. | |
| 2012/0123452 A1 | 5/2012 | Asfora et al. | |
| 2012/0123461 A1 | 5/2012 | Gillies et al. | |
| 2012/0226096 A1 | 9/2012 | Callaway et al. | |
| 2012/0253386 A1 | 10/2012 | Rowe et al. | |
| 2012/0296151 A1 | 11/2012 | Curtis et al. | |
| 2012/0296358 A1 | 11/2012 | Nguyen et al. | |
| 2013/0012761 A1 | 1/2013 | Gregoric et al. | |
| 2013/0060267 A1 | 3/2013 | Farnan et al. | |
| 2013/0110228 A1 | 5/2013 | Braido | |
| 2013/0116728 A1 | 5/2013 | Litvack et al. | |
| 2013/0150654 A1 | 6/2013 | Stanfield et al. | |
| 2013/0218169 A1 | 8/2013 | Vassiliades et al. | |
| 2013/0253641 A1 | 9/2013 | Lattouf | |
| 2014/0039375 A1 | 2/2014 | Jimenez et al. | |
| 2014/0067057 A1 | 3/2014 | Callaway et al. | |
| 2014/0100430 A1 | 4/2014 | Beane et al. | |
| 2014/0148786 A1 | 5/2014 | Milo | |
| 2014/0194833 A1 | 7/2014 | Andrus | |
| 2014/0214159 A1* | 7/2014 | Vidlund | A61L 27/34 623/2.14 |
| 2014/0378772 A1 | 12/2014 | Sundt, III et al. | |
| 2014/0379074 A1* | 12/2014 | Spence | A61F 2/2418 623/2.11 |
| 2015/0032153 A1 | 1/2015 | Quadri et al. | |
| 2015/0038770 A1 | 2/2015 | Colella | |
| 2015/0112120 A1* | 4/2015 | Andrus | A61M 1/1008 600/16 |

(56) References Cited

U.S. PATENT DOCUMENTS

| | | | |
|---|---|---|---|
| 2015/0196321 A1 | 7/2015 | Gregory et al. | |
| 2016/0067395 A1* | 3/2016 | Jimenez | A61M 1/10 606/151 |
| 2016/0095705 A1* | 4/2016 | Keranen | A61F 2/2445 623/2.36 |

FOREIGN PATENT DOCUMENTS

| | | |
|---|---|---|
| EP | 1 669 042 | 6/2006 |
| EP | 1 706 168 | 10/2006 |
| EP | 1 691 884 | 3/2011 |
| EP | 1 628 702 | 5/2013 |
| JP | 09-47457 | 2/1997 |
| JP | 11-500642 | 1/1999 |
| JP | 2002-518082 | 6/2002 |
| JP | 2006-518624 | 8/2006 |
| JP | 2007-510522 | 4/2007 |
| WO | 93/25148 | 12/1993 |
| WO | 96/25886 | 8/1996 |
| WO | 97/13463 | 4/1997 |
| WO | 99/65409 | 12/1999 |
| WO | 00/00193 | 1/2000 |
| WO | 00/15147 | 3/2000 |
| WO | 00/15149 | 3/2000 |
| WO | 2000/074747 | 12/2000 |
| WO | 2003/001980 | 1/2003 |
| WO | 2004/026147 | 4/2004 |
| WO | 2004/096059 | 11/2004 |
| WO | 2005/046783 | 5/2005 |
| WO | 2006/019755 | 2/2006 |
| WO | 2006/020651 | 2/2006 |
| WO | 2006/093970 | 9/2006 |
| WO | 2007/038109 | 4/2007 |
| WO | 2007/047212 | 4/2007 |
| WO | 2007/117612 | 10/2007 |
| WO | 2008/131453 | 10/2008 |
| WO | 2008/153872 | 12/2008 |
| WO | 2009/100198 | 8/2009 |
| WO | 2009/117435 | 9/2009 |
| WO | 2012/040233 | 3/2012 |
| WO | 2012/103546 | 8/2012 |
| WO | 2012/106422 | 8/2012 |
| WO | 2013/064529 | 5/2013 |
| WO | 2013/189620 | 12/2013 |
| WO | 2015/109328 | 7/2015 |

* cited by examiner

APICAL CONNECTORS AND INSTRUMENTS FOR USE IN A HEART WALL

CROSS-REFERENCE TO RELATED APPLICATIONS

This application claims the benefit of U.S. Provisional Application No. 62/073,581, filed Oct. 31, 2014, and U.S. Provisional Application No. 62/167,508, filed May 28, 2015, the entire contents of which are incorporated herein by reference in their entirety.

FIELD OF THE DISCLOSURE

The present disclosure relates generally to devices, systems, and methods for implanting and using a connector in a tissue wall to establish, maintain, control, and close a fluid communication between opposing surfaces of the tissue wall. In particular, the present disclosure relates to apical connectors and instruments for use in a heart wall to facilitate in vivo implantation of a ventricular assist device and its attachment to the heart.

BACKGROUND OF THE DISCLOSURE

Mechanical circulatory support (MCS) systems assist the heart in circulating blood in the body. A ventricular assist device (VAD) is an example of an MCS system that is used to assist one or both ventricles of the heart to circulate blood. For patients suffering from heart failure, assisting the left ventricle of the heart via a left ventricular assist device (LVAD) extending between the left ventricle and the aorta is more common, although the right ventricle may be assisted via a right ventricular assist device (RVAD) extending between the right ventricle and the pulmonary artery. Two VADs can also be used in a BiVAD configuration. Currently, VADs are commonly used for destination therapy or as a bridge to transplant option for patients with heart failure.

According to current techniques for LVAD implantation, which typically are performed on-pump (i.e., employing cardiopulmonary bypass), a hole is formed in the heart wall, typically at or near the apex of the left ventricle, and a connector or conduit is secured within or about the hole. RVAD implantation techniques, which also tend to be performed on-pump, involve forming a hole in the lateral wall of the right ventricle and securing a connector or conduit within or about the hole. After establishing a fluid tight connection between the conduit and the ventricular wall, an inlet tube of the VAD is attached to the connector or conduit, which allows blood to flow from the ventricle to a pump of the VAD. Due to the substantial risks of cardiopulmonary bypass, particularly for patients with advanced heart failure, it would be highly desirable to implant the VAD during an off-pump procedure. However, due to challenges in forming a hole in the ventricle of an active heart, reliably securing the connector or conduit in the heart wall, and reliably attaching the inlet tube of the VAD to the connector or conduit, on-pump techniques remain common for VAD implantation.

Various connectors and instruments have been developed for use in a heart wall to facilitate in vivo implantation of a VAD and its attachment to the heart. However, improved connectors, instruments, and related methods are desired for quickly, safely, and reliably implanting a VAD without the use of cardiopulmonary bypass while minimizing blood loss.

SUMMARY OF THE DISCLOSURE

Various embodiments of the present disclosure provide improved connectors, instruments, and related methods for quickly, safely, and reliably implanting a VAD in a manner that eliminates or reduces the need for cardiopulmonary bypass while also minimizing blood loss. In one aspect, an apical connector is provided for use in a heart wall. The apical connector may include a port defining an aperture therethrough, an anchoring device extending distally from the port and configured for advancing at least partially through the heart wall, and a cannula configured for advancing through the aperture of the port and at least partially through the heart wall. The cannula may include a locking tab configured to engage the port and lock the cannula with respect to the port.

In another aspect, an apical connector is provided for use in a heart wall. The apical connector may include a port defining an aperture therethrough, and an anchoring device extending distally from the port and configured for advancing at least partially through the heart wall. The anchoring device may include a plurality of coils offset from one another and arranged in a generally symmetric manner about a central axis of the apical connector such that the coils follow separate helical paths in the heart wall.

In still another aspect, an apical connector is provided for use in a heart wall. The apical connector may include a port defining an aperture therethrough, a sewing ring extending radially outward from the port and configured for suturing to the heart wall, and an anchoring device extending distally from the port and configured for advancing at least partially through the heart wall. The anchoring device may include a coil.

These and other features and improvements of embodiments of the present disclosure will be apparent or will become apparent to one of ordinary skill in the art upon review of the following detailed description when taken in conjunction with the several drawings and the appended claims.

BRIEF DESCRIPTION OF THE DRAWINGS

In describing the various embodiments of the present disclosure, reference is made to the accompanying drawings, which are not necessarily drawn to scale, and wherein.

DETAILED DESCRIPTION OF THE DISCLOSURE

Figure 1:
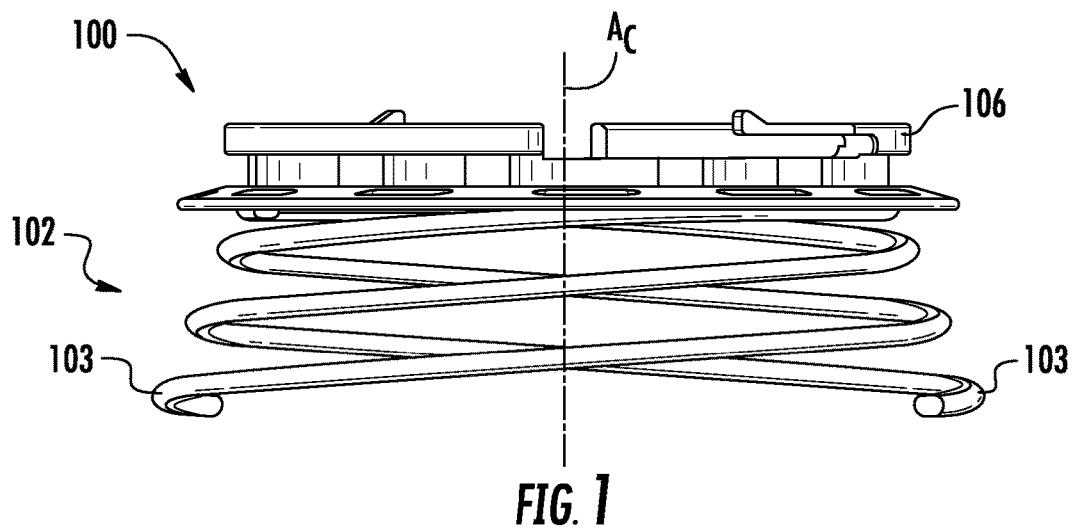
FIG. 1 shows a side view of a portion of an apical connector for securing in a heart wall to facilitate in vivo implantation of a VAD, in accordance with one or more embodiments of the present disclosure.

Various embodiments of the present disclosure provide improved connectors, instruments, and related methods for quickly, safely, and reliably implanting a VAD in a manner that eliminates or reduces the need for cardiopulmonary bypass while also minimizing blood loss. Various aspects of the devices, instruments, and methods disclosed herein build upon those described in the following patent applications, which are incorporated by reference herein in their entirety for all purposes: PCT Application No. PCT/US2015/019308, filed Mar. 6, 2015; PCT Application No. PCT/US2014/028346, filed Mar. 14, 2014; PCT Application No. PCT/US2014/021389, filed Mar. 6, 2014; PCT Application No. PCT/US2013/056952, filed Aug. 28, 2013; U.S. Provisional Application No. 62/127,262, filed Mar. 2, 2015; U.S. Provisional Application No. 61/949,113, filed Mar. 6, 2014; U.S. Provisional Application No. 61/865,908, filed Aug. 14, 2013; U.S. Provisional Application No. 61/859,608, filed Jul. 29, 2013; U.S. Provisional Application No. 61/842,810, filed Jul. 3, 2013; U.S. Provisional Application No. 61/793,643, filed Mar. 15, 2013; U.S. application Ser. No. 13/842,578, filed Mar. 15, 2013; U.S. application Ser. No. 13/410,670, filed Mar. 2, 2012; U.S. application Ser. No. 13/035,837, filed Feb. 25, 2011; U.S. application Ser. No. 12/945,890, filed Nov. 14, 2010; U.S. application Ser. No. 12/590,864, filed Nov. 15, 2009; and U.S. application Ser. No. 12/590,863, filed Nov. 15, 2009. As will be appreciated by one of ordinary skill in the art, identical or similar terminology may be used herein to describe connectors, instruments, methods, structural features, and functional aspects similar to those described in these applications. Moreover, certain similarities will be apparent upon comparison of the drawings of the present disclosure and those of these applications, even though different terminology may be used.

Embodiments of the present disclosure are described herein below with reference to the accompanying drawings, in which some, but not all, embodiments are shown. Indeed, the connectors, instruments, and methods disclosed may be embodied in many different forms and should not be construed as limited to the embodiments set forth herein; rather, these embodiments are provided so that this disclosure is thorough and complete and fully conveys the scope of the connectors, instruments, and methods to those skilled in the art. Like reference numbers refer to like elements throughout. The singular forms "a," "an," and "the" can refer to plural instances unless the context clearly dictates otherwise or unless explicitly stated.

The embodiments of the present disclosure provide improved connectors, instruments, and related methods for quickly, safely, and reliably implanting a VAD. Various aspects of the embodiments allow the VAD to be implanted in a manner that eliminates or reduces the need for cardiopulmonary bypass. Various aspects of the embodiments allow the VAD to be implanted while minimizing blood loss. Although the disclosed connectors and instruments are particularly advantageous for implanting a VAD in a heart wall, it will be appreciated that the connectors and instruments alternatively may be used in other tissue walls of the body for other procedures to provide similar benefits including, but not limited to, valve replacement and repair. Such alternative uses are described in part in the applications listed above.

In one aspect, an apical connector is provided for use in a heart wall. The apical connector may include a port defining an aperture therethrough, an anchoring device extending distally from the port and configured for advancing at least partially through the heart wall, and a cannula configured for advancing through the aperture of the port and at least partially through the heart wall. The cannula may include a locking tab configured to engage the port and lock the cannula with respect to the port.

In some embodiments, the locking tab may be offset from a proximal end of the cannula and may extend along an outer circumferential surface of the cannula. In some embodiments, the cannula may further include a partial flange, and the locking tab may extend from the partial flange. In some embodiments, the locking tab may be configured to deflect from a natural position to a biased position with respect to the partial flange. In some embodiments, the port may include a recess defined in a proximal end of the port and configured to receive the locking tab and the partial flange of the cannula. In some embodiments, the port may further include an undercut groove in communication with the recess and configured to receive the locking tab and the partial flange of the cannula upon rotation of the cannula with respect to the port. In some embodiments, the port may further include a locking protrusion configured to deflect the locking tab of the cannula from the natural position to the biased position upon rotation of the cannula with respect to the port in a first direction.

In some embodiments, the cannula may further include an elastomer covering molded over a proximal portion of the cannula. In some embodiments, the cannula may further include a plurality of engagement recesses defined in a proximal end of the cannula, and the elastomer covering may extend partially over each of the engagement recesses. In some embodiments, the anchoring device may include a plurality of coils offset from one another and arranged in a generally symmetric manner about a central axis of the apical connector such that the coils follow separate helical paths in the heart wall. In some embodiments, the apical connector my further include a sewing ring extending radially outward from the port and configured for suturing to the heart wall. In some embodiments, the apical connector my further include a valve positioned within the cannula and configured for controlling fluid communication therethrough.

In another aspect, an apical connector is provided for use in a heart wall. The apical connector may include a port defining an aperture therethrough, and an anchoring device extending distally from the port and configured for advancing at least partially through the heart wall. The anchoring device may include a plurality of coils offset from one another and arranged in a generally symmetric manner about a central axis of the apical connector such that the coils follow separate helical paths in the heart wall.

In some embodiments, distal ends of the coils may be equally spaced apart from one another in a circumferential direction with respect to the central axis of the apical connector. In some embodiments, each of the coils may be attached to the port at an attachment point, and the attachments points may be equally spaced apart from one another in a circumferential direction with respect to the central axis of the apical connector. In some embodiments, the plurality of coils may include two coils, and distal ends of the two coils may be spaced apart from one another by approximately 180 degrees in a circumferential direction with respect to the central axis of the apical connector. In some embodiments, each of the two coils may be attached to the port at an attachment point, and the attachments points may be spaced apart from one another by approximately 180 degrees in a circumferential direction with respect to the central axis of the apical connector. In some embodiments, each of the coils may have a radially expanding shape such that a helical diameter of the coil increases from a proximal end to a distal end of the coil.

In still another aspect, an apical connector is provided for use in a heart wall. The apical connector may include a port defining an aperture therethrough, a sewing ring extending radially outward from the port and configured for suturing to the heart wall, and an anchoring device extending distally from the port and configured for advancing at least partially through the heart wall. The anchoring device may include a coil.

In another aspect, an apical connector is provided for use in a heart wall. The apical connector may include a port defining an aperture therethrough, a primary anchoring device extending distally from the port and configured for advancing at least partially through the heart wall, and a secondary anchoring device configured for advancing at least partially through the heart wall. At least a portion of the secondary anchoring device may be positioned radially outward from the primary anchoring device.

In some embodiments, the primary anchoring device may include a coil. In some embodiments, the primary anchoring device may be rigidly attached to the port. In some embodiments, the secondary anchoring device may include one or more tissue anchors configured to extend through mating apertures defined in the port. In some embodiments, the one or more tissue anchors may include one or more coils. In some embodiments, the one or more tissue anchors may include one or more pins, prongs, barbs, hooks, or staples. In some embodiments, the secondary anchoring device may include a collar and one or more tissue anchors attached to the collar. In some embodiments, the one or more tissue anchors may include one or more partial coils. In some embodiments, the collar may be configured to attach to the port. In some embodiments, the collar may include a tab, and the port may include a groove configured to receive the tab.

In still another aspect, an apical connector is provided for use in a heart wall. The apical connector may include a port defining an aperture therethrough, an anchoring device extending distally from the port and configured for advancing at least partially through the heart wall, and a cannula configured for advancing through the aperture of the port and at least partially through the heart wall. The cannula may include a plurality of tabs configured to engage the port and lock the cannula with respect to the port.

In some embodiments, the tabs may be arranged in a circumferential array along an outer circumferential surface of the cannula. In some embodiments, the port may include a pawl configured to selectively engage the tabs of the cannula. In some embodiments, the pawl may be configured to deflect away from a natural position when the pawl engages the tabs of the cannula such that the pawl and the tabs form a ratchet mechanism. In some embodiments, the cannula may include male threads, and the port may include female threads configured to engage the male threads of the cannula.

In another aspect, an instrument is provided for coring a hole in a heart wall and attaching a cannula to a port of an apical connector. The instrument may include a main handle, a shaft attached to the main handle, an anvil movably attached to the shaft and configured to move from an insertion position to a coring position, a coring handle positioned over at least a portion of the shaft, a cannula interface attached to the coring handle and configured for removably attaching to the cannula of the apical connector, and a coring tube attached to the coring handle and configured for coring the hole in the heart wall. The coring handle may be configured to translate and rotate with respect to the main handle.

In some embodiments, the coring tube may extend distally beyond the cannula interface. In some embodiments, the cannula interface may be rigidly attached to the coring handle. In some embodiments, the coring tube may be rigidly attached to the coring handle. In some embodiments, the main handle may include a plurality of indicators that correspond to a distance between a distal end of the coring tube and a proximal end of the anvil.

In still another aspect, an instrument is provided for coring a hole in a heart wall and attaching a cannula to a port of an apical connector. The instrument may include a handle, a cannula interface attached to the handle and configured for removably attaching to the cannula of the apical connector, a coring tube rigidly attached to the handle and configured for coring the hole in the heart wall, and a coring anchor rigidly attached to the handle and configured for providing counter-traction for advancing the coring tube into the heart wall.

In some embodiments, the coring anchor may include a coil configured for advancing at least partially through the heart wall. In some embodiments, the coring anchor may extend distally beyond the coring tube. In some embodiments, the coring tube may extend distally beyond the cannula interface. In some embodiments, the cannula interface may be rigidly attached to the handle.

In another aspect, instrument system is provided for securing a port of an apical connector to a heart wall, coring a hole in the heart wall, and attaching a cannula to the port of the apical connector. The instrument system may include a centering guide configured for attaching to the heart wall, a first instrument configured for advancing over the centering guide to secure the port of the apical connector to the heart wall, and a second instrument configured for advancing over the centering guide to core the hole in the heart wall and attach the cannula to the port of the apical connector.

In some embodiments, the centering guide may include a handle, and a guide anchor attached to the handle and configured for attaching the centering guide to the heart wall. In some embodiments, the guide anchor may include a coil configured for advancing at least partially through the heart wall. In some embodiments, the first instrument may include a handle, and a port interface attached to the handle and configured for removably attaching to the port of the apical connector. In some embodiments, the second instrument may include a handle, a cannula interface attached to the handle and configured for removably attaching to the cannula of the apical connector, and a coring tube attached to the handle and configured for coring the hole in the heart wall.

In still another aspect, an instrument is provided for coring a hole in a heart wall and attaching a cannula to a port of an apical connector. The instrument may include a handle, a shaft attached to the handle and extending distally therefrom, a coring anchor attached to the shaft and extending distally therefrom, a coring sleeve movably positioned over at least a portion of the shaft, a coring tube attached to the coring sleeve and extending distally therefrom, an attachment sleeve movably positioned over at least a portion of the coring sleeve, and a cannula interface attached to the attachment sleeve and extending distally therefrom.

In some embodiments, the coring anchor may include a coil configured for advancing at least partially through the heart wall. In some embodiments, the shaft may be rigidly attached to the handle, the coring anchor may be rigidly attached to the shaft, the coring tube may be rigidly attached to the coring sleeve, and the cannula interface may be rigidly attached to the attachment sleeve. In some embodiments, the instrument may be adjustable between a first configuration and a second configuration, the coring sleeve and the attachment sleeve may be configured to rotate with the handle when the instrument is in the first configuration, and the coring sleeve and the attachment sleeve may be configured to rotate relative to the handle when the instrument is in the second configuration. In some embodiments, the instrument may further include a button configured to selectively maintain the instrument in the first configuration.

In another aspect, an instrument is provided for coring a hole in a heart wall and attaching a cannula to a port of an apical connector. The instrument may include a handle, a shaft attached to the handle and extending distally therefrom, a coring anchor attached to the shaft and extending distally therefrom, a sleeve movably positioned over at least a portion of the shaft, a cannula interface attached to the sleeve and extending distally therefrom, and a coring tube attached to the sleeve and extending distally therefrom.

In some embodiments, the coring anchor may include a coil configured for advancing at least partially through the heart wall. In some embodiments, the shaft may be rigidly attached to the handle, the coring anchor may be rigidly attached to the shaft, and the coring tube may be rigidly attached to the attachment sleeve. In some embodiments, the instrument may be adjustable between a first configuration and a second configuration, the sleeve may be configured to rotate with the handle when the instrument is in the first configuration, and the sleeve may be configured to translate and rotate relative to the handle when the instrument is in the second configuration. In some embodiments, the instrument may further include a button configured to selectively maintain the instrument in the first configuration.

In still another aspect, an instrument system is provided for securing a port of an apical connector to a heart wall, coring a hole in the heart wall, and attaching a cannula to the port of the apical connector. The instrument system may include a first instrument configured to secure the port of the apical connector to the heart wall, and a second instrument configured for advancing through the first instrument to core the hole in the heart wall and attach the cannula to the port of the apical connector.

In some embodiments, the first instrument may include a handle, and a port interface attached to the handle and configured for removably attaching to the port of the apical connector. In some embodiments, the second instrument may include a handle, a shaft attached to the handle, a coring anchor attached to the shaft and configured for coring the hole in the heart wall, a sleeve movably positioned over at least a portion of the shaft, a cannula interface attached to the sleeve and configured for removably attaching to the cannula of the apical connector, and a coring anchor attached to the sleeve and configured for providing counter-traction for advancing the coring tube into the heart wall. In some embodiments, the second instrument may be adjustable between a first configuration and a second configuration, the sleeve may be configured to rotate with the handle when the second instrument is in the first configuration, and the sleeve may be configured to translate and rotate relative to the handle when the second instrument is in the second configuration. In some embodiments, the second instrument may further include a button configured to selectively maintain the second instrument in the first configuration.

In another aspect, an instrument is provided for stabilizing an apical connector secured in a heart wall. The instrument may include a handle, and a connector interface attached to a distal end of the handle. The connector interface may include a pair of prongs defining an opening configured for receiving a portion of the connector therebetween, and a protrusion configured for engaging a mating engagement feature of the connector.

In some embodiments, the prongs may have a C-shaped configuration for receiving the portion of the connector therebetween. In some embodiments, the protrusion may be positioned about an intersection of the prongs. In some embodiments, the protrusion may be aligned with a center of the connector interface. In some embodiments, one or more portions of the instrument may be formed of a pliable material.

In still another aspect, an instrument is provided for allowing inspection of a ventricle of a heart through an apical connector secured in a heart wall. The instrument may include a tube defining an aperture therethrough, the tube configured for inserting at least partially through the apical connector and at least partially through the heart wall, and a proximal flange attached to the tube, the proximal flange configured for abutting a proximal end of the apical connector.

In another aspect, a method is provided for inspecting a ventricle of a heart through an apical connector secured in a heart wall, the apical connector including a cannula and a valve disposed within the cannula. The method may include the steps of opening the valve of the apical connector, and inspecting the ventricle through the cannula of the apical connector.

In some embodiments, the step of opening the valve of the apical connector may include inserting an instrument at least partially within the cannula. In some embodiments, the instrument may include a tube defining an aperture therethrough, and a proximal flange attached to the tube. In some embodiments, the step of inserting the instrument at least partially within the cannula may include inserting the tube at least partially within the cannula. In some embodiments, the step of inspecting the ventricle through the cannula of the apical connector may include inspecting the ventricle through the tube.

Apical Connectors

PCT Application No. PCT/US2014/028346 (the '346 Application) describes various embodiments of a connector configured for implanting and using in a tissue wall to establish, maintain, control, and close a fluid communication between opposing surfaces of the tissue wall. As described, the connector specifically may be used as an apical connector in a heart wall at or near the apex of the left ventricle to facilitate in vivo implantation of a VAD and its attachment to the heart. According to certain embodiments, the connector may include an anchoring device, a port, and a coupler device, as described in the '346 Application. The anchoring device may be configured for advancing at least partially into the heart wall to secure the connector thereto for subsequent implantation of the VAD. The port may be attached to a proximal end of the anchoring device and may define an aperture therethrough. In this manner, upon advancing a distal end of the anchoring device at least partially into the heart wall, the port may be positioned against the heart wall such that the aperture provides access to the heart wall. The coupler device may be positioned about or integrated into the port and may be configured for coupling an inlet tube of the VAD to the connector after positioning the inlet tube at least partially through the heart wall and in communication with the ventricle. In certain embodiments, such as those described with respect to FIGS. 4A-4I of the '346 Application, the connector also may include a cannula having a hemostasis valve configured for controlling blood flow through the connector during the VAD implantation procedure.

Referring now to the drawings of the present disclosure, FIG. 1 illustrates an embodiment of a portion of an apical connector 100 (which also may be referred to as a "heart connector" or a "tissue connector") configured for securing in a heart wall (which also may be referred to as a "tissue wall") to facilitate in vivo implantation of a VAD and its attachment to the heart. The connector 100 may include an anchoring device 102 and a port 106 attached to the anchoring device 102, as shown, which features may correspond generally to those described with respect to the various embodiments of the '346 Application, although certain differences are described herein below. It will be appreciated that the connector 100 also may include other features, such as a coupler device and/or a cannula having a hemostasis valve, configured in a manner similar to those described with respect to the various embodiments of the '346 Application. For example, the connector 100 may include the cannula 470 described below.

The anchoring device 102 may include a plurality of helical coils 103 positioned about a central axis $A_C$ of the connector 100 and configured for advancing at least partially into the heart wall along respective helical paths defined by the coils 103. For example, as shown in FIG. 1, the anchoring device 102 may include two coils 103 that are offset from one another and arranged in a generally symmetric manner about the central axis $A_C$ of the connector 100. In particular, the two coils 103 may be attached to the port 106 at attachment points that are spaced apart from one another, for example, by 180-degrees in a circumferential direction with respect to the central axis $A_C$ of the connector 100. The tips (i.e., the distal ends) of the two coils 103 also may be spaced apart from one another, for example, by 180-degrees in a circumferential direction with respect to the central axis $A_C$ of the connector 100. In this manner, the two coils 103 may follow separate, opposing helical paths in the myocardial wall. In other embodiments, the anchoring device 102 may include three or more coils 103 that are offset from one another and arranged in a generally symmetric manner about the central axis $A_C$ of the connector 100, such that the coils 103 follow separate helical paths in the myocardial wall. The three or more coils 103 may include attachment points and tips that are equally spaced from one another in a circumferential direction with respect to the central axis $A_C$ of the connector 100. In various embodiments, the anchoring device 102 may include two or more coils 103 that are "clocked" (i.e., circumferentially spaced) from each other by 20 degrees, 25 degrees, 30 degrees, 45 degrees, 60 degrees, 90 degrees, or 120 degrees with respect to the central axis $A_C$ of the connector 100. As shown, the coils 103 may have a radially-expanding helical shape (i.e., a conical shape) such that a helical diameter of the coil 103 increases from the proximal end to the distal end of the coil 103. Due to the radially-expanding helical shape, the coils 103 may be configured to compress at least a portion of the heart wall inward toward the central axis $A_C$ of the connector 100 when the anchoring device 102 is advanced through the heart wall. It will be appreciated from the description herein that the anchoring device 102 may include other anchoring mechanisms (other than coils) common in the surgical field, such as clips, staples, and screws. In some embodiments, the anchoring device 102 may include a combination of different anchoring mechanisms.

As compared to embodiments in which the anchoring device 102 includes only a single coil 103, the plurality of coils 103 of the foregoing embodiments may improve stability of the port 106 as well as the overall connector 100 when secured in the heart wall. In particular, the plurality of coils 103 may provide balanced engagement of the heart wall and prevent the port 106 from lifting off of the heart wall (opposite the coil insertion point), as may be experienced with a single coil configuration of the anchoring device 102. As will be appreciated, the plurality of coils 103 may enhance initial starting and advancing of the anchoring device 102 in the heart wall in a manner similar to that of a multi-start threadform. Additionally, as compared to a single coil configuration, the coils 103 may be shorter, resulting in increased rigidity of the coils 103, which may improve implantation consistency as well as full engagement feedback as the anchoring device 102 is secured in the heart wall. Further, the balanced engagement provided by the plurality of coils 103 may improve hemostasis achieved upon implantation of the connector 100, for example by ensuring balanced contact between the port 106 and the heart wall, or between an additional sealing element of the connector 100 and the heart wall.

Figure 2:
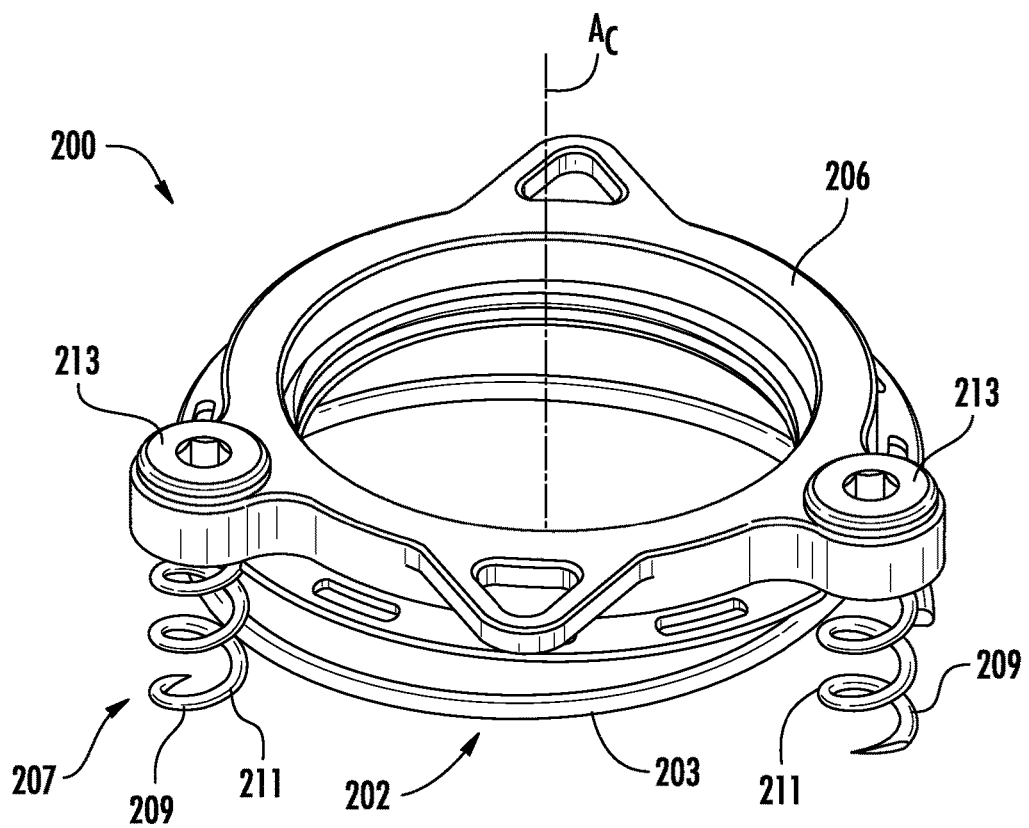
FIG. 2 shows a perspective view of a portion of an apical connector for securing in a heart wall to facilitate in vivo implantation of a VAD, in accordance with one or more embodiments of the present disclosure.

FIG. 2 illustrates an embodiment of a portion of an apical connector 200 (which also may be referred to as a "heart connector" or a "tissue connector") configured for securing in a heart wall (which also may be referred to as a "tissue wall") to facilitate in vivo implantation of a VAD and its attachment to the heart. The connector 200 may include a primary anchoring device 202 and a port 206 attached to the primary anchoring device 202, as shown, which features may correspond generally to those described with respect to the various embodiments of the '346 Application, although certain differences are described herein below. It will be appreciated that the connector 200 also may include other features, such as a coupler device and a cannula having a hemostasis valve, configured in a manner similar to those described with respect to the various embodiments of the '346 Application. For example, the connector 200 may include the cannula 470 described below.

The primary anchoring device 202 may include one or more helical coils 203 positioned about a central axis $A_C$ of the connector 200 and configured for advancing at least partially into the heart wall along a helical path defined by the one or more coils 203. For example, as shown in FIG. 2, the primary anchoring device 202 may include a single coil 203. As shown, the coil 203 may have a radially-expanding helical shape such that a helical diameter of the of the coil 203 increases from the proximal end to the distal end of the coil 203. The connector 200 also may include a secondary anchoring device 207 configured for engaging the heart wall. The secondary anchoring device 207 may include one or more tissue anchors 209 configured for extending through mating apertures defined in the port 206 and advancing at least partially into the heart wall. As shown in FIG. 2, each tissue anchor 209 may include a helical coil 211 extending from an anchor head 213 and configured for advancing into the heart wall. Alternatively, each tissue anchor 209 may include a pin, prong, barb, hook, staple, or other similar feature extending from the anchor head 213 and configured for advancing into the heart wall. As shown, the one or more tissue anchors 209 may be positioned radially outward from the primary anchoring device 202 for engaging a separate portion of the heart wall as compared to the portion of the heart wall engaged by the primary anchoring device 202.

As compared to embodiments including only the primary anchoring device 202, the additional secondary anchoring device 207 may improve stability of the port 206 as well as the overall connector 200 when secured in the heart wall. In particular, the one or more tissue anchors 209 may provide balanced engagement of the heart wall and prevent the port 206 from lifting off of the heart wall, as may be experienced with a connector including only a primary anchoring device having a single coil configuration. The secondary anchoring device 207 may be configured as a locking mechanism, for example, to prevent the primary anchoring device 202 from rotating out of the tissue of the heart wall. Additionally, as compared to a connector including only a primary anchoring device having a single coil configuration, the coil 203 of the primary anchoring device 202 may be shorter, resulting in increased rigidity of the coil 203, which may improve implantation consistency as well as full engagement feedback as the primary anchoring device 202 is secured in the heart wall. Further, the balanced engagement provided by the one or more tissue anchors 209 in combination with the primary anchoring device 202 may improve hemostasis achieved upon implantation of the connector 200, for example by ensuring balanced contact between the port 206 and the heart wall, or between an additional sealing element of the connector 200 and the heart wall. It will be appreciated that the connector 200 may include a variety and number of anchoring devices, which may include one or more coils, clips, staples, screws, or other anchoring mechanisms. In some embodiments, the secondary anchoring device 207 may include one or more coils having a different configuration than one or more coils of the primary anchoring device 202. For example, the one or more coils of the primary anchoring device 202 and the one or more coils of the secondary anchoring device 207 may have different pitches, coil lengths, diameters, taper angles, etc.

Figure 3:
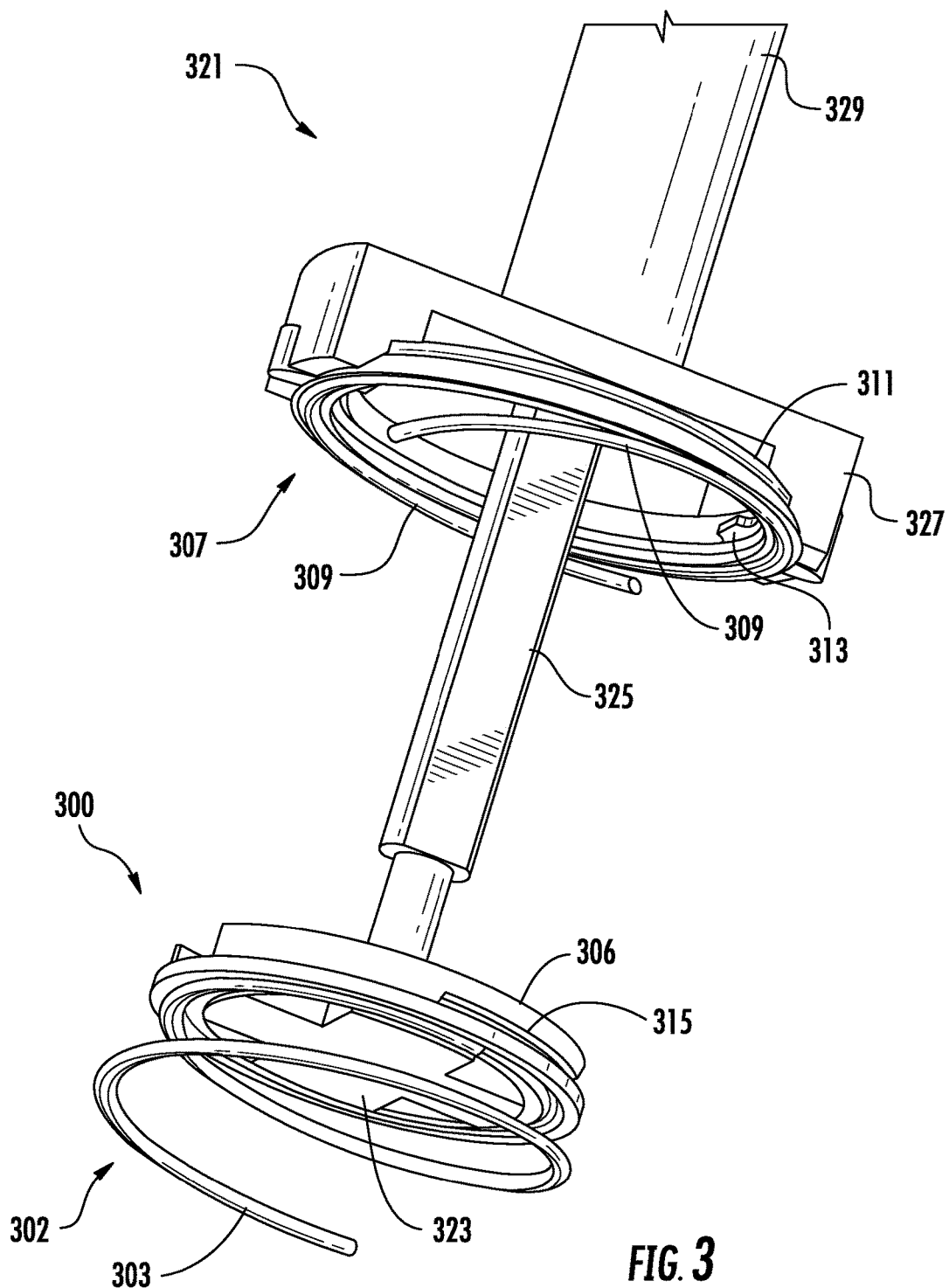
FIG. 3 shows a perspective view of a portion of an apical connector and a delivery instrument for securing the apical connector in a heart wall to facilitate in vivo implantation of a VAD, in accordance with one or more embodiments of the present disclosure.

FIG. 3 illustrates an embodiment of a portion of an apical connector 300 (which also may be referred to as a "heart connector" or a "tissue connector") configured for securing in a heart wall (which also may be referred to as a "tissue wall") to facilitate in vivo implantation of a VAD and its attachment to the heart. The connector 300 may include a primary anchoring device 302 and a port 306 attached to the primary anchoring device 302, as shown, which features may correspond generally to those described with respect to the various embodiments of the '346 Application, although certain differences are described herein below. It will be appreciated that the connector 300 also may include other features, such as a coupler device and a cannula having a hemostasis valve, configured in a manner similar to those described with respect to the various embodiments of the '346 Application. For example, the connector 200 may include the cannula 470 described below.

The primary anchoring device 302 may include one or more helical coils 303 positioned about a central axis $A_C$ of the connector 300 and configured for advancing at least partially into the heart wall along a helical path defined by the one or more coils 303. For example, as shown in FIG. 3, the primary anchoring device 302 may include a single coil 303. As shown, the coil 303 may have a radially-expanding helical shape such that a helical diameter of the of the coil 303 increases from the proximal end to the distal end of the coil 303. The connector 300 also may include a secondary anchoring device 307 configured for engaging the heart wall. The secondary anchoring device 307 may include one or more tissue anchors 309 attached to and extending from a common collar 311 and configured for advancing at least partially into the heart wall. Each tissue anchor 309 may include a partial helical coil extending from the collar 311, as shown in FIG. 3. Alternatively, each tissue anchor 309 may include a pin, prong, barb, hook, staple, or other similar feature extending from the collar 311 and configured for advancing into the heart wall. As shown, the one or more tissue anchors 309 may be positioned radially outward from the primary anchoring device 302 for engaging a separate portion of the heart wall as compared to the portion of the heart wall engaged by the primary anchoring device 302. In some embodiments, the collar 311 may be configured to attach to and lock onto the port 306 upon advancing the one or more tissue anchors 309 into the heart wall. As shown, the collar 311 may include one or more tabs 313, and the port 306 may include one or more grooves 315 defined in an outer surface of the port 306 and configured to receive the one or more tabs 313. Upon advancing the one or more tissue anchors 309 into the heart wall via rotation of the collar 311, the one or more tabs 313 may be received within the one or more grooves 315, thereby locking the collar 311 with respect to the port 306. In this manner, the tabs 313 and the grooves 315 may form a partial-turn locking mechanism, such as a half-turn locking mechanism. Alternatively, the collar 311 and the port 306 may include mating threads or other features for attaching and locking the collar 311 relative to the port 306.

As compared to embodiments including only the primary anchoring device 302, the additional secondary anchoring device 307 may improve stability of the port 306 as well as the overall connector 300 when secured in the heart wall. In particular, the one or more tissue anchors 309 and the collar 311 may provide balanced engagement of the heart wall and prevent the port 306 from lifting off of the heart wall, as may be experienced with a connector including only a primary anchoring device having a single coil configuration. Additionally, as compared to a connector including only a primary anchoring device having a single coil configuration, the coil 303 of the primary anchoring device 302 may be shorter, resulting in increased rigidity of the coil 303, which may improve implantation consistency as well as full engagement feedback as the primary anchoring device 302 is secured in the heart wall. Further, the balanced engagement provided by the one or more tissue anchors 309 and the collar 311 may improve hemostasis achieved upon implantation of the connector 300, for example by ensuring balanced contact between the port 306 and the heart wall, or between an additional sealing element of the connector 300 and the heart wall.

FIG. 3 also illustrates a delivery instrument 321 for securing the apical connector 300 in the heart wall. The delivery instrument 321 may include a port engaging/driving portion 323 (which also may be referred to as a "port interface") attached to a shaft 325 and configured for engaging and driving the port 306 for advancing the primary anchoring device 302 into the heart wall. The delivery instrument 321 also may include a collar engaging/driving portion 327 (which also may be referred to as a "collar interface") attached to a cannulated sleeve 329 and configured for engaging and driving the collar 311 for advancing the secondary anchoring device 307 into the heart wall in a concentric manner about the port 306. The shaft 325 and the cannulated sleeve 329 may be configured to translate and rotate with respect to one another. In this manner, the shaft 325 and the port engaging/driving portion 323 may be used to advance the primary anchoring device 302 into the heart wall, and then the cannulated sleeve 329 and the collar engaging/driving portion 327 may be used to advance the secondary anchoring device 307 into the heart wall and to attach the collar 311 to the port 306.

Figure 4A:
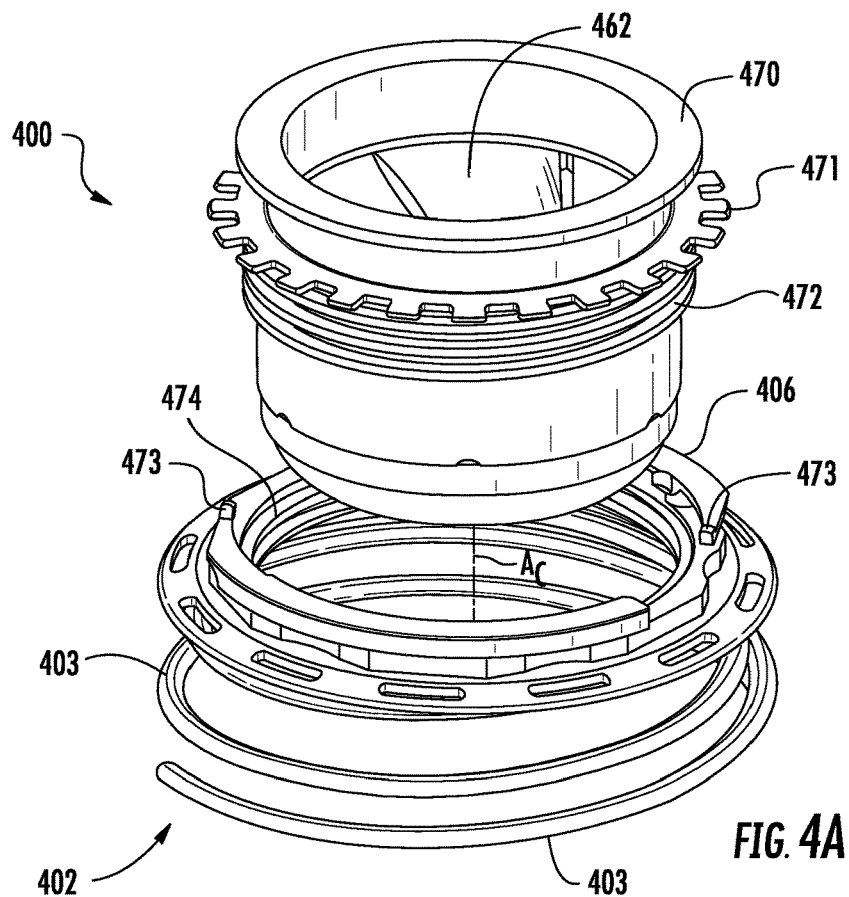
FIGS. 4A and 4B show perspective views of a portion of an apical connector for securing in a heart wall to facilitate in vivo implantation of a VAD, in accordance with one or more embodiments of the present disclosure.
Figure 4B:
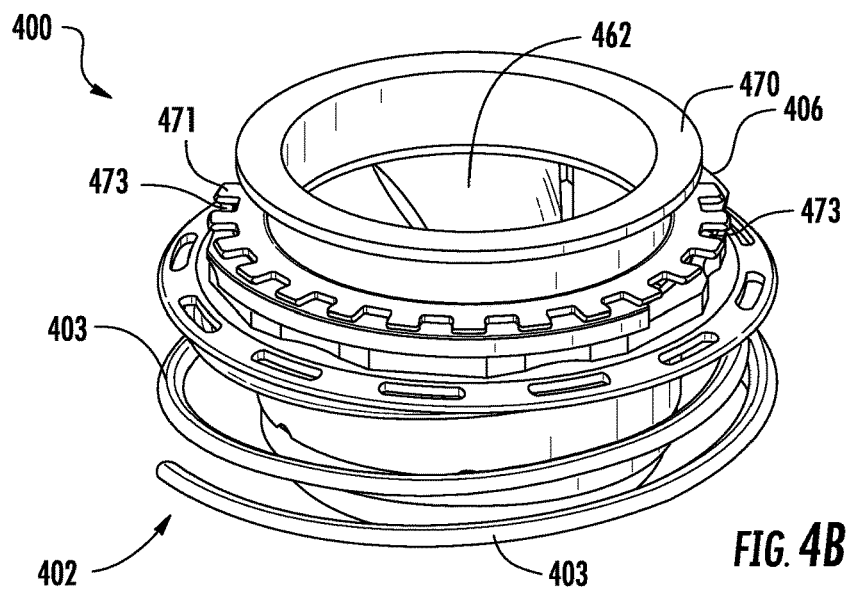

FIGS. 4A and 4B illustrate an embodiment of a portion of an apical connector 400 (which also may be referred to as a "heart connector" or a "tissue connector") configured for securing in a heart wall (which also may be referred to as a "tissue wall") to facilitate in vivo implantation of a VAD and its attachment to the heart. The connector 400 may include an anchoring device 402 including one or more helical coils 403, a port 406 attached to the anchoring device 402, and a cannula 470 having a hemostasis valve 462, as shown, which features may correspond generally to those described with respect to the various embodiments of the '346 Application, although certain differences are described herein below. It will be appreciated that the connector 400 also may include other features, such as a coupler device, configured in a manner similar to those described with respect to the various embodiments of the '346 Application.

The cannula 470 may include a plurality of tabs 471 positioned at or near the proximal end of the cannula 470 and extending radially outward. In particular, the tabs 471 may be arranged in a circumferential array extending from the outer surface of the cannula 470, as shown in FIGS. 4A and 4B. The cannula 470 also may include male threads 472 formed along the outer surface of the cannula 470 and positioned distally with respect to the tabs 471. The port 406 may include one or more pawls 473 positioned at or near the proximal end of the port 406 and extending along the circumference thereof. The port 406 also may include female threads 474 formed along the inner surface of the port 406 and positioned distally with respect to the pawls 473. The threads 472 of the cannula 470 may engage the threads 474 of the port 406 as the cannula 470 is inserted through the aperture of the port 406 and rotated with respect to the port 406. The pawls 473 may be resilient or spring-like and configured to deflect away from a natural position when a biasing force is applied thereto via the tabs 471 as the cannula 470 threadably engages the port 406. In this manner, the tabs 471 of the cannula 470 and the one or more pawls 473 of the port 406 may form a ratchet mechanism as the one or more pawls 473 selectively engage the tabs 471. The ratchet mechanism may prevent the cannula 470 from being unthreaded from the port 406 unless the pawls 473 are biased by a user to disengage the tabs 471.

As compared to some other connector embodiments, the ratchet mechanism of the connector 400 provides a means for locking the cannula 470 to the port 406, which may improve the structural integrity of connector as well as the hemostasis achieved upon implantation of the connector 400. Moreover, the ratchet mechanism provides tactile feedback as the cannula 470 is attached to the port 406.

Figure 5A:
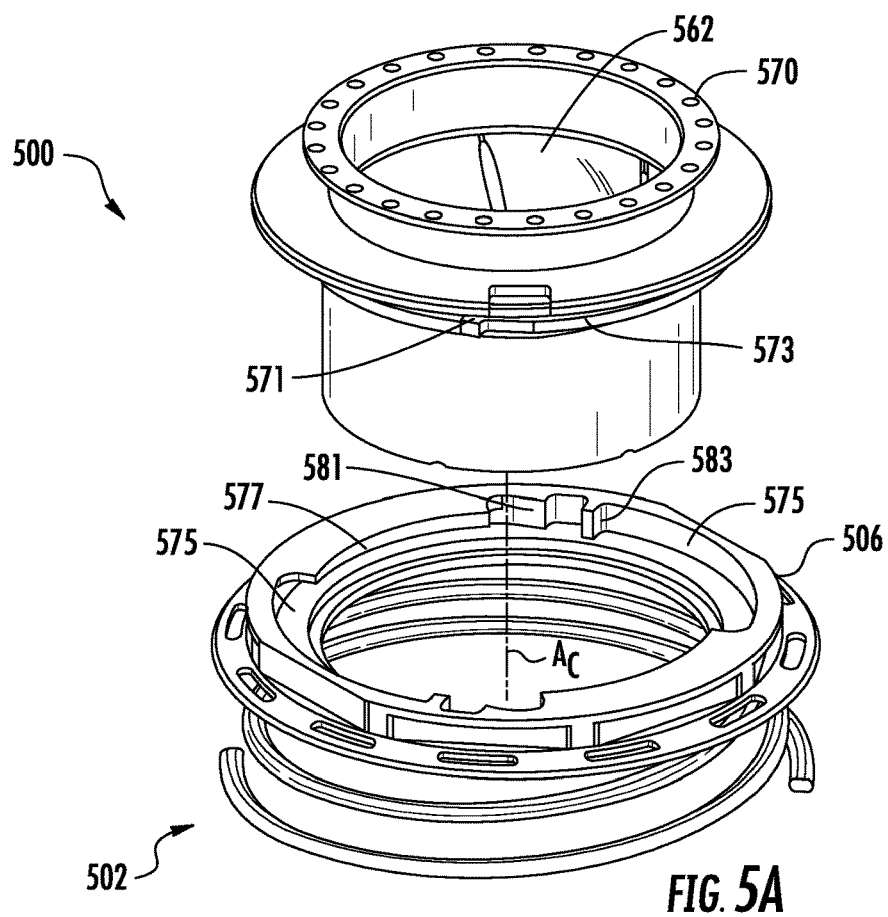
FIGS. 5A and 5B show perspective views of a portion of an apical connector for securing in a heart wall to facilitate in vivo implantation of a VAD, in accordance with one or more embodiments of the present disclosure.
Figure 5B:
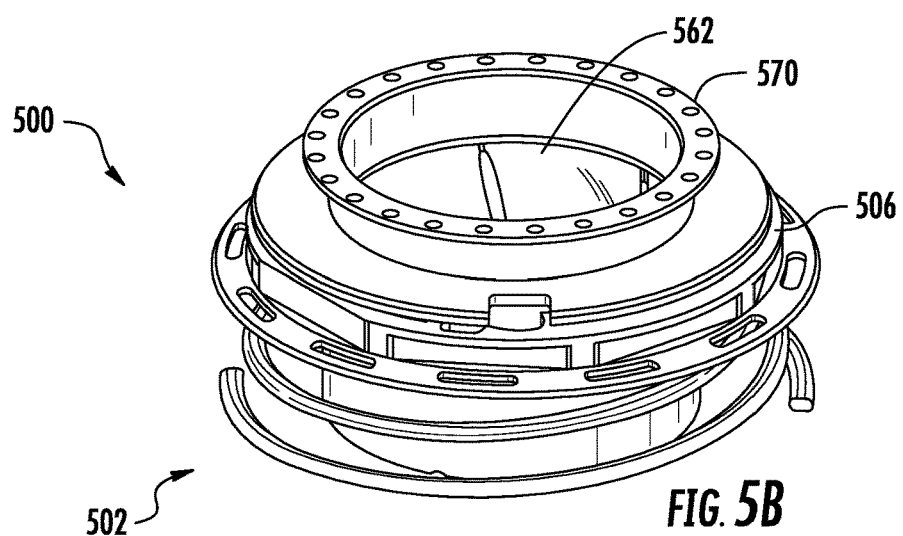

FIGS. 5A and 5B illustrate an embodiment of a portion of an apical connector 500 (which also may be referred to as a "heart connector" or a "tissue connector") configured for securing in a heart wall (which also may be referred to as a "tissue wall") to facilitate in vivo implantation of a VAD and its attachment to the heart. The connector 500 may include an anchoring device 502, a port 506 attached to the anchoring device 502, and a cannula 570 having a hemostasis valve 562, as shown, which features may correspond generally to those described with respect to the various embodiments of the '346 Application, although certain differences are described herein below. It will be appreciated that the connector 500 also may include other features, such as a coupler device, configured in a manner similar to those described with respect to the various embodiments of the '346 Application.

The cannula 570 may include one or more locking members 571 positioned near the proximal end of the cannula 570 and extending along the outer circumference thereof. Each locking member 571 may extend from a partial flange 573 of the cannula 570 and may be resilient or spring-like and configured to deflect radially inward from a natural position when a biasing force is applied thereto via mating features of the port 506 as the cannula 570 is attached to the port 506. The port 506 may include one or more recesses 575 defined about the proximal end of the port 506 and configured to allow the locking members 571 and the partial flanges 573 to be inserted axially therein. The port 506 also may include one or more undercut grooves 577 defined near the proximal end of the port 506 and extending along the inner circumference thereof. Each undercut groove 577 may be positioned adjacent to and in communication with one of the recesses 575. The undercut grooves 577 may be configured to receive the locking members 571 and the partial flanges 573 of the cannula 570 upon rotation of the cannula 570 with respect to the port 506. The port 507 further may include one or more locking protrusions 581 and one or more stop protrusions 583. The locking protrusions 581 may be configured to deflect the locking members 571 of the cannula 570 radially inward upon rotation of the cannula 570 with respect to the port 506 in a first direction, and the stop protrusions 583 may be configured to contact the locking members 571 and limit rotation of the cannula 570 with respect to the port 506 in the first direction. The locking members 571 may be configured to return to their natural position after advancing past the locking protrusions 581 and prevent rotation of the cannula 570 with respect to the port 506 in an opposite second direction. In this manner, the mating features of the cannula 570 and port 506 may form a partial-turn locking mechanism configured to prevent the cannula 570 from being detached from the port 506 unless the locking members 571 are biased by a user to disengage the locking protrusions 581 and allow rotation of the cannula 570 with respect to the port 506 in the second direction. According to the embodiment shown in FIGS. 5A and 5B, the partial-turn locking mechanism is a half-turn locking mechanism, although other configurations are possible, such as a ⅓-turn or a ¼-turn configuration.

As compared to some other connector embodiments, the partial-turn locking mechanism of the connector 500 provides a means for locking the cannula 570 to the port 506, which may improve the structural integrity of connector as well as the hemostasis achieved upon implantation of the connector 500. Moreover, the partial-turn locking mechanism provides tactile feedback as the cannula 570 is attached to the port 506.

Instruments

The applications listed above describe various embodiments of instruments and instrument systems for securing an apical connector in a heart wall, coring a hole in the heart wall, and/or attaching a cannula to a port of the apical connector. As will be appreciated, the instruments, instrument systems, and related methods disclosed herein may include structural features and functional aspects similar to those described in the applications listed above.

Figure 6A:
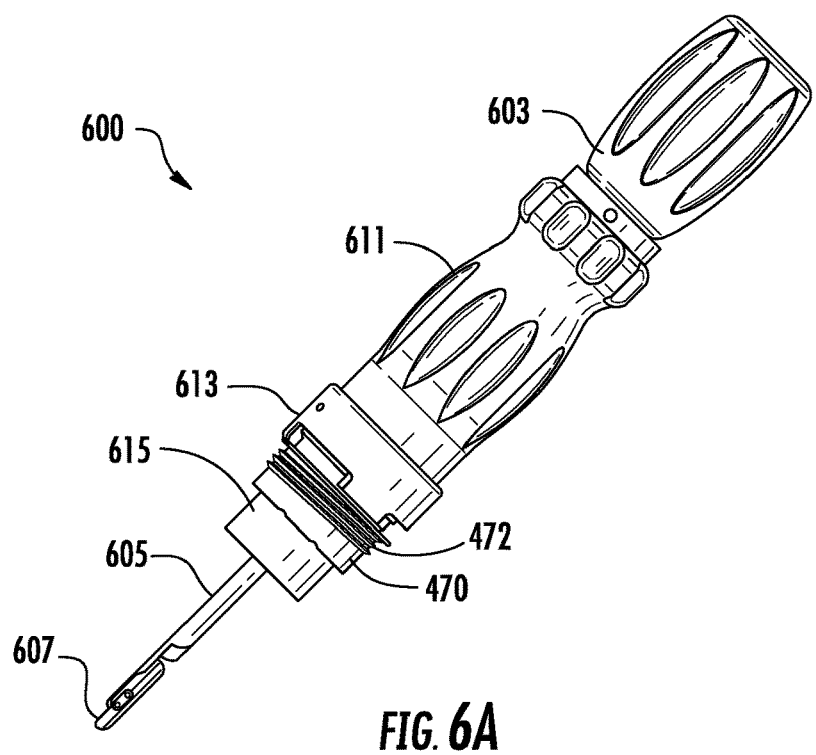
FIGS. 6A and 6B show perspective views of an instrument for coring a hole in a heart wall and attaching a cannula to a port of an apical connector, in accordance with one or more embodiments of the present disclosure.
Figure 6B:
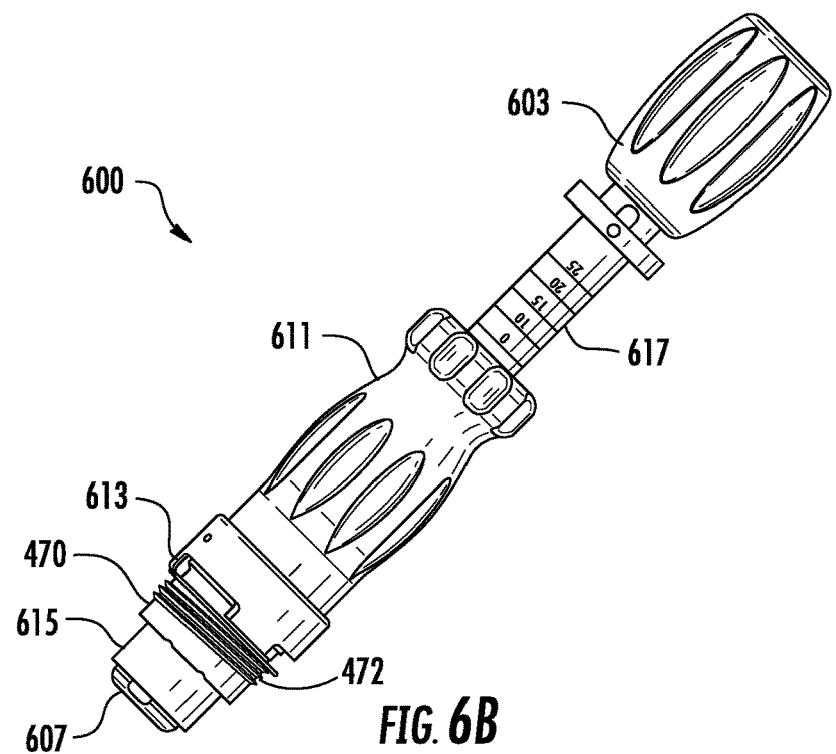

FIGS. 6A and 6B illustrate an embodiment of an instrument 600 for coring a hole in a heart wall (which also may be referred to as a "tissue wall") and attaching a cannula to a port of an apical connector (which also may be referred to as a "heart connector" or a "tissue connector"). The instrument 600 may be configured for use with the apical connector 400 described above, including the valved cannula 470 and the port 406, or any of the other connectors described herein or in the applications listed above.

The instrument 600 may include a main handle 603, a shaft 605 rigidly attached to the main handle 603 and extending distally therefrom, and an anvil 607 movably attached to the distal end of the shaft 605. The anvil 607 may be configured to move with respect to the shaft 605 from an insertion position, as shown in FIG. 6A, to a coring position, as shown in FIG. 6B. In particular, the anvil 607 may be attached to the distal end of the shaft 605 in a manner that allows the anvil 607 to rotate, flip, or pivot from the insertion position to the coring position. When the anvil 607 is in the insertion position, the anvil 607 may extend in line with or parallel to the longitudinal axis of the shaft 605, and when the anvil 607 is in the coring position, the anvil 607 may extend perpendicular to the longitudinal axis of the shaft 605. The instrument 600 also may include a coring handle 611, a cannula interface 613 rigidly attached to the distal end of the coring handle 611, and a coring tube 615 rigidly attached to the coring handle 611 and extending distally beyond the cannula interface 613. The cannula interface 613 may be configured for removably attaching to and retaining a cannula of an apical connector, such as the valved cannula 470 of the apical connector 400, as shown. The coring tube 615 may be configured for contacting the heart wall and coring a hole therein, as described in detail below. The coring handle 611 may be configured for advancing the cannula interface 613 (and the cannula 470 attached thereto) toward the port 406 previously attached to the heart wall via the anchoring device 402, and for advancing the coring tube 615 toward the heart wall and through the aperture of the port 406, as described in detail below. As shown, the coring tube 615 may be configured to extend through and distally beyond the cannula 470 when the cannula 470 is attached to the cannula interface 613. When the cannula 470 is attached to the cannula interface 613, the hemostasis valve 462 may assume an open position and may form a seal against the outer surface of the coring tube 615.

The coring handle 611, the cannula interface 613, and the coring tube 615 may be cannulated and movably positioned over respective portions of the main handle 603 and the shaft 605. In particular, the coring handle 611, the cannula interface 613, and the coring tube 615 may be configured to translate axially with respect to the main handle 603, the shaft 605, and the anvil 607 from a proximal position, as shown in FIG. 6A, to a distal position, as shown in FIG. 6B. The instrument 600 may be configured such that the anvil 607 assumes the insertion position when the coring handle 611, the cannula interface 613, and the coring tube 615 are in the proximal position, and the anvil 607 returns to the coring position as the coring handle 611, the cannula interface 613, and the coring tube 615 are translated from the proximal position toward the distal position. The coring handle 611, the cannula interface 613, and the coring tube 615 also may be configured to rotate with respect to the main handle 603, the shaft 605, and the anvil 607. The main handle 603 may include a plurality of indicators 617 that correspond to a distance between a distal end (i.e., a coring edge) of the coring tube 615 and a proximal end of the anvil 607 (when the anvil 607 is in the coring position), as the coring handle 611, the cannula interface 613, and the coring tube 615 translate axially with respect to the main handle 603, the shaft 605, and the anvil 607.

The instrument 600 may be used following attachment of the port 406 to the heart wall via the anchoring device 402, as may be achieved with another instrument, such as the delivery tool described in the '346 Application or one of the first instruments 902, 1002, 1202, 1302 described below. An initial incision may be created in the heart wall with a scalpel or other cutting device that is advanced through the aperture of the port 406. Then, with the coring handle 611, the cannula interface 613, and the coring tube 615 in the distal position and the anvil 607 in the insertion position, the anvil 607 may be inserted through the initial incision and into the ventricle of the heart. After insertion into the ventricle, the coring handle 611, the cannula interface 613, and the coring tube 615 may be translated from the proximal position toward the distal position, thereby causing the anvil 607 to move from the insertion position to the coring position. With the anvil 607 in the coring position, the main handle 603 may be drawn toward the user (i.e., moved proximally away from the heart wall) until the anvil 607 engages the inner surface of the heart wall. In this manner, the anvil 607 may act as a "backstop" for controlling the heart wall and providing counter-traction for advancing the coring tube 615 toward and into the heart wall.

The coring handle 611, the cannula interface 613, and the coring tube 615 may be further translated toward the distal position until the distal end of the coring tube 615 contacts the outer surface of the heart wall. At that point, the coring handle 611 may be still further translated toward the distal position and also rotated with respect to the main handle 603, the shaft 605, and the anvil 607. In this manner, the instrument 600 may simultaneously core a hole in the heart wall as the coring tube 615 advances therethrough and attach the valved cannula 470 to the port 406 as the threads 472 of the cannula 470 and the threads 474 of the port 406 engage one another. When the cannula 470 is attached to the port 406, the cannula 470 may be inserted at least partially through the hole formed in the heart wall. After the hole is formed in the heart wall and the cannula 470 is securely attached to the port 406, the cannula interface 613 may be detached from the cannula 470 and the entire instrument 600 may be removed from the heart wall and the connector 400. The coring tube 615 and the anvil 607 may be configured to retain the tissue core removed from the heart wall within the coring tube 615. As the coring tube 615 is removed from the cannula 470, the hemostasis valve 462 may close to prevent blood loss through the connector 400. A VAD then may be implanted in the heart wall via the connector 400. In particular, an inlet tube of the VAD may be inserted at least partially through the cannula 470 and at least partially through the hole in the heart wall such that the inlet tube is in communication with the ventricle of the heart. When the inlet tube is inserted through the cannula 470, the hemostasis valve 462 may assume an open position and may form a seal against the outer surface of the inlet tube.

Figure 7:
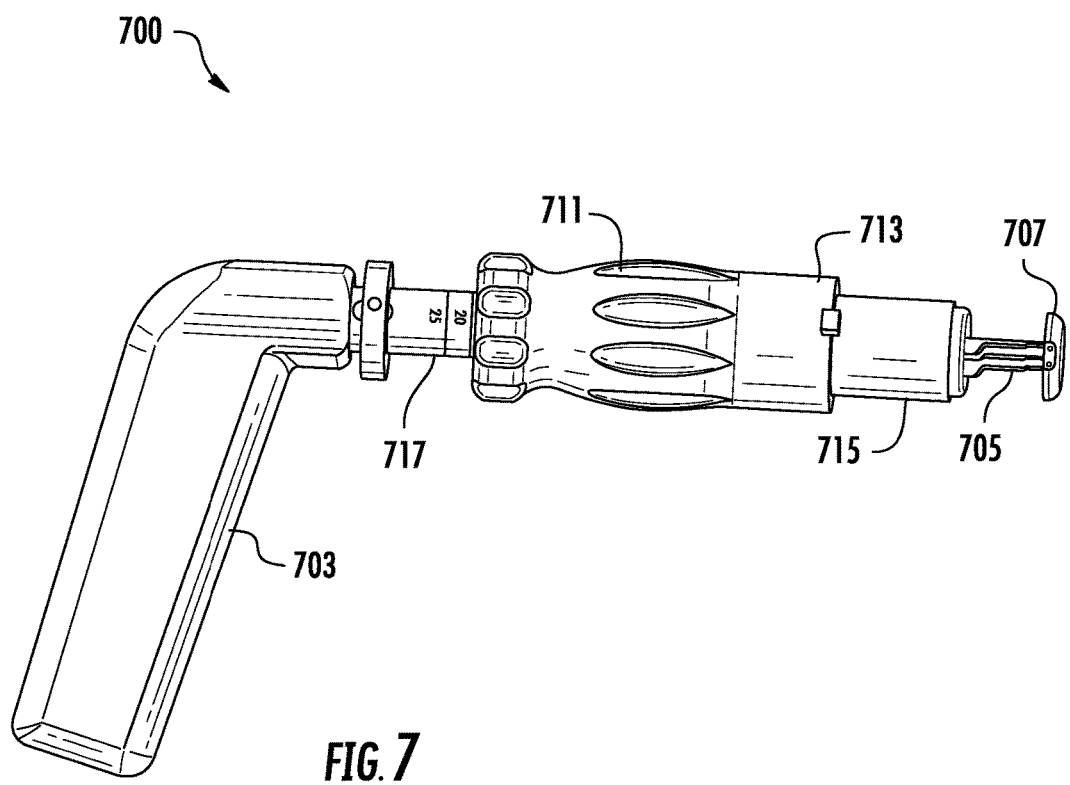
FIG. 7 shows a perspective view of an instrument for coring a hole in a heart wall and attaching a cannula to a port of an apical connector, in accordance with one or more embodiments of the present disclosure.

FIG. 7 illustrates an embodiment of an instrument 700 for coring a hole in a heart wall (which also may be referred to as a "tissue wall") and attaching a cannula to a port of an apical connector (which also may be referred to as a "heart connector" or a "tissue connector"). The instrument 700 may be configured for use with the apical connector 400 described above, including the valved cannula 470 and the port 406, or any of the other connectors described herein or in the applications listed above.

The instrument 700 may include various features corresponding to those described above with respect to the instrument 600, which features are identified in FIG. 7 with corresponding reference numbers. As shown, the instrument 700, may include a main handle 703, a shaft 705, an anvil 707, a coring handle 711, a cannula interface 713, a coring tube 715, and a plurality of indicators 717, which features generally are configured in a similar manner. In contrast to the axial configuration of the main handle 603 of the instrument 600, the main handle 703 of the instrument 700 may have an offset or "pistol-grip" configuration, as shown in FIG. 7. For certain users, the pistol-grip configuration of the main handle 703 may provide improved visibility of the heart wall and the connector and/or improved control of the instrument 700.

Figure 8:
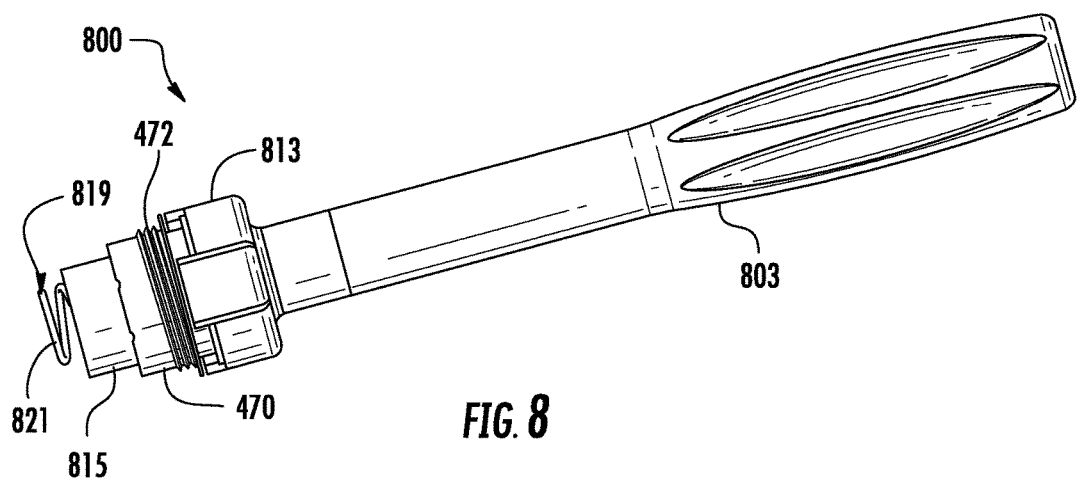
FIG. 8 shows a perspective view of an instrument for coring a hole in a heart wall and attaching a cannula to a port of an apical connector, in accordance with one or more embodiments of the present disclosure.

FIG. 8 illustrates an embodiment of an instrument 800 for coring a hole in a heart wall (which also may be referred to as a "tissue wall") and attaching a cannula to a port of an apical connector (which also may be referred to as a "heart connector" or a "tissue connector"). The instrument 800 may be configured for use with the apical connector 400 described above, including the valved cannula 470 and the port 406, or any of the other connectors described herein or in the applications listed above.

The instrument 800 may include a handle 803 and a cannula interface 813 rigidly attached to the distal end of the handle 803. As shown, the instrument 800 also may include a coring tube 815 rigidly attached to the handle 803 and extending distally beyond the cannula interface 813. The instrument 800 further may include a coring anchor 819 rigidly attached to the handle 803 and extending distally beyond the coring tube 815. The cannula interface 813 may be configured for removably attaching to and retaining a cannula of an apical connector, such as the valved cannula 470 of the apical connector 400, as shown. The coring tube 815 may be configured for contacting the heart wall and coring a hole therein, as described in detail below. When the cannula 470 is attached to the cannula interface 813, the hemostasis valve 462 may assume an open position and may form a seal against the outer surface of the coring tube 815. The coring anchor 819 may be configured for attaching to the heart wall prior to the coring tube 815 contacting the heart wall. As shown, the coring anchor 819 may include one or more helical coils 821 configured for advancing into the heart wall. The one or more coils 821 may have a straight helical shape (i.e., a cylindrical shape) such that a helical diameter of the coil 821 is constant or substantially constant from the proximal end to the distal end of the coil 103. In other embodiments, the coring anchor 819 may include one or more pins, prongs, barbs, hooks, staples, or other similar features configured for advancing into the heart wall.

The instrument 800 may be used following attachment of the port 406 to the heart wall via the anchoring device 402, as may be achieved with another instrument, such as the delivery tool described in the '346 Application or one of the first instruments 902, 1002, 1202, 1302 described below. The distal end of the instrument 800 may be inserted through the aperture of the port 406 until the coring anchor 819 contacts the outer surface of the heart wall. The coring anchor 819 then may be advanced into the heart wall, by axial translation and/or rotation of the handle 803, depending on the type of coring anchor 819 used. For the coiled coring anchor 819 shown, the handle 803 may be rotated and axially translated according to the helical path or paths defined by the one or more coils 821.

As the coring anchor 819 is advanced into the heart wall, the distal end of the coring tube 815 approaches and eventually contacts the outer surface of the heart wall. At this point, the coring anchor 819 may provide counter-traction for advancing the coring tube 815 into the heart wall. As the handle 803 is further rotated and axially translated according to the path of the coiled coring anchor 819, the instrument 800 may simultaneously core a hole in the heart wall as the coring tube 815 advances therethrough and attach the valved cannula 470 to the port 406 as the threads 472 of the cannula 470 and the threads 474 of the port 406 engage one another. When the cannula 470 is attached to the port 406, the cannula 470 may be inserted at least partially through the hole formed in the heart wall. After the hole is formed in the heart wall and the cannula 470 is securely attached to the port 406, the cannula interface 813 may be detached from the cannula 470 and the entire instrument 800 may be removed from the heart wall and the connector 400. The coring tube 815 and the coring anchor 819 may be configured to retain the tissue core removed from the heart wall within the coring tube 815. As the coring tube 815 is removed from the cannula 470, the hemostasis valve 462 may close to prevent blood loss through the connector 400. A VAD then may be implanted in the heart wall via the connector 400. In particular, an inlet tube of the VAD may be inserted at least partially through the cannula 470 and at least partially through the hole in the heart wall such that the inlet tube is in communication with the ventricle of the heart. When the inlet tube is inserted through the cannula 470, the hemostasis valve 462 may assume an open position and may form a seal against the outer surface of the inlet tube.

Figure 9A:
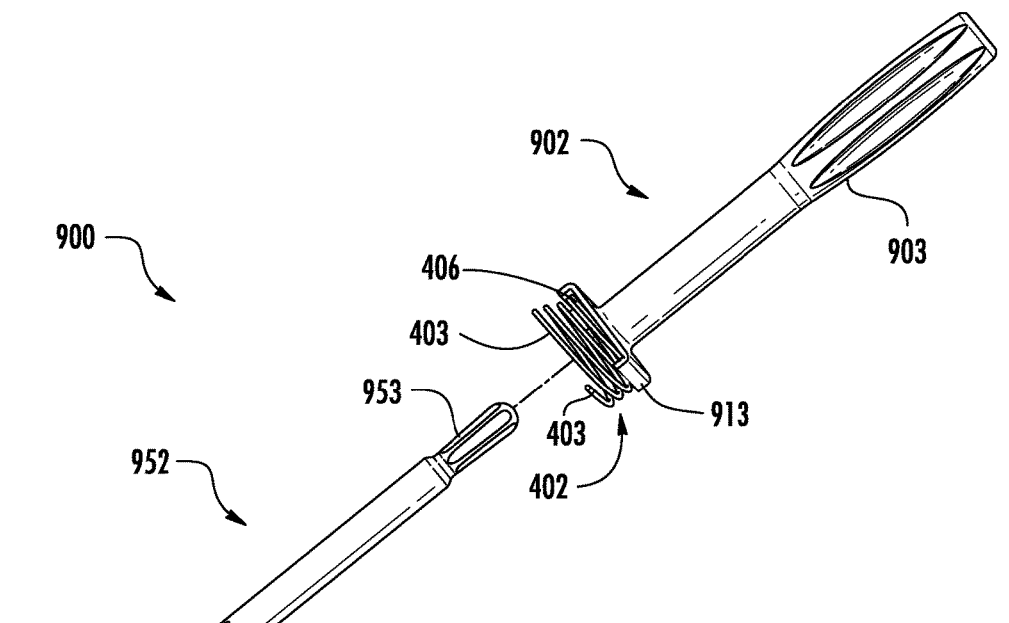
FIGS. 9A and 9B show perspective views of an instrument system for securing a port of an apical connector in a heart wall, coring a hole in the heart wall, and attaching a cannula to the port of the apical connector, in accordance with one or more embodiments of the present disclosure.
Figure 9B:
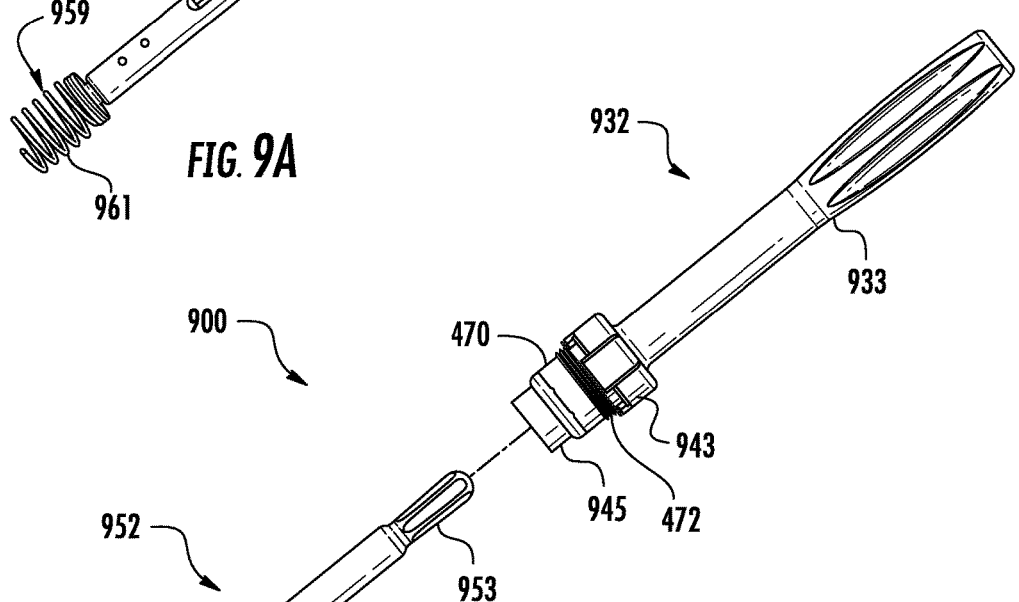

FIGS. 9A and 9B illustrate an embodiment of an instrument system 900 for securing a port of an apical connector (which also may be referred to as a "heart connector" or a "tissue connector") to a heart wall (which also may be referred to as a "tissue wall"), coring a hole in the heart wall, and attaching a cannula to the port of the apical connector. The instrument system 900 may be configured for use with the apical connector 400 described above, including the valved cannula 470 and the port 406, or any of the other connectors described herein or in the applications listed above.

The instrument system 900 may include a first instrument 902 for securing the port 406 of the connector 400 to the heart wall via the anchoring device 402, and a second instrument 932 for coring a hole in the heart wall and attaching the valved cannula 470 to the port 406. The instrument system 900 also may include a centering guide 952 for guiding each of the first instrument 902 and the second instrument 932 toward the heart wall to provide systemic concentricity.

The first instrument 902 may include a handle 903 and a port interface 913 rigidly attached to the distal end of the handle 903. The port interface 913 may be configured for removably attaching to and retaining a port of an apical connector, such as the port 406 of the apical connector 400, as shown. The handle 903 may be cannulated and configured for advancing the port 406 over the centering guide 952 in order to secure the port 406 to the heart wall via the anchoring device 402.

The second instrument 932 may include a handle 933 and a cannula interface 943 rigidly attached to the distal end of the handle 933. As shown, the second instrument 932 also may include a coring tube 945 rigidly attached to the handle 933 and extending distally beyond the cannula interface 943. The cannula interface 943 may be configured for removably attaching to and retaining a cannula of an apical connector, such as the valved cannula 470 of the apical connector 400, as shown. The coring tube 945 may be configured for contacting the heart wall and coring a hole therein, as described in detail below. When the cannula 470 is attached to the cannula interface 943, the hemostasis valve 462 may assume an open position and may form a seal against the outer surface of the coring tube 945. The handle 933 may be cannulated and configured for advancing the coring tube 945 and the cannula 470 over the centering guide 952 in order to core a hole in the heart wall and attach the cannula 470 to the port 406.

The centering guide 952 may include a handle 953 and a guide anchor 959 rigidly attached to the distal end of the handle 953. The guide anchor 959 may be configured for attaching the centering guide 952 to the heart wall. As shown, the guide anchor 959 may include one or more helical coils 961 configured for advancing into the heart wall. In other embodiments, the guide anchor 959 may include one or more pins, prongs, barbs, hooks, staples, or other similar features configured for advancing into the heart wall. The handle 953 may be configured for advancing the guide anchor 959 into the heart wall.

During use of the instrument system 900, the centering guide 952 may be oriented such that the distal end of the guide anchor 959 contacts the outer surface of the heart wall at an approximate center of the desired implantation site. The guide anchor 959 then may be advanced into the heart wall, by axial translation and/or rotation of the handle 953 of the centering guide 952, depending on the type of guide anchor 959 used. For the coiled guide anchor 959 shown, the handle 953 may be rotated and axially translated according to the helical path or paths defined by the one or more coils 961.

After attachment of the guide anchor 959, the first instrument 902 may be placed over the handle 953 of the centering guide 952, and the port 406 and the anchoring device 402 may be axially translated toward the heart wall via the handle 903. Once the anchoring device 402 contacts the outer surface of the heart wall, the anchoring device 402 may be advanced into the heart wall, by axial translation and/or rotation of the handle 903, depending on the type of anchoring device 402 used. For the coiled anchoring device 402 shown, the handle 903 may be rotated and axially translated according to the helical path or paths defined by the one or more coils 403. The anchoring device 402 may be advanced into the heart wall until the distal end of the port 406 is adequately secured near or against the outer surface of the heart wall, such as by forming a substantially fluid tight or hemostatic seal thereabout. The port interface 913 then may be detached from the port 406, and the entire first instrument 902 may be removed from the centering guide 952.

Next, the second instrument 932 may be placed over the handle 953 of the centering guide 952, and the coring tube 945 and the valved cannula 470 may be axially translated toward the heart wall via the handle 933. Once the coring tube 945 contacts the outer surface of the heart wall, the coring tube 945 may be advanced into the heart wall, by axial translation and rotation of the handle 933. At this point, the guide anchor 959 of the centering guide 952 may provide counter-traction for advancing the coring tube 945 into the heart wall. As the handle 933 is further translated and rotated according to the path of the threads 472 of the cannula 470 and the threads 474 of the port 406, the second instrument 932 may simultaneously core a hole in the heart wall as the coring tube 945 advances therethrough and attach the cannula 470 to the port 406 as the mating threads 472, 474 engage one another. When the cannula 470 is attached to the port 406, the cannula 470 may be inserted at least partially through the hole formed in the heart wall. After the hole is formed in the heart wall and the cannula 470 is securely attached to the port 406, the cannula interface 943 may be detached from the cannula 470 and the entire second instrument 932 may be removed from the centering guide 952. Alternatively, the second instrument 932 and the centering guide 952 may be simultaneously removed from the heart wall. The guide anchor 959 may be configured to retain the tissue core removed from the heart wall. As the coring tube 945 is removed from the cannula 470, the hemostasis valve 462 may close to prevent blood loss through the connector 400. A VAD then may be implanted in the heart wall via the connector 400. In particular, an inlet tube of the VAD may be inserted at least partially through the cannula 470 and at least partially through the hole in the heart wall such that the inlet tube is in communication with the ventricle of the heart. When the inlet tube is inserted through the cannula 470, the hemostasis valve 462 may assume an open position and may form a seal against the outer surface of the inlet tube. An advantage of this embodiment of the instrument system 900 is that the clinician can use the centering guide 952 with the guide anchor 959 to preliminarily determine a position and trajectory of the port 406, and thus the overall connector 400, before establishing the final implantation of the connector 400. In particular, the clinician can position, re-orient, and rotate the centering guide 952 before attaching the port 406 to the heart wall via the anchoring device 402.

Figure 10:
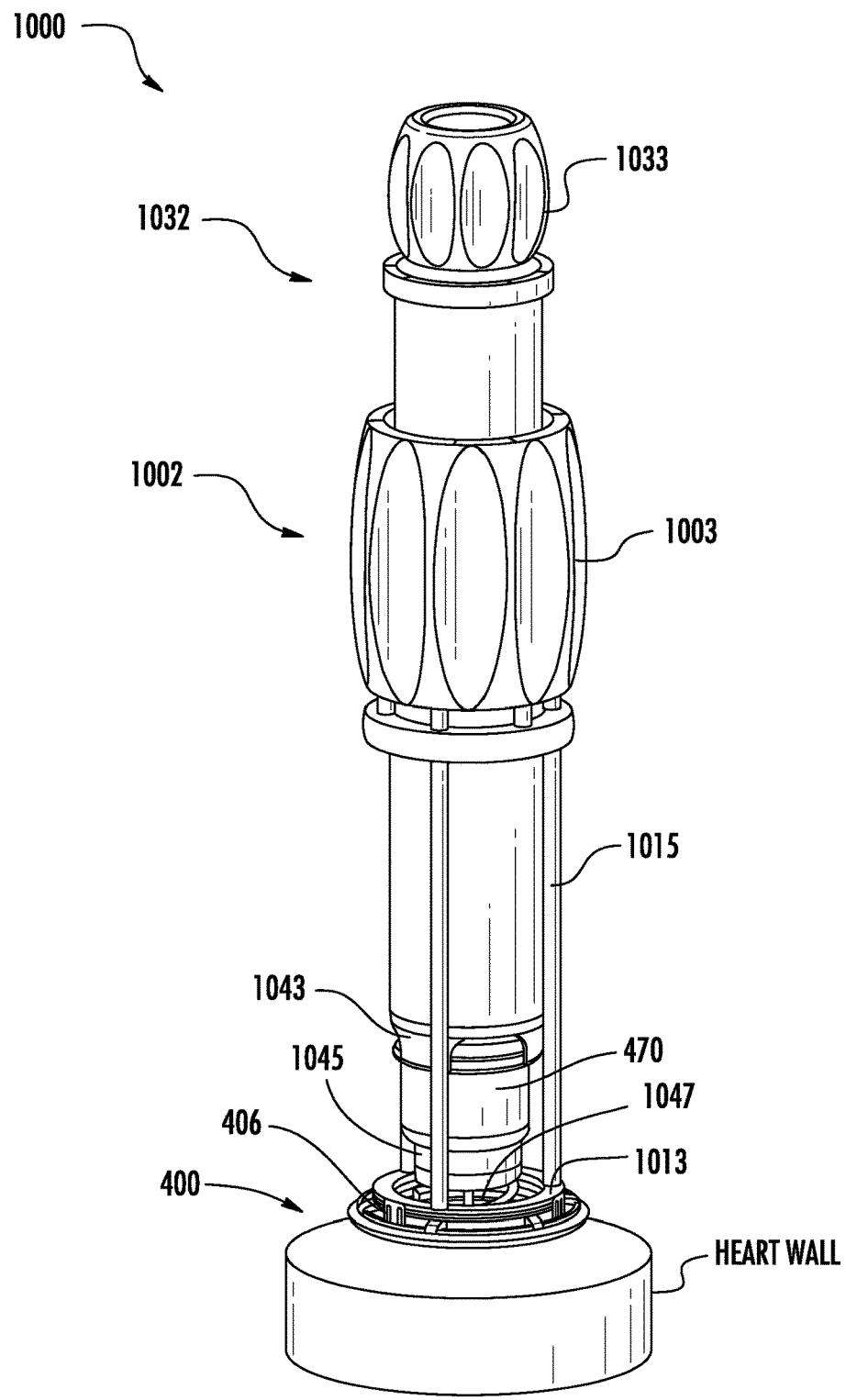
FIG. 10 shows a perspective view of an instrument system for securing a port of an apical connector in a heart wall, coring a hole in the heart wall, and attaching a cannula to the port of the apical connector, in accordance with one or more embodiments of the present disclosure.

FIG. 10 illustrates an embodiment of an instrument system 1000 for securing a port of an apical connector (which also may be referred to as a "heart connector" or a "tissue connector") to a heart wall (which also may be referred to as a "tissue wall"), coring a hole in the heart wall, and attaching a cannula to the port of the apical connector. The instrument system 1000 may be configured for use with the apical connector 400 described above, including the valved cannula 470 and the port 406, or any of the other connectors described herein or in the applications listed above.

The instrument system 1000 may include a first instrument 1002 for securing the port 406 of the connector 400 to the heart wall via the anchoring device 402, and a second instrument 1032 for coring a hole in the heart wall and attaching the valved cannula 470 to the port 406.

The first instrument 1002 may include a handle 1003 and a port interface 1013 rigidly attached to the handle 1003, such as by one or more connecting members 1015 extending therebetween. The port interface 1013 may be configured for removably attaching to and retaining a port of an apical connector, such as the port 406 of the apical connector 400, as shown. The handle 1003 may be cannulated and configured for allowing the second instrument 1032 to extend therethrough.

The second instrument 1032 may include a handle 1033 and a cannula interface 1043 rigidly attached to the distal end of the handle 1033. As shown, the second instrument 1032 also may include a coring tube 1045 rigidly attached to the handle 1033 and extending distally beyond the cannula interface 1043. The second instrument 1032 further may include a coring anchor 1047 rigidly attached to the handle 1033 and extending distally beyond the coring tube 1045. The cannula interface 1043 may be configured for removably attaching to and retaining a cannula of an apical connector, such as the valved cannula 470 of the apical connector 400, as shown. The coring tube 1045 may be configured for contacting the heart wall and coring a hole therein, as described in detail below. When the cannula 470 is attached to the cannula interface 1043, the hemostasis valve 462 may assume an open position and may form a seal against the outer surface of the coring tube 1045. The coring anchor 1047 may be configured for attaching to the heart wall prior to the coring tube 1045 contacting the heart wall. As shown, the coring anchor 1047 may include one or more helical coils 1049 configured for advancing into the heart wall. In other embodiments, the coring anchor 1047 may include one or more pins, prongs, barbs, hooks, staples, or other similar features configured for advancing into the heart wall.

During use of the instrument system 1000, the first instrument 1002 may be oriented such that the distal end of the anchoring device 402 contacts the outer surface of the heart wall while the central axis $A_C$ of the connector 400 is at an approximate center of the desired implantation site. Once the anchoring device 402 contacts the outer surface of the heart wall, the anchoring device 402 may be advanced into the heart wall, by axial translation and/or rotation of the handle 1003, depending on the type of anchoring device 402 used. For the coiled anchoring device 402 shown, the handle 1003 may be rotated and axially translated according to the helical paths or paths defined by the one or more coils 403. The anchoring device 402 may be advanced into the heart wall until the distal end of the port 406 is adequately secured near or against the outer surface of the heart wall, such as by forming a substantially fluid tight or hemostatic seal thereabout.

Next, the second instrument 1032 may be placed through the handle 1003 of the first instrument 1002, and the coring anchor 1047, the coring tube 1045, and the valved cannula 470 may be axially translated toward the heart wall via the handle 1033 until the coring anchor 1047 contacts the outer surface of the heart wall. The coring anchor 1047 then may be advanced into the heart wall, by axial translation and/or rotation of the handle 1033, depending on the type of coring anchor 1047 used. For the coiled coring anchor 1047 shown, the handle 1033 may be rotated and axially translated according to the helical path or paths defined by the one or more coils 1049.

As the coring anchor 1047 is advanced into the heart wall, the distal end of the coring tube 1045 approaches and eventually contacts the outer surface of the heart wall. At this point, the coring anchor 1047 may provide countertraction for advancing the coring tube 1045 into the heart wall. As the handle 1033 is further rotated and axially translated according to the path of the coiled coring anchor 1047, the second instrument 1032 may simultaneously core a hole in the heart wall as the coring tube 1045 advances therethrough and attach the valved cannula 470 to the port 406 as the threads 472 of the cannula 470 and the threads 474 of the port 406 engage one another. When the cannula 470 is attached to the port 406, the cannula 470 may be inserted at least partially through the hole formed in the heart wall. After the hole is formed in the heart wall and the cannula 470 is securely attached to the port 406, the cannula interface 1043 may be detached from the cannula 470 and the entire second instrument 1032 may be removed from the heart wall and the connector 400, and the port interface 1013 may be detached from the port 406 and the entire first instrument 1002 may be removed from the heart wall and the connector 400. The second instrument 1032 and the first instrument 1002 may be sequentially or simultaneously removed. The coring tube 1045 and the coring anchor 1047 may be configured to retain the tissue core removed from the heart wall within the coring tube 1045. As the coring tube 1045 is removed from the cannula 470, the hemostasis valve 462 may close to prevent blood loss through the connector 400. A VAD then may be implanted in the heart wall via the connector 400. In particular, an inlet tube of the VAD may be inserted at least partially through the cannula 470 and at least partially through the hole in the heart wall such that the inlet tube is in communication with the ventricle of the heart. When the inlet tube is inserted through the cannula 470, the hemostasis valve 462 may assume an open position and may form a seal against the outer surface of the inlet tube.

Apical Connectors

Figure 11A:
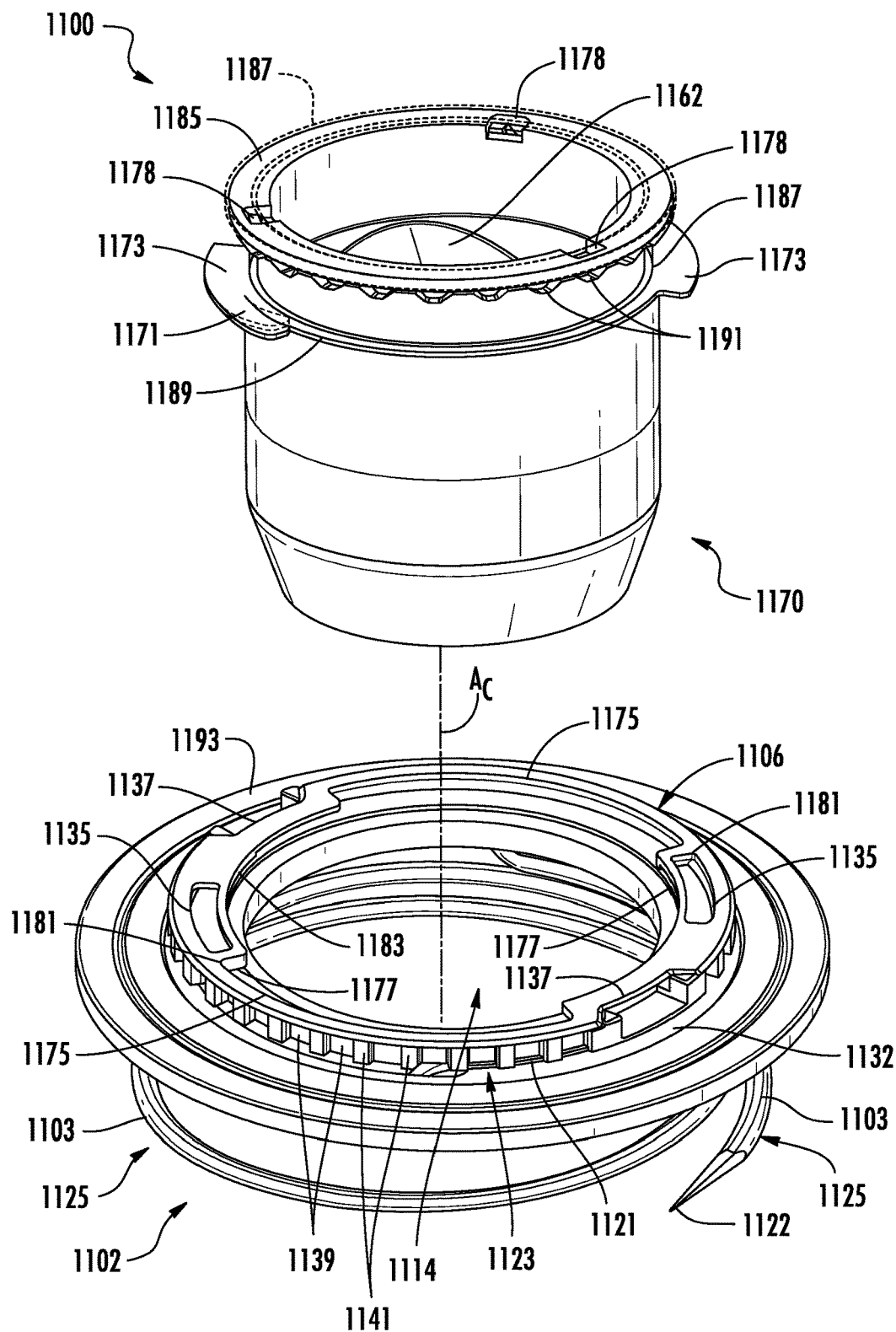
FIG. 11A shows a perspective view of a portion of an apical connector for securing in a heart wall to facilitate in vivo implantation of a VAD, in accordance with one or more embodiments of the present disclosure.

FIG. 11A illustrates an embodiment of a portion of an apical connector 1100 (which also may be referred to as a "heart connector" or a "tissue connector") configured for securing in a heart wall (which also may be referred to as a "tissue wall") to facilitate in vivo implantation of a VAD and its attachment to the heart. The connector 1100 may include an anchoring device 1102, a port 1106, and a cannula 1170 having a hemostasis valve 1162, as shown, which features may correspond generally to those described with respect to the various embodiments of the '346 Application, although certain differences are described herein below. It will be appreciated that the connector 1100 also may include other features, such as a coupler device, configured in a manner similar to those described with respect to the various embodiments of the '346 Application. Additional views of portions of the apical connector 1100 are provided in FIGS. 11B and 11C.

The anchoring device 1102 may be configured for advancing at least partially through the heart wall to secure the connector 1100 thereto for subsequent implantation of a VAD. The port 1106 may be fixedly (i.e., rigidly) attached to a proximal portion of the anchoring device 1102 and may define a central aperture 1114 therethrough. In this manner, upon advancing a distal portion of the anchoring device 1102 at least partially through the heart wall, the port 1106 may be positioned against or near the heart wall and the aperture 1114 may provide access to the heart wall. The cannula 1170 may be configured for positioning through the aperture 1114 of the port 1106 and at least partially through the heart wall. The hemostasis valve 1162 may be disposed within the cannula 1170 and configured for controlling fluid communication therethrough. During use, the apical connector 1100 may be secured to the heart wall to facilitate in vivo implantation of the VAD and its attachment to the heart in a manner similar to that described with respect to the various embodiments of the '346 Application.

Figure 11B:
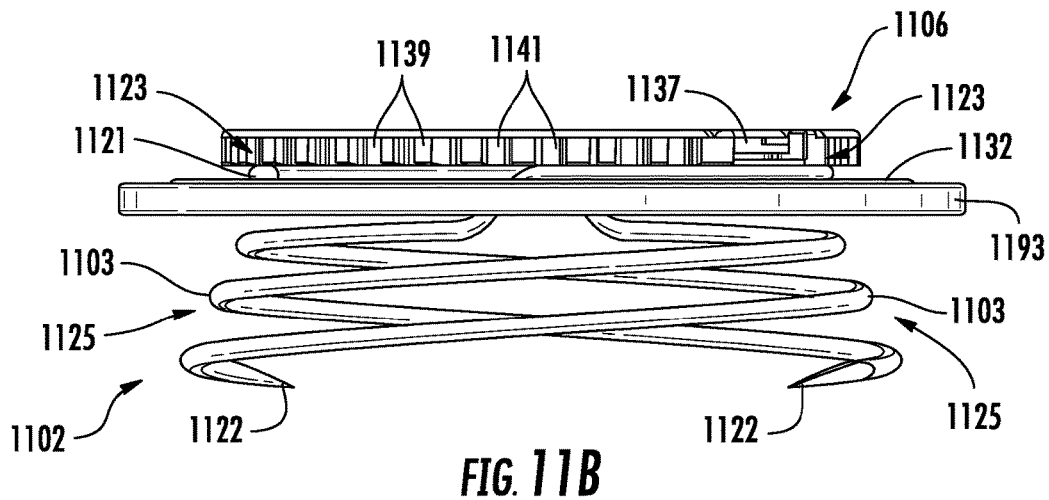
FIG. 11B shows a side view of a portion of the apical connector of FIG. 11A.
Figure 11C:
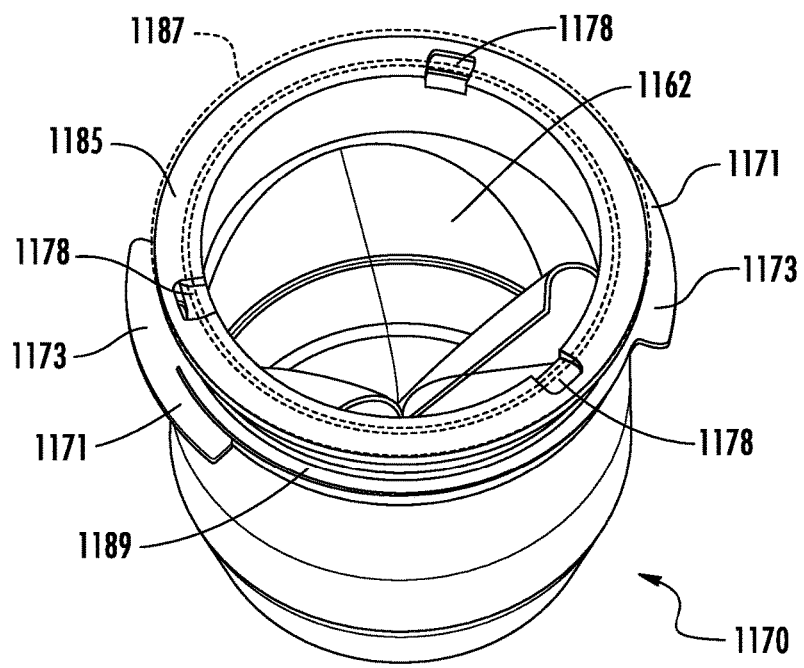
FIG. 11C shows a perspective view of a portion of the apical connector of FIG. 11A.

The anchoring device 1102 may include a plurality of helical coils 1103 positioned about a central axis $A_C$ of the connector 1100 and configured for advancing at least partially into the heart wall along respective helical paths defined by the coils 1103. For example, as shown in FIGS. 11A and 11B, the anchoring device 1102 may include two coils 1103 that are offset from one another and arranged in a generally symmetric manner about the central axis $A_C$ of the connector 1100. In particular, the two coils 1103 may be attached to the port 1106 at attachment points 1121 that are spaced apart from one another, for example, by 180-degrees in a circumferential direction with respect to the central axis $A_C$ of the connector 1100. Distal tips 1122 (i.e., distal ends) of the two coils 1103 also may be spaced apart from one another, for example, by 180-degrees in a circumferential direction with respect to the central axis $A_C$ of the connector 1100. In this manner, the coils 1103 may follow separate, opposing helical paths in the myocardial wall. In other embodiments, the anchoring device 1102 may include three or more coils 1103 that are offset from one another and arranged in a generally symmetric manner about the central axis $A_C$ of the connector 1100, such that the coils 103 follow separate helical paths in the myocardial wall. The three or more coils 103 may include attachment points 1121 and distal tips 1122 that are equally spaced from one another in a circumferential direction with respect to the central axis $A_C$ of the connector 1100. In various embodiments, the anchoring device 1102 may include two or more coils 1103 that are "clocked" (i.e., circumferentially spaced) from each other by 20 degrees, 25 degrees, 30 degrees, 45 degrees, 60 degrees, 90 degrees, or 120 degrees with respect to the central axis $A_C$ of the connector 1100. As shown, the coils 1103 may have a radially-expanding helical shape (i.e., a conical shape) such that a helical diameter of the coil 1103 increases from the proximal end to the distal end of the coil 1103. Due to the radially-expanding helical shape, the coils 1103 may be configured to compress at least a portion of the heart wall inward toward the central axis $A_C$ of the connector 1100 when the anchoring device 1102 is advanced through the heart wall. It will be appreciated from the description herein that the anchoring device 1102 may include other anchoring mechanisms (other than coils) common in the surgical field, such as clips, staples, and screws. In some embodiments, the anchoring device 102 may include a combination of different anchoring mechanisms.

As compared to embodiments in which the anchoring device 1102 includes only a single coil 1103, the plurality of coils 1103 of the foregoing embodiments may improve stability of the port 1106 as well as the overall connector 1100 when secured in the heart wall. In particular, the plurality of coils 1103 may provide balanced engagement of the heart wall and prevent the port 1106 from lifting off of the heart wall (opposite the coil insertion point), as may be experienced with a single coil configuration of the anchoring device 1102. As will be appreciated, the plurality of coils 1103 may enhance initial starting and advancing of the anchoring device 1102 in the heart wall in a manner similar to that of a multi-start threadform. Additionally, as compared to a single coil configuration, the coils 1103 may be shorter, resulting in increased rigidity of the coils 1103, which may improve implantation consistency as well as full engagement feedback as the anchoring device 1102 is secured in the heart wall. Further, the balanced engagement provided by the plurality of coils 1103 may improve hemostasis achieved upon implantation of the connector 1100, for example by ensuring balanced contact between the port 1106 and the heart wall, or between an additional sealing element of the connector 1100 and the heart wall.

As shown in FIGS. 11A and 11B, each coil 1103 may include a proximal portion 1123 fixedly (i.e., rigidly) attached to the port 1106 and a distal portion 1125 extending distally away from the port 1106 and configured for advancing at least partially into the heart wall. The proximal portion 1123 may be disposed on a proximal side of a circumferential flange 1132 of the port 1106, and the distal portion 1125 may be disposed on a distal side of the flange 1132. In some embodiments, each coil 1103 may be attached to the port 1106 via one or more welds at the respective attachment point 1121. In particular, the proximal portion 1123 of the coil 1103 may be attached to the proximal surface of the flange 1132 via one or more welds therebetween at the respective attachment point 1121. According to this configuration, the one or more welds at the attachment point 1121 may be compressed upon extension of the distal portion 1125 of the coil 1103, as may be experienced during or after advancement of the distal portion 1125 into the heart wall. Such compression may limit loading on the one or more welds and enhance durability of the attachment point 1121 under fatigue, as may be experienced during use of the apical connector 1100 in the heart wall.

The port 1106 may be formed as a substantially ring-shaped member defining the central aperture 1114 therethrough and configured for positioning against or near the heart wall. As noted above, the port 1106 may be fixedly (i.e., rigidly) attached to the anchoring device 1102, in particular the proximal portions 1123 of the coils 1103. In this manner, axial rotation of the port 1106 results in corresponding axial rotation of the anchoring device 1102 for advancing the anchoring device 1102 at least partially into the tissue wall. The port 1106 may include one or more engagement features configured for engaging an instrument used to secure the port 1106 to the heart wall via the anchoring device 1102. For example, the port 1106 may include one or more engagement apertures 1135 (which also may be referred to as "engagement recesses") defined in the proximal end of the port 1106 and configured for receiving a mating feature of the instrument. Alternatively or additionally, the port 1160 may include one or more engagement notches 1137 (which also may be referred to as "engagement recesses") defined in the proximal end of the port 1106 along the circumferential outer surface thereof and configured for receiving a mating feature of the instrument. Certain embodiments of an instrument that may be used to secure the port 1106 to the heart wall are described herein below.

The port 1106 also may include one or more engagement features configured for engaging an instrument used to stabilize the port 1106 after the port 1106 has been secured to the heart wall. For example, the port 1106 may include a plurality of engagement notches 1139 (which also may be referred to as "engagement recesses") defined in the circumferential outer surface of the port 1106 and configured for receiving a mating feature of the instrument. The notches 1139 may be configured for allowing the instrument to engage the port 1106 from a plurality of directions relative to the aperture 1114 of the port 1106 and the central axis $A_C$ of the connector 1100. As shown, the notches 1139 may be arranged in a circumferential array along the circumferential outer surface of the port 1106 and may have a plurality of engagement tabs 1141 (which also may be referred to as "engagement protrusions") positioned therebetween. In other words, one of the engagement tabs 1141 may be positioned between each adjacent pair of the engagement notches 1139. In some embodiments, as shown, the notches 1139 may provide discrete engagement positions every 10 degrees about the circumferential outer surface of the port 1106. According to other embodiments, the notches 1139 may provide discrete engagement positions every 5 degrees, 15 degrees, 30 degrees, 45 degrees, or 90 degrees about the circumferential outer surface of the port 1106. Certain embodiments of an instrument that may be used to stabilize the port 1106 after the port 1106 has been secured to the heart wall are described herein below.

The cannula 1170 may be formed as a substantially tube-shaped member configured for positioning through the aperture 1114 of the port 1106 and at least partially through the heart wall. The cannula 1170 may include one or more features configured for releasably attaching the cannula 1170 to the port 1106. For example, as shown, the cannula 1170 may include one or more locking members 1171 (which also may be referred to as "locking arms" or "locking tabs") positioned near but offset from the proximal end of the cannula 1170 and extending along the outer circumferential surface of the cannula 1170. Each locking member 1171 may extend from a partial flange 1173 of the cannula 1170 and may be resilient or spring-like and configured to deflect from a natural position (as shown via dashed lines in FIG. 11A) to a biased position (as shown via solid lines in FIG. 11A) when a biasing force is applied thereto via mating features of the port 1106 as the cannula 1170 is attached to the port 1106. In some embodiments, in the natural position, the locking member 1171 may extend at least partially toward the proximal end of the cannula 1170 in an angled relationship with respect to the partial flange 1173, and in the biased position, the locking member 1171 may be deflected at least partially away from the proximal end of the cannula 1170 to or toward a coplanar relationship with the partial flange 1173.

The port 1106 may include one or more recesses 1175 defined in the proximal end of the port 1106 and configured to allow the locking members 1171 and the partial flanges 1173 to be inserted axially therein. The port 1106 also may include one or more undercut grooves 1177 defined near the proximal end of the port 1106 and extending along the inner circumferential surface of the port 1106. Each undercut groove 1177 may be positioned adjacent to and in communication with one of the recesses 1175. The undercut grooves 1177 may be configured to receive the partial flanges 1173 and the locking members 1171 of the cannula 1170 upon rotation of the cannula 1170 with respect to the port 1106. The cannula 1170 may include one or more engagement features configured for engaging an instrument used to position the cannula 1170 within the aperture 1114 of the port 1106 and rotate the cannula 1170 with respect to the port 1106. For example, the cannula 1170 may include a plurality of engagement notches 1178 (which also may be referred to as "engagement recesses") defined in the proximal end of the cannula 1170 and configured for receiving a mating feature of the instrument. In some embodiments, as shown, the engagement notches 1178 may extend to the inner circumferential surface of the cannula 1170. In other embodiments, the engagement notches 1178 may extend to the outer circumferential surface of the cannula 1170. Certain embodiments of an instrument that may be used to position the cannula 1170 within the aperture 1114 of the port 1106 and rotate the cannula 1170 with respect to the port 1106 are described herein below.

The port 1106 further may include one or more locking protrusions 1181 (which also may be referred to as "locking tabs") and one or more stop protrusions 1183 (which also may be referred to as "stop tabs"). The locking protrusions 1181 may be configured to deflect the locking members 1171 of the cannula 1170 distally (i.e., away from the proximal end of the cannula 1170) from their natural position upon rotation of the cannula 1170 with respect to the port 1106 in a first direction, such as a clockwise direction when viewed from the proximal end of the connector 1100. The stop protrusions 1183 may be configured to contact the locking members 1171 and/or the partial flanges 1173 and limit rotation of the cannula 1170 with respect to the port 1106 in the first direction. The locking members 1171 may be configured to return to or toward their natural position after advancing past the locking protrusions 1181, such that the locking members 1171 and the locking protrusions 1181 cooperate to prevent rotation of the cannula 1170 with respect to the port 1106 in an opposite second direction, such as a counter clockwise direction when viewed from the proximal end of the connector 1100. In this manner, the mating features of the cannula 1170 and the port 1106 may form a partial-turn locking mechanism configured to prevent the cannula 1170 from being detached from the port 1106 unless the locking members 1171 are biased by a user to disengage the locking protrusions 1181. According to the embodiment shown in FIGS. 11A-11C, the partial-turn locking mechanism is a ¼-turn locking mechanism, although other configurations are possible, such as a ⅓-turn or a ½-turn configuration.

As compared to some other connector embodiments, the partial-turn locking mechanism of the connector 1100 provides a means for locking the cannula 1170 to the port 1106, which may improve the structural integrity of the connector 1100 as well as the hemostasis achieved upon implantation of the connector 1100. Moreover, the partial-turn locking mechanism provides tactile feedback as the cannula 1170 is attached to the port 1106.

The partial-turn locking mechanism of the connector 1100 may be released to allow the cannula 1170 to be detached from the port 1106. In particular, the partial-turn locking mechanism may be released by inserting portions of an instrument through the engagement apertures 1135 of the port 1106 and biasing the locking members 1171 of the cannula 1170 distally such that the locking members 1171 disengage the locking protrusions 1181. Such disengagement of the locking members 1171 and the locking protrusions 1181 may allow the cannula 1170 to be rotated in the second direction and then axially removed from the port 1106. Certain embodiments of an instrument that may be used to release the partial-turn locking mechanism are described in PCT Application No. PCT/US2015/019308 (the '308 application) and referred to therein as a cannula release tool. As described, the cannula release tool may include a pair of prongs. It will be appreciated that the prongs may be inserted through the engagement apertures 1135 of the port 1106 to bias the locking members 1171 of the cannula 1170 distally such that the locking members 1171 disengage the locking protrusions 1181, thereby allowing the cannula 1170 to be rotated in the second direction and then axially removed from the port 1106.

The cannula 1170 may include one or more features configured for facilitating attachment of a VAD to the apical connector 1100. For example, as shown, the cannula 1170 may include a proximal flange 1185 (which also may be referred to as a "proximal lip") positioned at or near the proximal end of the cannula 1170 and extending along the outer circumferential surface of the cannula 1170. The cannula 1170 also may include an elastomer covering 1187 molded over a portion of the cannula 1170. The elastomer covering 1187 may extend from the proximal end of the cannula 1170 to an intermediate flange 1189 (which also may be referred to as an "intermediate lip"). As shown, the partial flanges 1173 may be attached to and coplanar with the intermediate flange 1189. In other embodiments, the intermediate flange 1189 may be offset from the partial flanges 1173. As shown, the elastomer covering 1187 may extend partially over the engagement notches 1178 along the proximal end of the cannula 1170, which may facilitate retention of mating features of an instrument within the engagement notches 1178 during positioning of the cannula 1170 with respect to the port 1106. In some embodiments, the elastomer covering 1187 may extend partially into the engagement notches 1178, which also may facilitate retention of mating features of the instrument. The elastomer covering 1187 may include a plurality of ridges 1191 defined in the circumferential outer surface of the elastomer covering 1187, positioned distally with respect to the proximal flange 1185 and extending toward the distal end of the cannula 1170.

When the cannula 1170 is attached to the port 1106, a circumferential groove or gap may exist between the proximal flange 1185 and the proximal end of the port 1106. The circumferential groove may be configured to receive a mating portion of a locking mechanism, such as a clip, for attaching a VAD to the connector 1100. In some embodiments, the mating portion of the locking mechanism, such as the clip, may include features configured to engage the ridges 1191 and thereby limit rotation of the locking mechanism and the VAD relative to the cannula 1170 and the overall connector 1100. Certain embodiments of locking mechanisms that may be used to attach a VAD or heart pump to a ventricular cuff are described in the '308 application. It will be appreciated that a proximal portion of the cannula 1170, including the proximal flange 1185, the elastomer covering 1187, the intermediate flange 1189, and the ridges 1191 thereof, may be configured in a manner similar to corresponding features of the various embodiments of cuffs described in the '308 application. In this manner, the cannula 1170 and the overall connector 1100 may be configured for attachment of a VAD via one or more of the embodiments of locking mechanisms described in the '308 application.

As shown in FIGS. 11A and 11B, the apical connector 1100 may include a sewing ring 1193 extending outwardly from the port 1106. The sewing ring 1193 may extend about the outer perimeter of the port 1106 and may be configured for suturing to the heart wall. The sewing ring 1193 may be made of a porous material, such as PTFE felt. Certain embodiments of sewing rings used as a part of ventricular cuffs are described in the '308 application. The sewing ring 1193 of the connector 1100 may have features and characteristics similar to those of the various embodiments of sewing rings described in the '308 application and may be attached to the port 1106 using attachment features and/or methods similar to those described therein.

Instruments

Figure 12A:
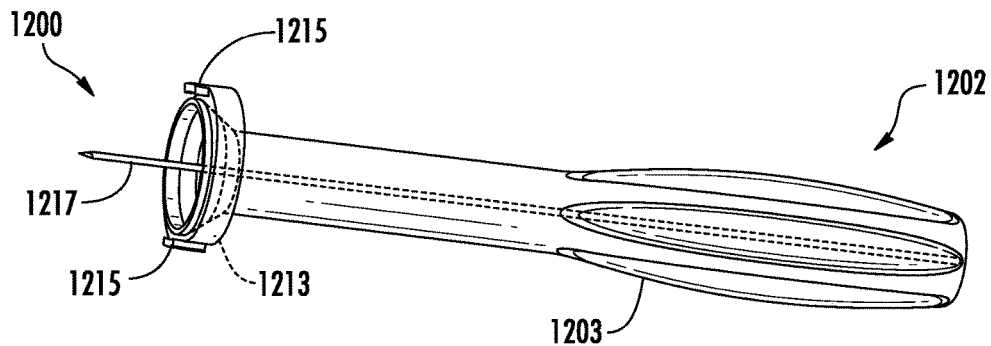
FIG. 12A shows a perspective view of an instrument system for securing a port of an apical connector in a heart wall, coring a hole in the heart wall, and attaching a cannula to the port of the apical connector, in accordance with one or more embodiments of the present disclosure.
Figure 12A:
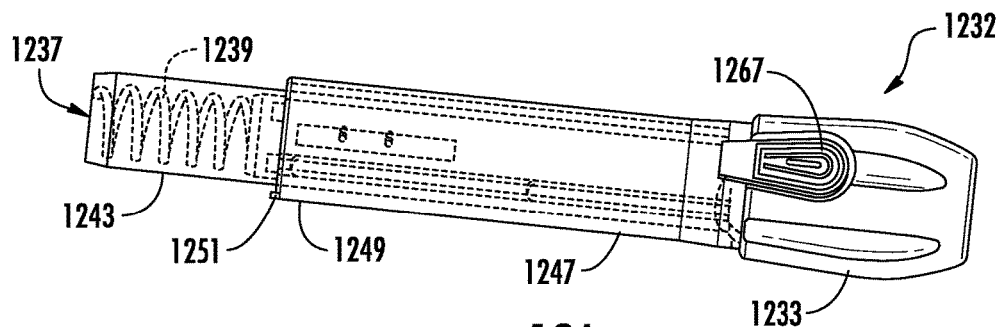
Figure 12B:
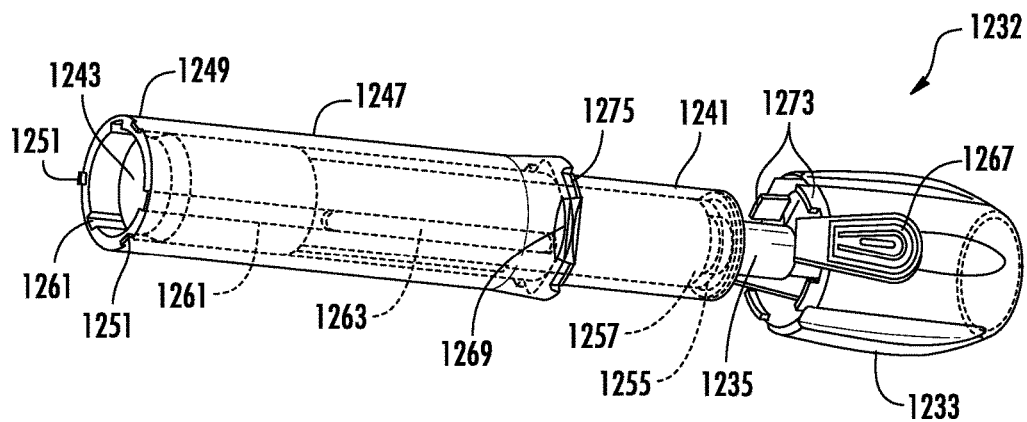
FIG. 12B shows a perspective view of a second instrument of the instrument system of FIG. 12A.

FIGS. 12A and 12B illustrate an embodiment of an instrument system 1200 for securing a port of an apical connector (which also may be referred to as a "heart connector" or a "tissue connector") to a heart wall (which also may be referred to as a "tissue wall"), coring a hole in the heart wall, and attaching a cannula to the port of the apical connector. The instrument system 1200 may be configured for use with the apical connector 1100 described above, including the valved cannula 1170 and the port 1106, or any of the other connectors described herein or in the applications listed above. FIGS. 12C-12H illustrate an example method of using the instrument system 1200 to secure the port 1106 of the apical connector 1100 in a heart wall, core a hole in the heart wall, and attach the valved cannula 1170 to the port 1106.

The instrument system 1200 may include a first instrument 1202 for securing the port 1106 of the connector 1100 to the heart wall via the anchoring device 1102, and a second instrument 1232 for coring a hole in the heart wall and attaching the valved cannula 1170 to the port 1106.

The first instrument 1202 may include a handle 1203 and a port interface 1213 rigidly attached to the distal end of the handle 1203. The port interface 1213 may be configured for removably attaching to and retaining a port of an apical connector, such as the port 1106 of the apical connector 1100, as shown. For example, the port interface 1213 may include one or more engagement protrusions 1215 (which also may be referred to as "engagement tabs") configured for inserting into the engagement apertures 1135 and/or the engagement notches 1137 of the port 1106. In some embodiments, the first instrument 1202 may include a guide member 1217 rigidly attached to the handle 1203 and extending distally beyond the port interface 1213. In this manner, the guide member 1217 may contact and be advanced into the heart wall prior to the anchoring device 1102, which may facilitate placement of the port 1106 at a desired implantation site, such as the apex of the heart. In other embodiments, the handle 1203 may be cannulated and configured for advancing the port 1106 and the first instrument 1202 over a separate guide member, such as a guide wire, previously placed in the heart wall.

The second instrument 1232 may include a main handle 1233, a shaft 1235 rigidly attached to the main handle 1233 and extending distally therefrom, and a coring anchor 1237 rigidly attached to the distal end of the shaft 1235 and extending distally therefrom. The coring anchor 1237 may be configured for attaching to the heart wall. As shown, the coring anchor 1237 may include one or more helical coils 1239 configured for advancing into the heart wall. In other embodiments, the coring anchor 1237 may include one or more pins, prongs, barbs, hooks, staples, or other similar features configured for advancing into the heart wall. The second instrument 1232 also may include a coring sleeve 1241 (which also may be referred to as an "inner sleeve") and a coring tube 1243 rigidly attached to the distal end of the coring sleeve 1241 and extending distally therefrom. The coring tube 1243 may be configured for contacting the heart wall and coring a hole therein, as described in detail below. The second instrument 1232 further may include an attachment sleeve 1247 (which also may be referred to as an "outer sleeve") and a cannula interface 1249 rigidly attached to the distal end of the attachment sleeve 1247 and extending distally therefrom. The cannula interface 1249 may be configured for removably attaching to and retaining a cannula of an apical connector, such as the valved cannula 1170 of the apical connector 1100. For example, the cannula interface 1249 may include one or more engagement protrusions 1251 configured for inserting into the engagement notches 1178 of the cannula 1170.

The coring sleeve 1241 may be configured for advancing the coring tube 1243 toward the heart wall and through the aperture 1114 of the port 1106 to core a hole in the heart wall, as described in detail below. The coring sleeve 1241 and the coring tube 1243 may be cannulated and movably positioned over respective portions of the shaft 1235 and the coring anchor 1237. In particular, the coring sleeve 1241 and the coring tube 1243 may be configured to translate axially with respect to the main handle 1233, the shaft 1235, and the coring anchor 1237 from a proximal position, as shown in FIG. 12A, to a distal position, as shown in FIG. 12B. Such axial translation of the coring sleeve 1241 may be limited in the proximal direction by contact between the coring sleeve 1241 and the main handle 1233 and in the distal direction by contact between an inner flange 1255 of the coring sleeve 1241 and a boss 1257 of the shaft 1235. In some embodiments, as shown in FIG. 12A, the coring anchor 1237 may be positioned entirely within the coring tube 1243 when the coring sleeve 1241 and the coring tube 1243 are in the proximal position. In other embodiments, as shown in FIG. 12E, a distal portion of the coring anchor 1237 may extend distally beyond the distal end of the coring tube 1243 when the coring sleeve 1241 and the coring tube 1243 are in the proximal position. In some embodiments, the coring sleeve 1241 and the coring tube 1243 may be configured to rotate with respect to the main handle 1233 and the shaft 1235. In other embodiments, the coring sleeve 1241 and the coring tube 1243 may be rotatably keyed, either directly or indirectly, to the main handle 1233 and/or the shaft 1235.

The attachment sleeve 1247 may be configured for advancing the cannula interface 1249 (and the cannula 1170 attached thereto) toward the port 1106 previously attached to the heart wall via the anchoring device 1102, as described in detail below. The attachment sleeve 1247 and the cannula interface 1249 may be cannulated and movably positioned over respective portions of the coring sleeve 1241, the coring tube 1243, the shaft 1235, and the coring anchor 1237. In particular, the attachment sleeve 1247 and the cannula interface 1249 may be configured to translate axially with respect to the coring sleeve 1241, the coring tube 1243, the shaft 1235, and the coring anchor 1237 from a proximal position, as shown in FIG. 12A, to a distal position, as shown in FIG. 12B. Such axial translation of the attachment sleeve 1247 may be limited in the proximal direction by contact between the attachment sleeve 1247 and the main handle 1233 and in the distal direction by contact between a proximal end of one or more axial grooves 1261 of the attachment sleeve 1247 and a proximal end of one or more axial ribs 1263 of the coring sleeve 1241. In some embodiments, as shown in FIGS. 12A and 12E, a distal portion of the coring tube 1243 may extend distally beyond the distal end of the cannula interface 1249 and beyond the distal end of the cannula 1170 when the attachment sleeve 1241 and the cannula interface 1249 are in the proximal position. In some embodiments, the attachment sleeve 1247 and the cannula interface 1249 may be rotatably keyed to the coring sleeve 1241 and the coring tube 1243. For example, the attachment sleeve 1247 and the coring sleeve 1241 may be rotatably keyed to one another via the axial grooves 1261 and the axial ribs 1263.

The second instrument 1232 may be adjusted between a first configuration, as shown in FIG. 12A, for coring a hole in a heart wall and attaching the cannula 1170 to the port 1106, and a second configuration, as shown in FIG. 12B, for retrieving a tissue core removed from the heart wall and detaching the second instrument 1232 from the cannula 1170. The second instrument 1232 may include one or more buttons or switches 1267 positioned on the main handle 1233 and configured for releasably engaging the attachment sleeve 1247. In particular, distal portions of the switches 1267, which may be formed as teeth, may releasably engage one or more engagement notches 1269 (which also may be referred to as "engagement recesses") defined in the attachment sleeve 1247 at or near the proximal end of the attachment sleeve 1247. When the second instrument 1232 is in the first configuration, engagement between the switches 1267 and the engagement notches 1269 may maintain the attachment sleeve 1247 and the cannula interface 1249 in their proximal position, which in turn may maintain the coring sleeve 1241 and the coring tube 1243 in their proximal position. Upon release of the switches 1267 (i.e., disengagement of the switches 1267 and the engagement notches 1269), the second instrument 1232 may be adjusted to the second configuration, in which the attachment sleeve 1247 and the cannula interface 1249 are in their distal position and the coring sleeve 1241 and the coring tube 1243 are in their distal position.

When the second instrument 1232 is in the first configuration, the attachment sleeve 1247 and the cannula interface 1249 may be rotatably keyed to the main handle 1233. For example, as shown, the main handle 1233 may include one or more engagement protrusions 1273 (which also may be referred to as "engagement tabs") extending from the distal end thereof and configured for engaging one or more engagement notches 1275 (which also may be referred to as "engagement recesses") defined in the proximal end of the attachment sleeve 1247 when the attachment sleeve 1247 is in its proximal position. As described above, the attachment sleeve 1247 and the coring sleeve 1241 may be rotatably keyed to one another, and the coring anchor 1237 may be rigidly attached to the shaft 1235, which may be rigidly attached to the main handle 1233. Accordingly, when the second instrument 1232 is in the first configuration, rotation of the main handle 1233 may result in rotation of the coring anchor 1237, the coring tube 1243, and the attached cannula 1170.

Figure 12C:
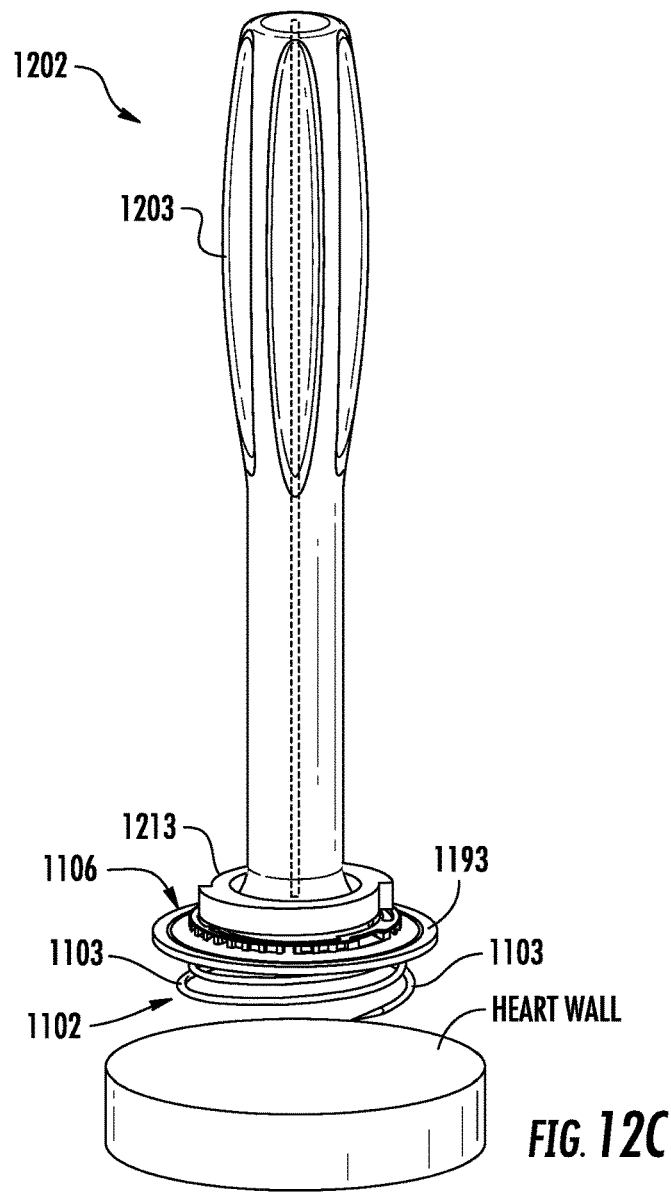
FIGS. 12C-12H show perspective views illustrating use of the instrument system of FIG. 12A to secure a port of an apical connector in a heart wall, core a hole in the heart wall, and attach a cannula to the port of the apical connector, in accordance with one or more embodiments of the present disclosure.
Figure 12D:
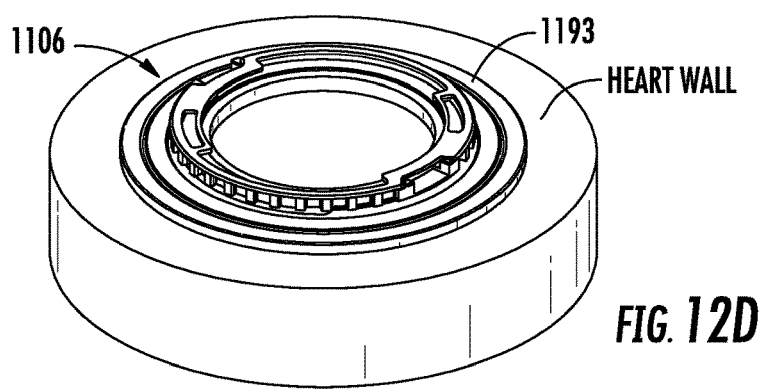
Figure 12E:
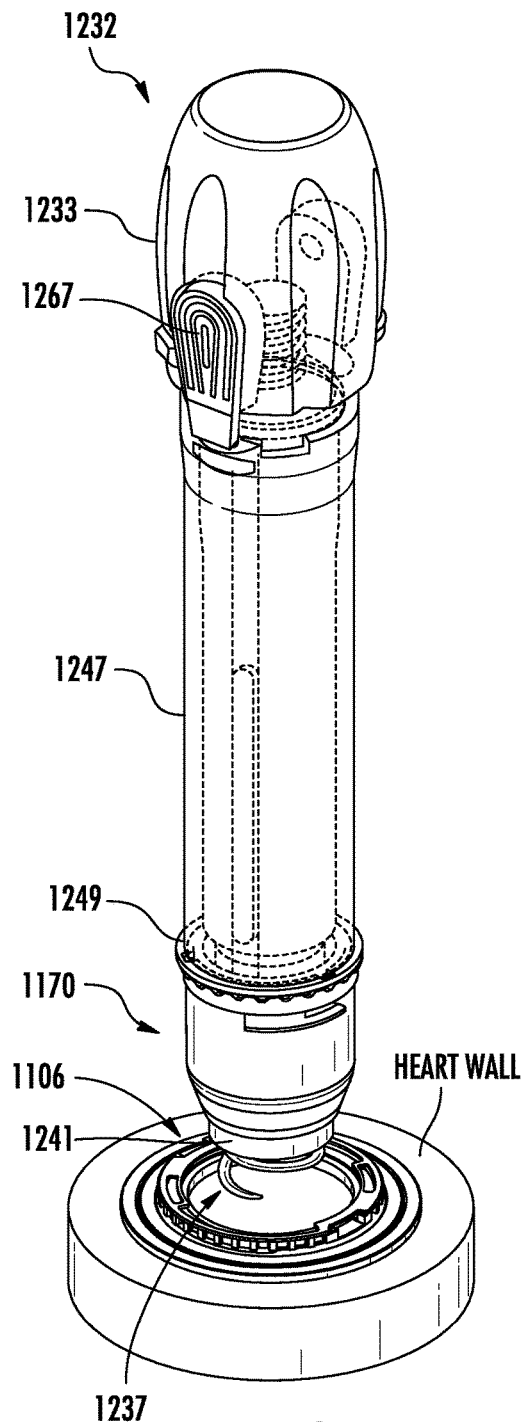

During use of the instrument system 1200, the port 1106 may be attached to the first instrument 1202 via the port interface 1213 and advanced toward the heart wall, as shown in FIG. 12C. In some embodiments, a guide wire first may be inserted into the heart wall at an approximate center of the desired implantation site, and the first instrument 1202 and the port 1106 may be advanced over the guide wire to the heart wall. In other embodiments in which the first instrument 1202 includes the guide member 1217, the first instrument 1202 may be advanced toward the heart wall such that the guide member 1217 is inserted therein at an approximate center of the desired implantation site. The first instrument 1202, the port 1106, and the anchoring device 1102 may be axially translated toward the heart wall via the handle 1203. Once the anchoring device 1102 contacts the outer surface of the heart wall, the anchoring device 1102 may be advanced into the heart wall, by axial translation and/or rotation of the handle 1203, depending on the type of anchoring device 1102 used. For the coiled anchoring device 1102 shown, the handle 1203 may be rotated and axially translated according to the helical paths defined by the coils 1103. The anchoring device 1102 may be advanced into the heart wall until the distal end of the port 1106 and/or the sewing ring 1193 is adequately secured against the outer surface of the heart wall, such as by forming a substantially fluid tight or hemostatic seal thereabout. In certain embodiments, the anchoring device 1102 is configured to be secured in the heart wall after a predetermined number of rotations. In certain embodiments, a marker provides visual confirmation to a user that the port 1106 is secured and flush against the heart wall. The port interface 1213 then may be detached from the port 1106, and the entire first instrument 1202 may be removed from the patient, leaving the port 1106 secured to the heart wall, as shown in FIG. 12D. In some embodiments, the sewing ring 1193 may be sutured to the heart wall to further secure the port 1106 to the heart wall, to enhance a seal between the sewing ring 1193 and the heart wall, and/or to further inhibit rotation of the anchoring device 1102 out of the heart wall.

Next, with the second instrument 1232 in the first configuration, the valved cannula 1170 may be attached to the second instrument 1232 via the cannula interface 1249 and advanced toward the heart wall, as shown in FIG. 12E. The second instrument 1232 and the cannula 1170 may be axially translated toward the heart wall via the main handle 1233. The distal end of the second instrument 1232 may be inserted through the aperture 1114 of the port 1106 until the coring anchor 1237 contacts the outer surface of the heart wall. The coring anchor 1237 then may be advanced into the heart wall, by axial translation and/or rotation of the main handle 1233, depending on the type of coring anchor 1237 used. For the coiled coring anchor 1237 shown, the handle 1233 may be rotated and axially translated according to the helical path defined by the coil 1239.

Figure 12F:
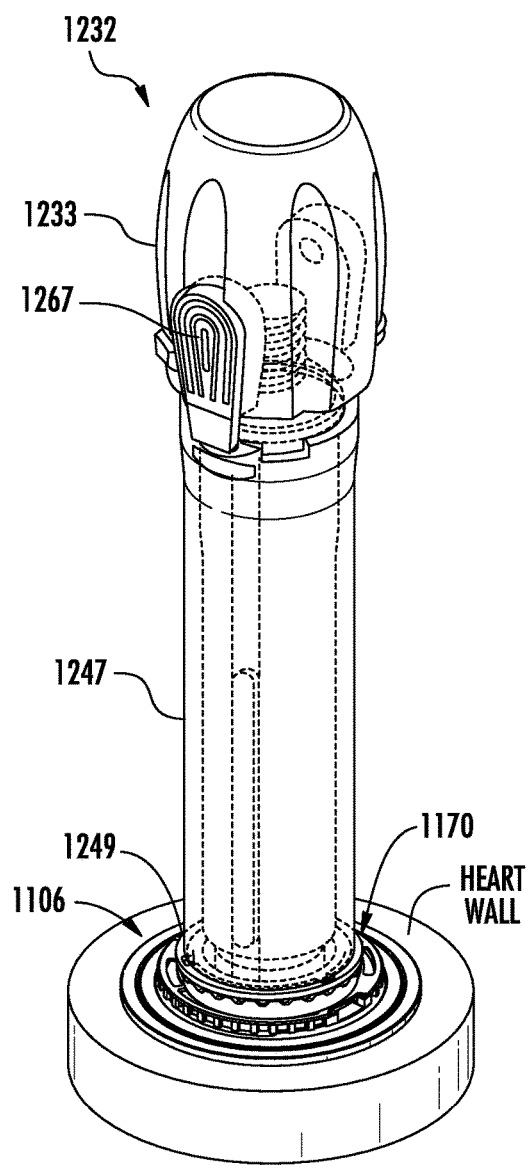

As the coring anchor 1237 is advanced into the heart wall, the distal end of the coring tube 1243 approaches and eventually contacts the outer surface of the heart wall. At this point, the coring anchor 1237 may provide counter-traction for advancing the coring tube 1243 into the heart wall. As the main handle 1233 is further rotated and axially translated according to the path of the coiled coring anchor 1237, the second instrument 1232 may simultaneously core a hole in the heart wall as the coring tube 1243 advances therethrough and position the valved cannula 1170 through the port 1106 and at least partially through the heart wall via the hole formed therein. The main handle 1233 may be rotated and axially translated until the cannula 1170 securely attaches to the port 1106, as shown in FIG. 12F. The cannula 1170 may be attached to the port 1106 via the partial-turn locking mechanism, as shown, or other means of attachment.

Figure 12G:
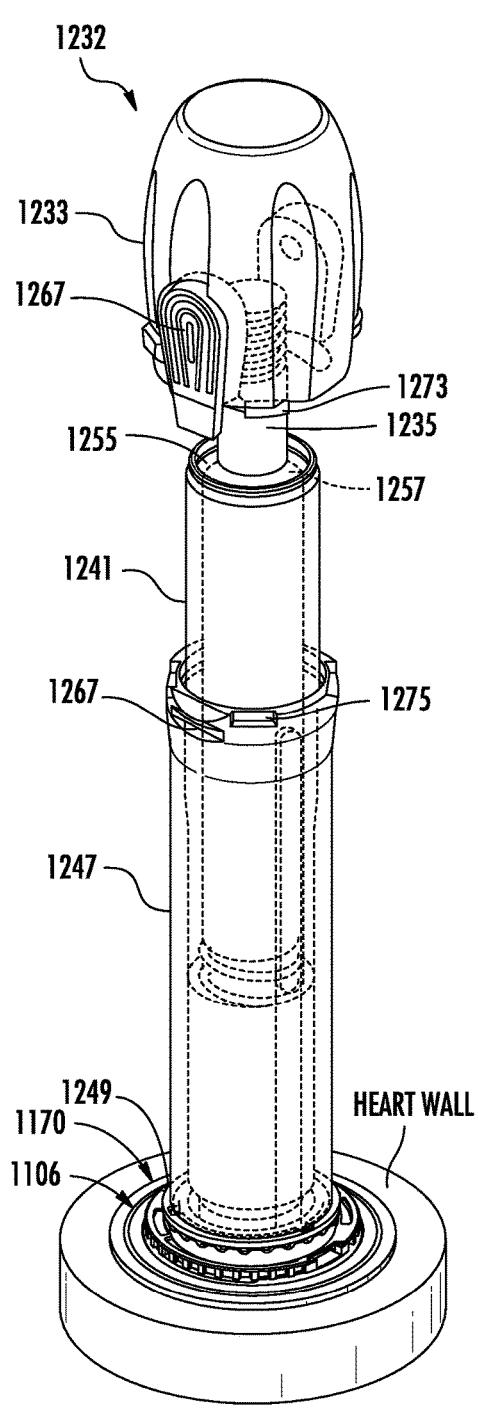
Figure 12H:
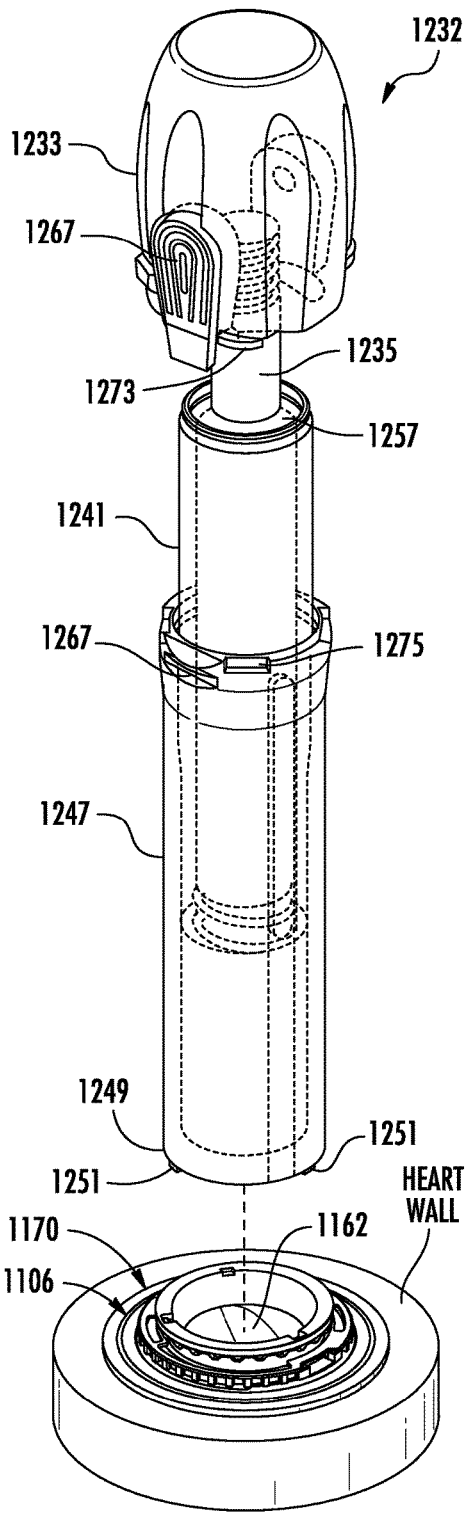

After the hole is formed in the heart wall and the cannula 1170 is securely attached to the port 1106, the switches 1267 may be released and the second instrument 1232 may be adjusted from the first configuration to the second configuration by pulling the main handle 1233 proximally away from the heart wall. As the second instrument 1232 is adjusted from the first configuration to the second configuration, the coring anchor 1237 may move into the coring tube 1243 while holding the tissue core removed from the heart wall, and the coring tube 1243 may move into the attachment sleeve 1247, as shown in FIG. 12G. The cannula interface 1249 then may be detached from the cannula 1170 and the entire second instrument 1232 may be removed from the heart wall and the connector 1100, as shown in FIG. 12H. The coring tube 1243 and the coring anchor 1237 may be configured to retain the tissue core removed from the heart wall within the coring tube 1243. As the coring tube 1243 is removed from the cannula 1170, the hemostasis valve 1162 may close to prevent blood loss through the connector 1100. A VAD or other instrument then may be implanted in the heart wall via the connector 1100. In particular, an inlet tube of a VAD may be inserted at least partially through the cannula 1170 and at least partially through the hole in the heart wall such that the inlet tube is in communication with the ventricle of the heart. When the inlet tube is inserted through the cannula 1170, the hemostasis valve 1162 may assume an open position and may form a seal against the outer surface of the inlet tube.

Figure 13A:
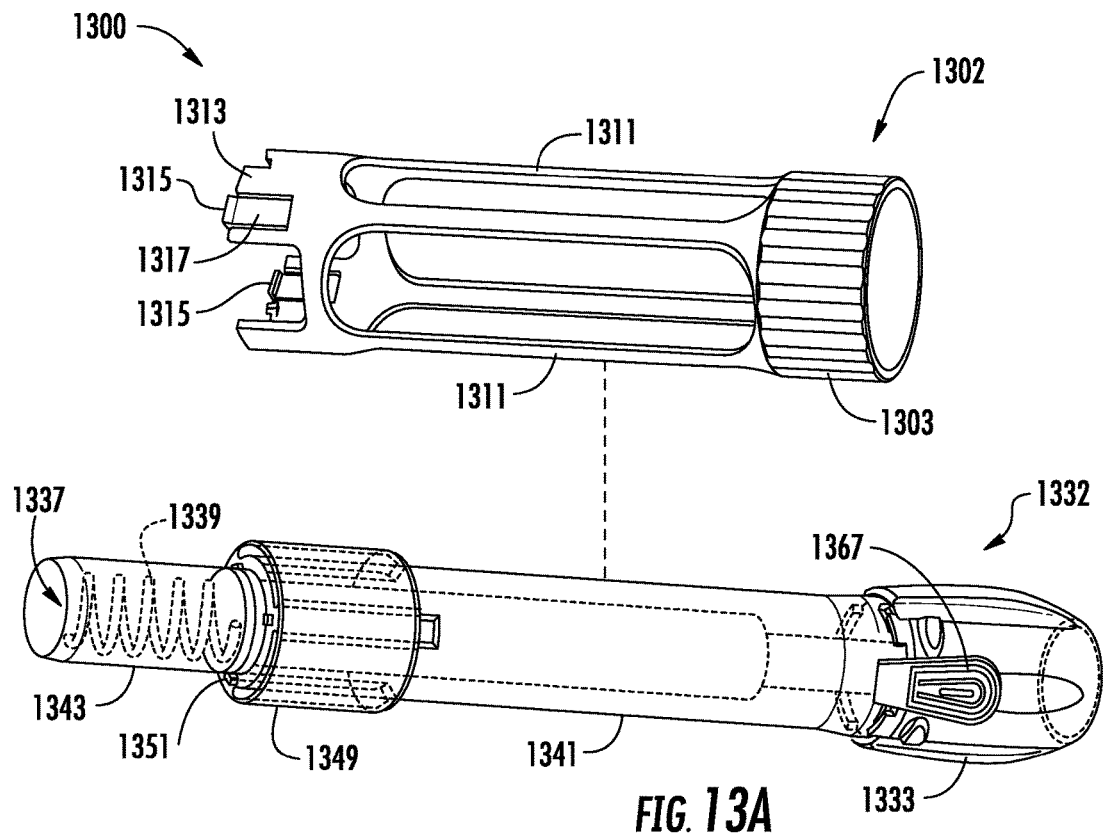
FIG. 13A shows a perspective view of an instrument system for securing a port of an apical connector in a heart wall, coring a hole in the heart wall, and attaching a cannula to the port of the apical connector, in accordance with one or more embodiments of the present disclosure.
Figure 13B:
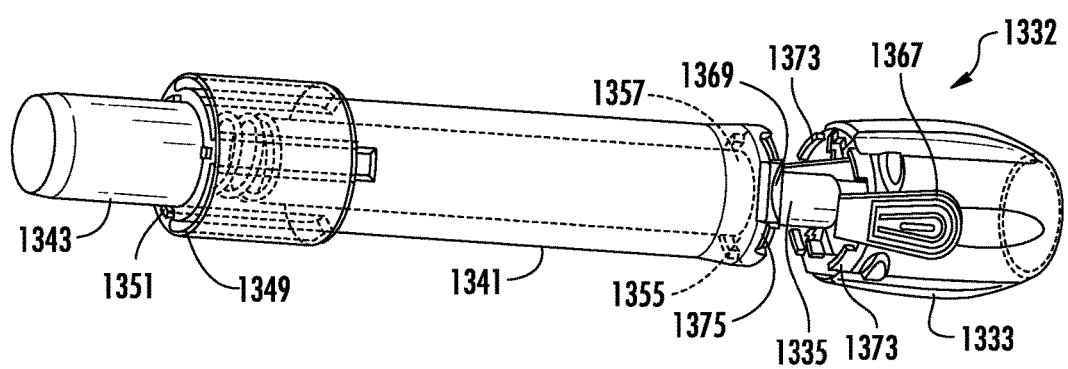
FIG. 13B shows a perspective view of a second instrument of the instrument system of FIG. 13A.

FIGS. 13A and 13B illustrate an embodiment of an instrument system 1300 which is similar in many respects to the instrument system 1200 except that the second instrument is guided to the target position for accessing the heart. The instrument system 1300 is similarly configured for securing a port of an apical connector (which also may be referred to as a "heart connector" or a "tissue connector") to a heart wall (which also may be referred to as a "tissue wall"), coring a hole in the heart wall, and attaching a cannula to the port of the apical connector. The instrument system 1300 may be configured for use with the apical connector 1100 described above, including the valved cannula 1170 and the port 1106, or any of the other connectors described herein or in the applications listed above. FIGS. 13C-13I illustrate an example method of using the instrument system 1300 to secure the port 1106 of the apical connector 1100 in a heart wall, core a hole in the heart wall, and attach the valved cannula 1170 to the port 1106.

The instrument system 1300 may include a first instrument 1302 for securing the port 1106 of the connector 1100 to the heart wall via the anchoring device 1102, and a second instrument 1332 for coring a hole in the heart wall and attaching the valved cannula 1170 to the port 1106. The first instrument 1302 and the second instrument 1332 may be used together, as described below.

The first instrument 1302 may include a handle 1303 and a port interface 1313 rigidly attached to the handle 1303, such as by one or more connecting members 1311 extending therebetween. The port interface 1313 may be configured for removably attaching to and retaining a port of an apical connector, such as the port 1106 of the apical connector 1100, as shown. For example, the port interface 1313 may include one or more engagement protrusions 1315 (which also may be referred to as "engagement tabs") configured for inserting into the engagement apertures 1135 and/or the engagement notches 1137 of the port 1106. Each engagement protrusion 1315 may extend from an attachment finger or arm 1317 that is resilient or spring-like and configured to deflect radially outward from a natural position to a biased position when a biasing force is applied thereto via mating features of the port 1106 as the port interface 1313 is attached to the port 1106. As shown, the first instrument 1302 may be cannulated and configured for allowing the second instrument 1332 to extend therethrough. This advantageously guides the second instrument 1332 to a desired or target location such that the risk of malpositioning is reduced.

Figures 13C, 13D:
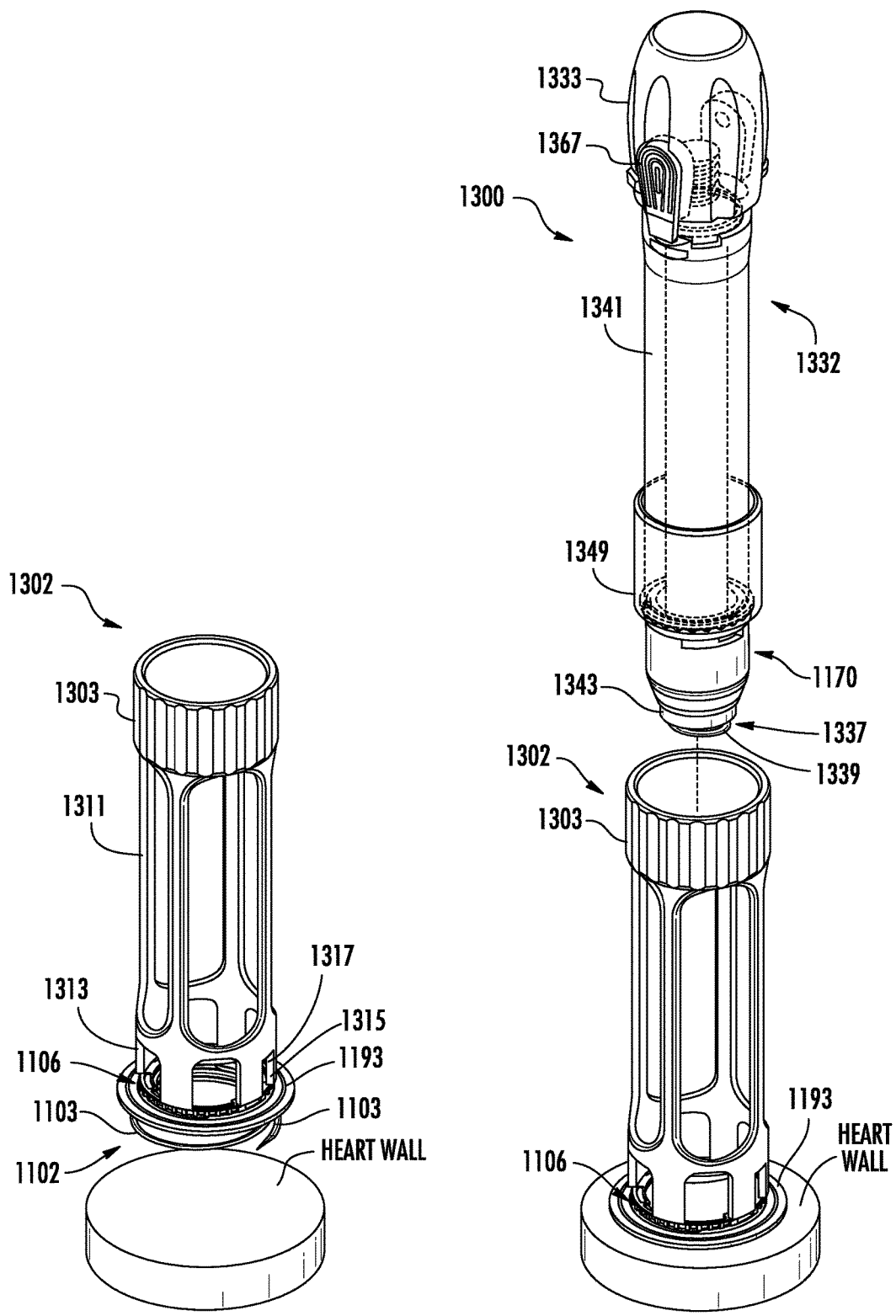
FIGS. 13C-13I show perspective views illustrating use of the instrument system of FIG. 13A to secure a port of an apical connector in a heart wall, core a hole in the heart wall, and attach a cannula to the port of the apical connector, in accordance with one or more embodiments of the present disclosure.

The second instrument 1332 may include a main handle 1333, a shaft 1335 rigidly attached to the main handle 1333 and extending distally therefrom, and a coring anchor 1337 rigidly attached to the distal end of the shaft 1335 and extending distally therefrom. The coring anchor 1337 may be configured for attaching to the heart wall. As shown, the coring anchor 1337 may include one or more helical coils 1339 configured for advancing into the heart wall. In other embodiments, the coring anchor 1337 may include one or more pins, prongs, barbs, hooks, staples, or other similar features configured for advancing into the heart wall. The second instrument 1332 also may include a sleeve 1341, a coring tube 1343 rigidly attached to the distal end of the sleeve 1341 and extending distally therefrom, and a cannula interface 1349 rigidly attached to the distal end of the sleeve 1341 and extending distally therefrom. The coring tube 1343 may be configured for contacting the heart wall and coring a hole therein, as described in detail below. The cannula interface 1349 may be configured for removably attaching to and retaining a cannula of an apical connector, such as the valved cannula 1170 of the apical connector 1100. For example, the cannula interface 1349 may include one or more engagement protrusions 1351 (which also may be referred to as "engagement tabs") configured for inserting into the engagement notches 1178 of the cannula 1170. As shown in FIGS. 13A and 13D, a distal portion of the coring tube 1343 may extend distally beyond the distal end of the cannula interface 1349 and beyond the distal end of the cannula 1170.

The sleeve 1341 may be configured for advancing the coring tube 1343 toward the heart wall and through the aperture 1114 of the port 1106 (previously attached to the heart wall via the anchoring device 1102) to core a hole in the heart wall at a target location, and for advancing the cannula interface 1349 (and the cannula 1170 attached thereto) toward the port 1106, as described in detail below. The sleeve 1341, the coring tube 1343, and the cannula interface 1349 may be cannulated and movably positioned over respective portions of the shaft 1335 and the coring anchor 1337. In particular, the sleeve 1341, the coring tube 1343, and the cannula interface 1349 may be configured to translate axially with respect to the main handle 1333, the shaft 1335, and the coring anchor 1337 from a proximal position, as shown in FIG. 13A, to a distal position, as shown in FIG. 13B. Such axial translation of the sleeve 1341 may be limited in the proximal direction by contact between the sleeve 1341 and the main handle 1333 and in the distal direction by contact between an inner flange 1355 of the sleeve 1341 and a boss 1357 of the shaft 1335. In some embodiments, as shown in FIG. 13A, the coring anchor 1337 may be positioned entirely within the coring tube 1343 when the sleeve 1341, the coring tube 1343, and the cannula interface 1349 are in the proximal position. In other embodiments, as shown in FIG. 13D, a distal portion of the coring anchor 1337 may extend distally beyond the distal end of the coring tube 1343 when the sleeve 1341, the coring tube 1343, and the cannula interface 1349 are in the proximal position. In some embodiments, the sleeve 1341, the coring tube 1243, and the cannula interface 1349 may be configured to rotate with respect to the main handle 1333 and the shaft 1335. In other embodiments, the sleeve 1341, the coring tube 1243, and the cannula interface 1349 may be rotatably keyed, either directly or indirectly, to the main handle 1333 and/or the shaft 1335.

The second instrument 1332 may be adjusted between a first configuration, as shown in FIG. 13A, for coring a hole in a heart wall and attaching the cannula 1170 to the port 1106, and a second configuration, as shown in FIG. 13B, for retrieving a tissue core removed from the heart wall and detaching the second instrument 1332 from the cannula 1170. The second instrument 1332 may include one or more buttons or switches 1367 positioned on the main handle 1333 and configured for releasably engaging the sleeve 1341. In particular, distal portions of the switches 1367, which may be formed as teeth, may releasably engage one or more engagement notches 1369 (which also may be referred to as "engagement recesses") defined in the sleeve 1341 at or near the proximal end of the sleeve 1341. When the second instrument 1332 is in the first configuration, engagement between the switches 1367 and the engagement notches 1369 may maintain the sleeve 1341, the coring tube 1343, and the cannula interface 1349 in their proximal position. Upon release of the switches 1367 (i.e., disengagement of the switches 1367 and the engagement notches 1369), the second instrument 1332 may be adjusted to the second configuration, in which the sleeve 1341, the coring tube 1343, and the cannula interface 1349 are in their distal position.

When the second instrument 1332 is in the first configuration, the sleeve 1341, the coring tube 1343, and the cannula interface 1349 may be rotatably keyed to the main handle 1333. For example, as shown, the main handle 1333 may include one or more engagement protrusions 1373 (which also may be referred to as "engagement tabs") extending from the distal end thereof and configured for engaging one or more engagement notches 1375 (which also may be referred to as "engagement recesses") defined in the proximal end of the sleeve 1341 when the sleeve 1341 is in its proximal position. As described above, the coring anchor 1337 may be rigidly attached to the shaft 1335, which may be rigidly attached to the main handle 1333. Accordingly, when the second instrument 1332 is in the first configuration, rotation of the main handle 1333 may result in rotation of the coring anchor 1337, the coring tube 1343, and the attached cannula 1170.

During use of the instrument system 1300, the port 1106 may be attached to the first instrument 1302 via the port interface 1313 and advanced toward the heart wall, as shown in FIG. 13C. The first instrument 1302, the port 1106, and the anchoring device 1102 may be axially translated toward the heart wall via the handle 1303. The first instrument 1302 may be oriented such that the distal end of the anchoring device 1102 contacts the outer surface of the heart wall while the central axis of the port 1106 is aligned with an approximate center of the desired implantation site. Once the anchoring device 1102 contacts the outer surface of the heart wall, the anchoring device 1102 may be advanced into the heart wall, by axial translation and/or rotation of the handle 1303, depending on the type of anchoring device 1102 used. For the coiled anchoring device 1102 shown, the handle 1303 may be rotated and axially translated according to the helical paths defined by the coils 1103. The anchoring device 1102 may be advanced into the heart wall until the distal end of the port 1106 and/or the sewing ring 1193 is adequately secured against the outer surface of the heart wall, such as by forming a substantially fluid tight or hemostatic seal thereabout. In certain embodiments, the anchoring device 1102 is configured to be secured in the heart wall after a predetermined number of rotations. In certain embodiments, a marker provides visual confirmation to a user that the port 1106 is secured and flush against the heart wall. In some embodiments, the sewing ring 1193 may be sutured to the heart wall to further secure the port 1106 to the heart wall, to enhance a seal between the sewing ring 1193 and the heart wall, and/or to further inhibit rotation of the anchoring device 1102 out of the heart wall. The first instrument 1302 may remain attached to the port 1106 via the port interface 1313, as shown in FIG. 13D, and may be used as a guide for the second instrument 1332.

Figures 13E, 13F:
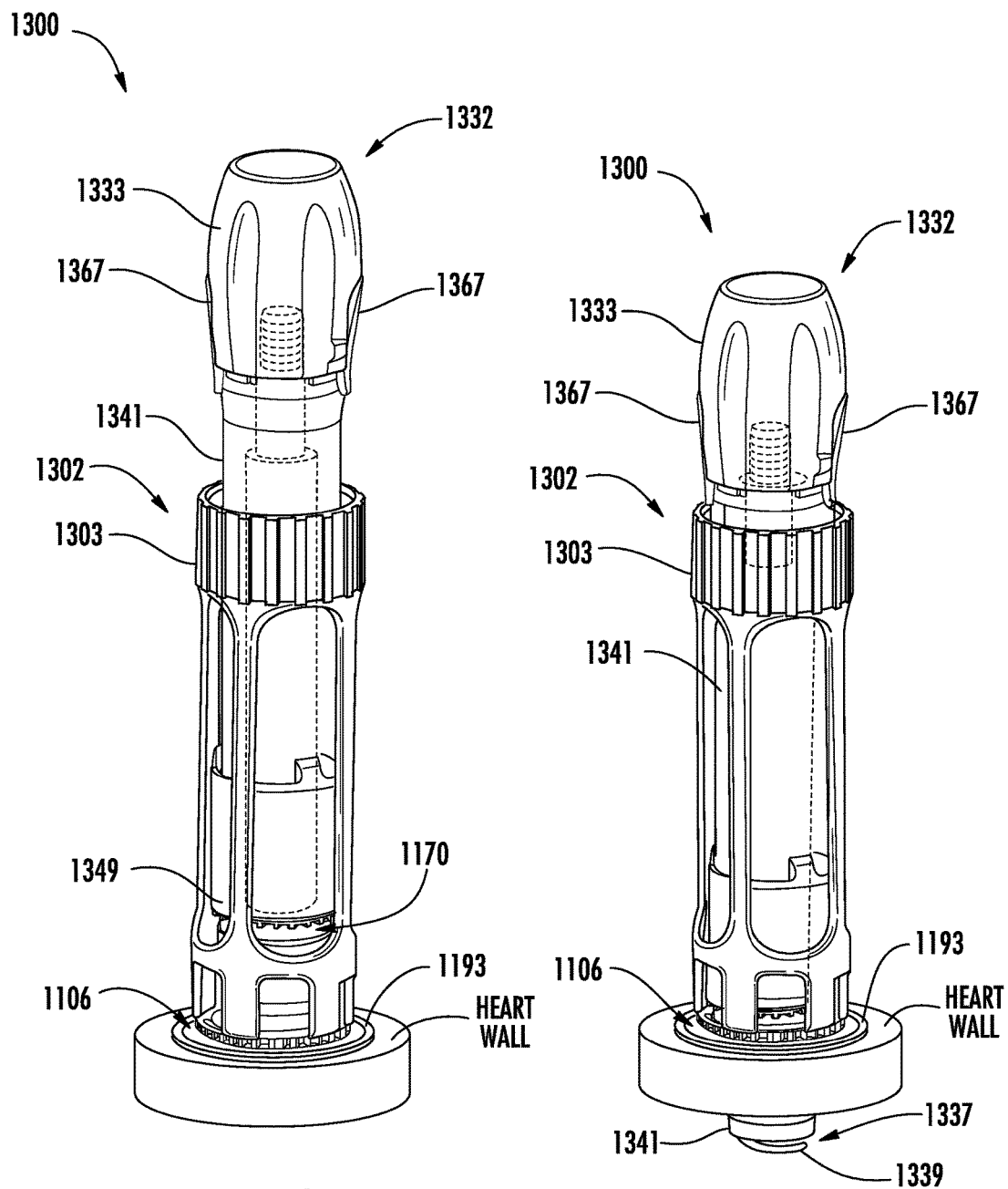

Next, with the second instrument 1332 in the first configuration, the valved cannula 1170 may be attached to the second instrument 1332 via the cannula interface 1349 and advanced toward the heart wall, as shown in FIG. 13D. The second instrument 1332 and the cannula 1170 may be placed through the handle 1303 of the first instrument 1302 in guided fashion, and the coring anchor 1337, the coring tube 1343, and the cannula 1170 may be axially translated toward the heart wall via the main handle 1333. The distal end of the second instrument 1332 may be inserted through the aperture 1114 of the port 1106 until the coring anchor 1337 contacts the outer surface of the heart wall, as shown in FIG. 13E. The coring anchor 1337 then may be advanced into the heart wall, by axial translation and/or rotation of the main handle 1333, depending on the type of coring anchor 1337 used. For the coiled coring anchor 1337 shown, the handle 1333 may be rotated and axially translated according to the helical path defined by the coil 1339.

As the coring anchor 1337 is advanced into the heart wall, the distal end of the coring tube 1343 approaches and eventually contacts the outer surface of the heart wall. At this point, the coring anchor 1337 may provide countertraction for advancing the coring tube 1343 into the heart wall. As the main handle 1333 is further rotated and axially translated according to the path of the coiled coring anchor 1337, the second instrument 1332 may simultaneously core a hole in the heart wall as the coring tube 1343 advances therethrough and position the valved cannula 1170 through the aperture 1114 of the port 1106 and at least partially through the heart wall via the hole formed therein. The main handle 1333 may be rotated and axially translated until the cannula 1170 securely attaches to the port 1106, as shown in FIG. 13F. The cannula 1170 may be attached to the port 1106 via the partial-turn locking mechanism or other means of attachment.

Figures 13G, 13H:
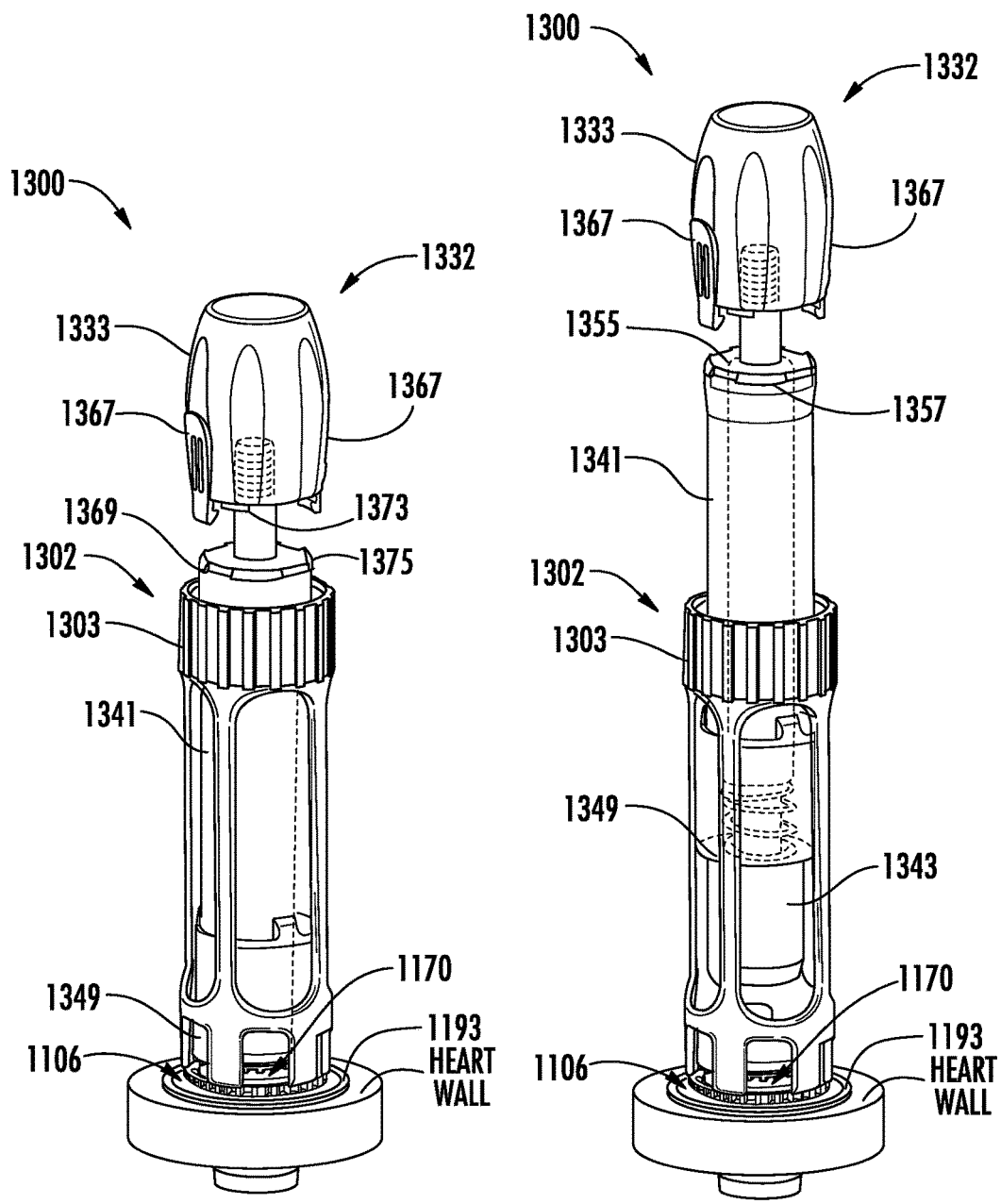
Figure 13I:
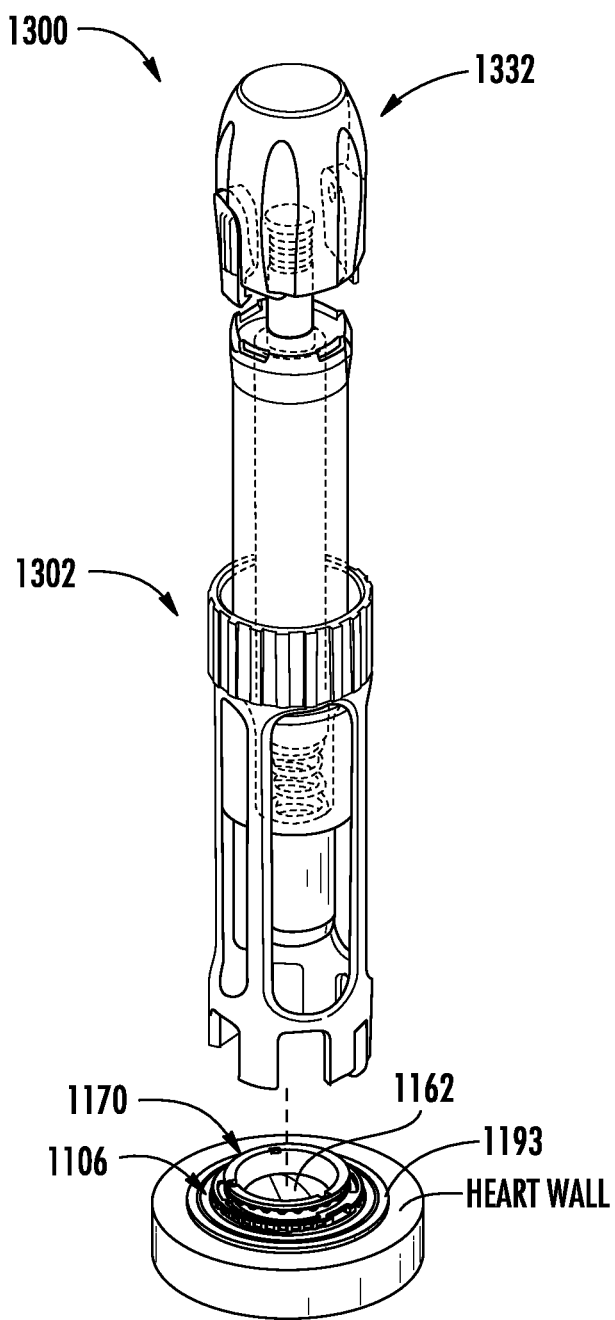

After the hole is formed in the heart wall and the cannula 1170 is securely attached to the port 1106, the switches 1367 may be released and the second instrument 1332 may be adjusted from the first configuration to the second configuration by pulling the main handle 1333 proximally away from the heart wall. As the second instrument 1332 is adjusted from the first configuration to the second configuration, the coring anchor 1337 may move into the coring tube 1343 while holding the tissue core removed from the heart wall, as shown in FIG. 13G. The cannula interface 1349 then may be detached from the cannula 1170 and the second instrument 1332 may be removed from the connector 1100, as shown in FIG. 13H. The coring tube 1343 and the coring anchor 1337 may be configured to retain the tissue core removed from the heart wall within the coring tube 1343. As the coring tube 1343 is removed from the cannula 1170, the hemostasis valve 1162 may close to prevent blood loss through the connector 1100. Next, the port interface 1313 may be detached from the port 1106 and the first instrument 1302 may be removed from the connector 1100, as shown in FIG. 13I. A VAD or other instrument then may be implanted in the heart wall via the connector 1100. In particular, an inlet tube of a VAD may be inserted at least partially through the cannula 1170 and at least partially through the hole in the heart wall such that the inlet tube is in communication with the ventricle of the heart. When the inlet tube is inserted through the cannula 1170, the hemostasis valve 1162 may assume an open position and may form a seal against the outer surface of the inlet tube.

Figure 14A:
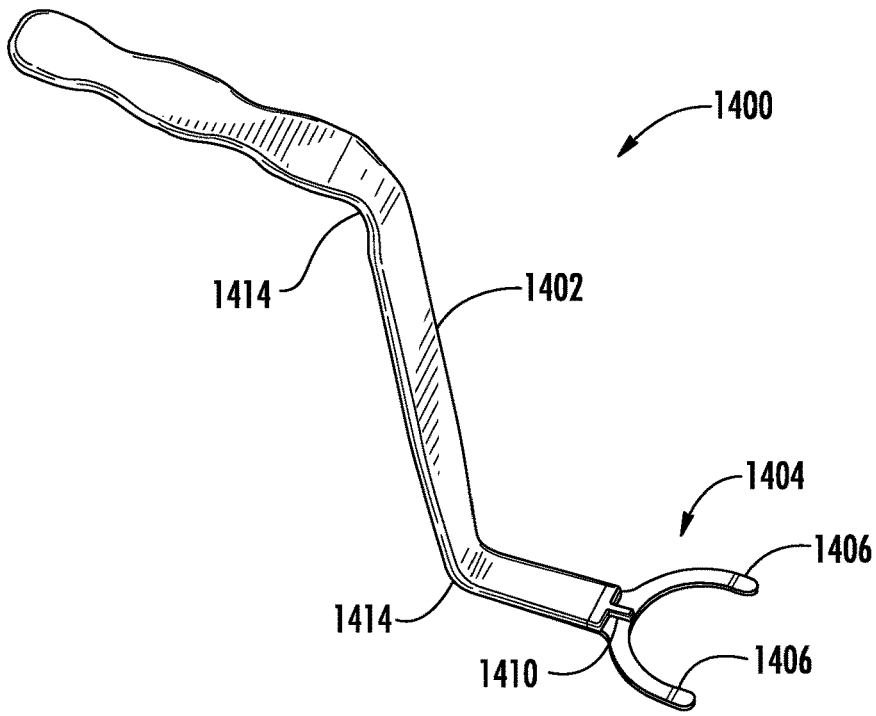
FIG. 14A shows a perspective view of an instrument for stabilizing an apical connector secured in a heart wall, in accordance with one or more embodiments of the present disclosure.
Figure 14B:
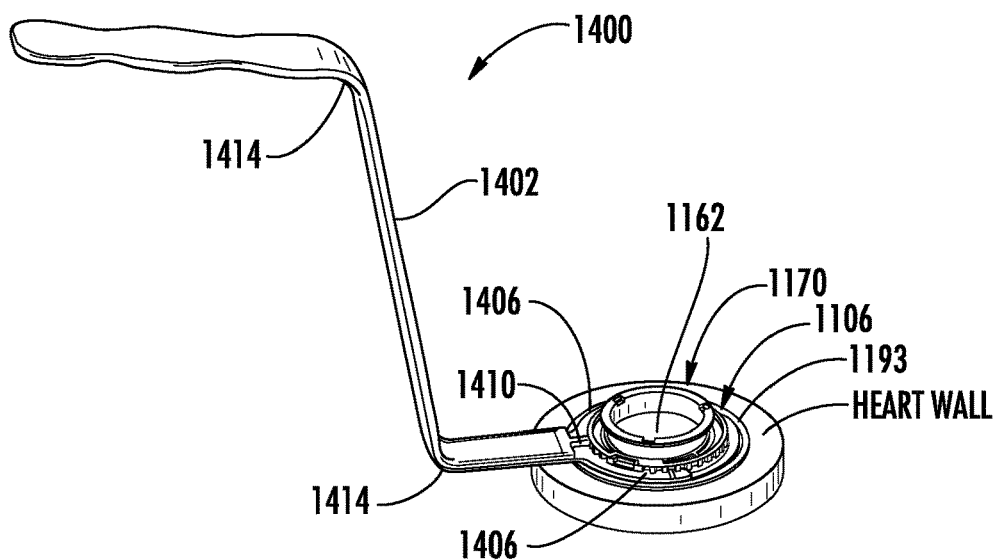
FIG. 14B shows a perspective view illustrating use of the instrument of FIG. 14A to stabilize an apical connector secured in a heart wall, in accordance with one or more embodiments of the present disclosure.

FIG. 14A illustrates an embodiment of an instrument 1400 for stabilizing an apical connector (which also may be referred to as a "heart connector" or a "tissue connector") secured in a heart wall (which also may be referred to as a "tissue wall"). The instrument 1400 may be used, for example, to stabilize the apical connector during implantation of a VAD, particularly during attachment of the VAD to the apical connector. The instrument 1400 may be configured for use with the apical connector 1100 described above, including the valved cannula 1170 and the port 1106, or any of the other connectors described herein or in the applications listed above. FIG. 14B illustrates an example method of using the instrument 1400 to stabilize the apical connector 1100 secured in the heart wall.

The instrument 1400 may include a handle 1402 and a connector interface 1404 attached to the distal end of the handle 1402. The connector interface 1404 may be configured for removably attaching to an apical connector, such as the apical connector 1100. As shown, the connector interface 1404 may include a pair of prongs 1406 (which also may be referred to as "arms") having a C-shaped configuration and defining a U-shaped opening for receiving a portion of the connector 1100. In particular, the prongs 1406 may be configured to receive a portion of the port 1106 therebetween, as shown in FIG. 14B. In this manner, the connector interface 1404 may be a port interface.

The connector interface 1404 also may include a stand-off feature 1410 configured to engage a portion of the connector 1100. As shown, the stand-off feature 1410 may be a protrusion positioned about an intersection of the prongs 1406 and aligned with a center of the connector interface 1404. In some embodiments, the stand-off feature 1410 may be configured to provide additional clearance between the connector 1100 and the VAD being attached thereto. The additional clearance may be for inserting locking mechanisms or the like. In some embodiments, the stand-off feature 1410 may be configured for insertion into a mating engagement feature of the connector 1100. For example, the stand-off feature 1410 may be configured for insertion into one or more of the engagement notches 1139 of the port 1106. As described above, the engagement notches 1139 may be configured for allowing the instrument 1400 to engage the port 1106 from a plurality of directions relative to the aperture 1114 of the port 1106. For example, as shown in FIG. 14B, the notches 1139 may provide discrete engagement positions every 10 degrees about the circumferential outer surface of the port 1106. The insertion of the stand-off feature 1410 into the mating engagement feature of the connector 1100 may provide the clearance desired for attachment of the VAD. Additionally, the engagement of the stand-off feature 1410 with the mating engagement feature of the connector 1100 may provide rotational stabilization of the connector 1100 relative to the instrument 1400, thereby providing additional control and stabilization and also potentially reducing loads applied to the patient's heart during attachment of the VAD.

In some embodiments, portions of the instrument 1400 may be moldable or pliable such that portions of the instrument 1400 may be shaped or reshaped during a procedure, such as implantation of the VAD. For example, in some embodiments, the prongs 1406 may be manually reshaped or reconfigured as needed to better access a connector secured to the patient's heart. Additionally, in some embodiments, the handle 1402 may be reshaped depending on the size, orientation, and amount of clearance in the surgical field. For example, bends 1414 in the handle 1402 may be adjusted or straightened, as desired, to better accommodate the surgical field. Certain embodiments of tools that may be used to engage and stabilize ventricular cuffs secured to a heart are described in the '308 application. The instrument 1400 may have features and characteristics similar to those of the various embodiments of tools described in the '308 application and may be used according to methods similar to those described therein.

Figure 15A:
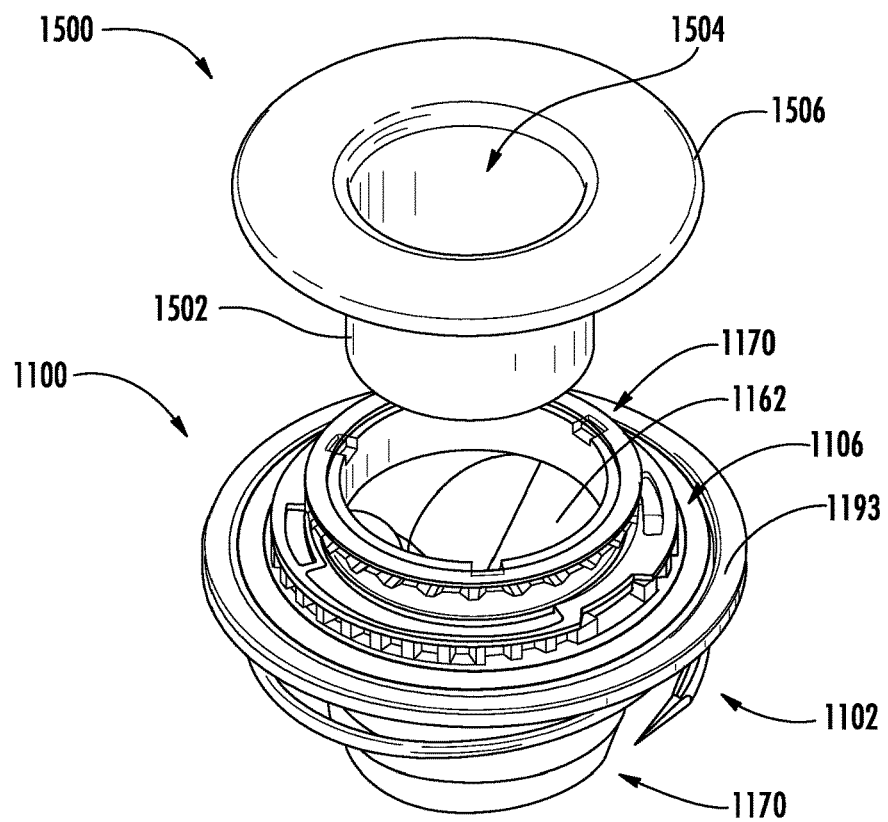
FIG. 15A shows a perspective view of an instrument for allowing inspection of a ventricle of a heart through an apical connector secured in a heart wall, in accordance with one or more embodiments of the present disclosure.
Figure 15B:
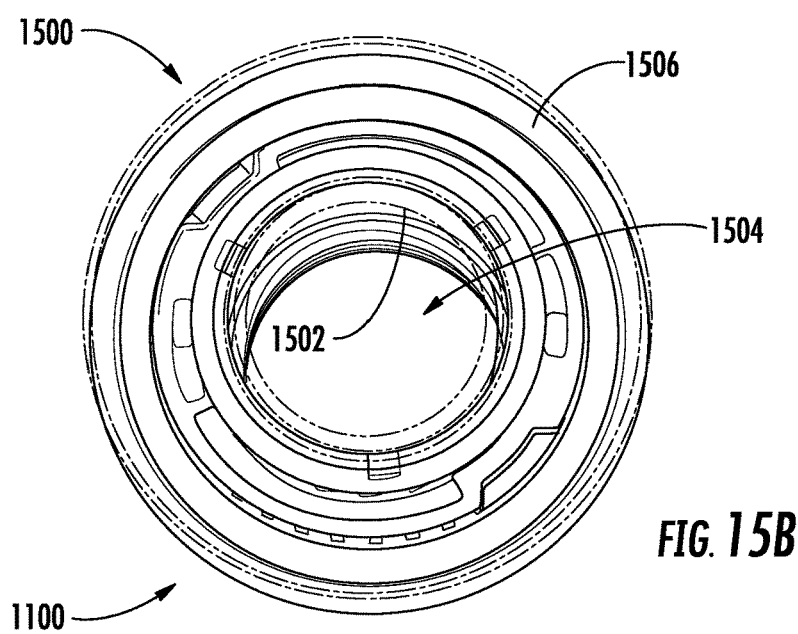
FIG. 15B shows a perspective view illustrating use of the instrument of FIG. 15A to allow inspection of a ventricle of a heart through an apical connector secured in a heart wall, in accordance with one or more embodiments of the present disclosure.

FIG. 15A illustrates an embodiment of an instrument 1500 for allowing inspection of a ventricle of a heart through an apical connector (which also may be referred to as a "heart connector" or a "tissue connector") secured in a heart wall (which also may be referred to as a "tissue wall"). The instrument 1500 may be used, for example, to allow visual and/or tactile inspection of the ventricle to identify any thrombus that may be present on an inner surface of the heart wall and to facilitate removal of such thrombus. The instrument 1500 may be configured for use with the apical connector 1100 described above, including the valved cannula 1170 and the port 1106, or any of the other connectors described herein or in the applications listed above. FIG. 15B illustrates an example method of using the instrument 1500 to allow inspection of a ventricle of a heart through the apical connector 1100 secured in a heart wall.

In certain embodiments, the outer diameter (OD) of the instrument 1500 is dimensioned and configured to correspond to the valve 1162 and/or the aperture 1114 of the port 1106. In certain embodiments, the inner diameter (ID) of the instrument 1500 is dimensioned and configured to correspond to an instrument to be received therethrough. In certain embodiments, the ID is dimensioned and configured to provide a lumen for visual inspection therethrough.

The instrument 1500 may be formed as a substantially tube-shaped member configured for positioning at least partially through an apical connector, such as the apical connector 1100, and at least partially through a heart wall in which the apical connector is secured. As shown, the instrument 1500 may include a main tube 1502 defining an aperture 1504 therethrough, and a proximal flange 1506 fixedly attached to the main tube 1502. The main tube 1502 may be configured for insertion within the cannula 1170 such that the hemostasis valve 1162 opens and forms a substantially fluid-tight seal along the outer circumferential surface of the main tube 1502. The leading edge of the main tube 1502 may be rounded to reduce the risk of damaging the leaflets of the valve 1162 when they are pushed open. The aperture 1504 of the main tube 1502 may be configured to allow insertion of a clinician's finger or a separate instrument therethrough for tactile inspection of the ventricle of the heart. The aperture 1504 also may allow for visual inspection of the ventricle. The proximal flange 1506 may be configured for abutting the proximal end of the connector 1100, such as the proximal end of the cannula 1170, thereby limiting insertion of the main tube 1502 within the cannula 1170 and stabilizing the instrument 1500 with respect to cannula 1170 and the overall connector 1100. In some embodiments, the proximal flange 1506 may be positioned at the proximal end of the main tube 1502, as shown. In other embodiments, the proximal flange 1506 may be positioned near but offset from the proximal end of the main tube 1502.

FIG. 15B shows the instrument 1500 in a fully inserted position with respect to the apical connector 1100, in which the proximal flange 1506 abuts the proximal end of the cannula 1170, and the main tube 1502 is positioned at least partially within the cannula 1170. As shown, the main tube 1502 may extend into the cannula 1170 such that the hemostasis valve 1162 opens and forms a substantially fluid-tight seal along the outer circumferential surface of the main tube 1502. In some embodiments, the distal end of the main tube 1502 may be positioned within the cannula 1170 when the instrument 1500 is in the fully inserted position. In other embodiments, the distal end of the main tube 1502 may extend distally beyond the distal end of the cannula 1170 when the instrument 1500 is in the fully inserted position. With the instrument 1500 in the fully inserted position, a clinician may visually inspect the ventricle through the aperture 1504 and/or may insert a finger or a separate instrument through the aperture for tactile inspection of the ventricle. In particular, the clinician may use the instrument 1500 to identify any thrombus that may be present on an inner surface of the heart wall and to remove any thrombus that may compromise operation of a VAD implanted via the connector 1100. After inspection of the ventricle and removal of any thrombus, the instrument 1500 may be removed from the apical connector 1100. As the main tube 1502 is removed from the cannula 1170, the hemostasis valve 1162 may close to prevent blood loss through the connector 1100.

In some embodiments, as shown, the outer diameter of the proximal flange 1506 may be approximately equal to the outer diameter of the apical connector 1100. In this manner, the proximal flange 1506 may cover and protect the connector 1100 during inspection. Additionally, such sizing of the proximal flange 1506 may allow a clinician to use the instrument 1500, prior to securing the apical connector 1100 to the heart wall, as a template to approximate positioning of the port 1106 and/or the sewing ring 1193 on the heart wall. In some embodiments, the outer diameter of the proximal flange 1506 may be approximately equal to the outer diameter of the anchoring device 1102. Such sizing of the proximal flange 1506 may allow a clinician to use the instrument 1500, prior to securing the apical connector 1100 to the heart wall, as a template to approximate positioning of the anchoring device 1102 within the heart wall.

Many modifications of the embodiments of the present disclosure will come to mind to one skilled in the art to which the disclosure pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apical connector for use in a heart wall, the apical connector comprising:

a port defining an aperture, the port including a flange defining a proximal side and a distal side disposed opposite one another in a direction of a central axis of the apical connector; and an anchoring device extending distally from the port and configured for advancing at least partially through the heart wall, the anchoring device including a plurality of coils offset from one another and arranged about the central axis of the apical connector such that the coils follow separate helical paths in the heart wall, wherein each of the coils is coaxial with the central axis of the apical connector, wherein each of the coils includes a proximal portion disposed on the proximal side of the flange and a distal portion disposed on the distal side of the flange, wherein each of the coils continuously extends from the proximal portion to the distal portion through the flange, and wherein each of the coils is fixedly attached to the port at an attachment point between the proximal portion of the coil and the proximal side of the flange.

2. The apical connector of claim 1, wherein distal ends of the coils are equally spaced apart from one another in a circumferential direction with respect to the central axis of the apical connector.

3. The apical connector of claim 1, wherein the attachment points are equally spaced apart from one another in a circumferential direction with respect to the central axis of the apical connector.

4. The apical connector of claim 1, wherein the plurality of coils comprises two coils, wherein distal ends of the two coils are spaced apart from one another by approximately 180 degrees in a circumferential direction with respect to the central axis of the apical connector, and wherein the attachment points are spaced apart from one another by approximately 180 degrees in the circumferential direction with respect to the central axis of the apical connector.

5. The apical connector of claim 1, wherein each of the coils has a radially expanding shape such that a helical diameter of the coil increases from a proximal end to a distal end of the coil.

6. The apical connector of claim 1, further comprising a cannula configured for advancing through the aperture of the port and at least partially through the heart wall.

7. The apical connector of claim 6, wherein the cannula comprises a locking tab configured to engage the port and lock the cannula with respect to the port.

8. The apical connector of claim 7, wherein the locking tab is offset from a proximal end of the cannula and extends along an outer circumferential surface of the cannula.

9. The apical connector of claim 7, wherein the cannula further comprises a partial flange, and wherein the locking tab extends from the partial flange and is configured to deflect from a natural position to a biased position with respect to the partial flange.

10. The apical connector of claim 9, wherein the port comprises a recess defined in a proximal end of the port and configured to receive the locking tab and the partial flange of the cannula.

11. The apical connector of claim 10, wherein the port further comprises an undercut groove in communication with the recess and configured to receive the locking tab and the partial flange of the cannula upon rotation of the cannula with respect to the port.

12. The apical connector of claim 10, wherein the port further comprises a locking protrusion configured to deflect the locking tab of the cannula from the natural position to the biased position upon rotation of the cannula with respect to the port in a first direction.

13. The apical connector of claim 12, wherein the port further comprises a stop protrusion configured to engage the partial flange of the cannula to limit rotation of the cannula with respect to the port in the first direction.

14. The apical connector of claim 6, wherein the cannula comprises an elastomer covering molded over a proximal portion of the cannula.

15. The apical connector of claim 14, wherein the cannula further comprises a plurality of engagement recesses defined in a proximal end of the cannula, and wherein the elastomer covering extends partially over each of the engagement recesses.

16. The apical connector of claim 6, further comprising a valve positioned within the cannula and configured for controlling fluid communication therethrough.

17. The apical connector of claim 1, wherein the proximal portions of the coils are fixedly attached to the port via respective welds between the proximal portions of the coils and the proximal side of the flange.

18. The apical connector of claim 1, wherein, for each of the coils, the proximal portion and the distal portion of the coil are integrally formed with one another from an elongated member.

19. The apical connector of claim 1, wherein the distal portions of the coils have a helical shape, and wherein the proximal portions of the coils have a curved shape.

20. The apical connector of claim 1, wherein the proximal portions of the coils extend along the proximal side of the flange in a circumferential direction with respect to the central axis of the apical connector.

* * * * *